United States Patent
Salomon et al.

(10) Patent No.: US 12,209,284 B2
(45) Date of Patent: Jan. 28, 2025

(54) GENE EXPRESSION PROFILES ASSOCIATED WITH CHRONIC ALLOGRAFT NEPHROPATHY

(71) Applicant: The Scripps Research Institute, La Jolla, CA (US)

(72) Inventors: Daniel R. Salomon, San Diego, CA (US); Sunil M. Kurian, San Diego, CA (US); Steven R. Head, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 18/323,590

(22) Filed: May 25, 2023

(65) Prior Publication Data

US 2023/0374595 A1    Nov. 23, 2023

Related U.S. Application Data

(63) Continuation of application No. 16/803,337, filed on Feb. 27, 2020, now Pat. No. 11,821,037, which is a continuation of application No. 15/666,920, filed on Aug. 2, 2017, now abandoned, which is a continuation of application No. 13/261,130, filed as application No. PCT/US2010/041598 on Jul. 9, 2010, now Pat. No. 9,752,191.

(60) Provisional application No. 61/224,317, filed on Jul. 9, 2009, provisional application No. 61/224,328, filed on Jul. 9, 2009.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/112* (2013.01); *C12Q 2600/136* (2013.01); *C12Q 2600/158* (2013.01)

(58) Field of Classification Search
CPC ............ C12Q 1/6883; C12Q 2600/106; C12Q 2600/112; C12Q 2600/136; C12Q 2600/158
USPC .............................................. 435/6.1; 506/9
See application file for complete search history.

(56) References Cited

U.S. PATENT DOCUMENTS

| | | |
|---|---|---|
| 5,210,015 A | 5/1993 | Gelfand et al. |
| 5,458,852 A | 10/1995 | Buechler |
| 5,480,792 A | 1/1996 | Buechler et al. |
| 5,525,524 A | 6/1996 | Buechler et al. |
| 5,538,848 A | 7/1996 | Livak et al. |
| 5,578,832 A | 11/1996 | Trulson et al. |
| 5,631,734 A | 5/1997 | Stern et al. |
| 5,679,526 A | 10/1997 | Buechler et al. |
| 5,824,799 A | 10/1998 | Buechler et al. |
| 5,851,776 A | 12/1998 | Valkirs |
| 5,855,527 A | 1/1999 | Koole |
| 5,863,736 A | 1/1999 | Haaland |
| 5,922,615 A | 7/1999 | Nowakowski et al. |
| 5,939,272 A | 8/1999 | Buechler et al. |
| 5,947,124 A | 9/1999 | Buechler et al. |
| 5,985,579 A | 11/1999 | Buechler et al. |
| 6,019,944 A | 2/2000 | Buechler |
| 6,020,165 A | 2/2000 | Yue |
| 6,113,855 A | 9/2000 | Buechler |
| 6,143,576 A | 11/2000 | Buechler |
| 6,187,534 B1 | 2/2001 | Strom et al. |
| 6,623,738 B1 | 9/2003 | Tessier-Lavigne |
| 6,878,518 B2 | 4/2005 | Whitehead |
| 6,927,028 B2 | 8/2005 | Dennis et al. |
| RE39,920 E | 11/2007 | Umansky et al. |
| 7,415,358 B2 | 8/2008 | Mendrick |
| 7,426,441 B2 | 9/2008 | Mendrick |
| 7,615,355 B2 | 11/2009 | Papadopoulos et al. |
| 7,645,575 B2 | 1/2010 | Wohlgemuth et al. |
| 7,741,038 B2 | 6/2010 | Sarwal et al. |
| 7,785,797 B2 | 8/2010 | Wohlgemuth et al. |
| 7,811,767 B2 | 10/2010 | Raulf et al. |
| 7,883,858 B2 | 2/2011 | Hood et al. |
| 7,994,286 B2 | 8/2011 | Watts |
| 7,998,687 B2 | 8/2011 | Grass |
| 8,003,333 B2 | 8/2011 | Charlton |
| 8,333,970 B2 | 12/2012 | Aukerman et al. |
| 8,486,626 B2 | 7/2013 | Umansky et al. |
| 8,512,953 B2 | 8/2013 | Saito et al. |
| 8,586,006 B2 | 11/2013 | Hood et al. |
| 8,735,080 B2 | 5/2014 | Labrie et al. |
| 9,102,983 B2 | 8/2015 | Winkler |

(Continued)

FOREIGN PATENT DOCUMENTS

| | | |
|---|---|---|
| EP | 1850130 B1 | 11/2011 |
| EP | 2209916 B1 | 12/2011 |

(Continued)

OTHER PUBLICATIONS

Flechner et al. Kidney Transplant Rejection and Tissue Injury by Gene Profiling of Biopsies and Peripheral Blood Lymphocytes. American Journal of Transplantation 2004; 4: 1475-1489. (Year: 2004).*

(Continued)

*Primary Examiner* — Yih-Horng Shiao

(74) *Attorney, Agent, or Firm* — Duane Morris LLP; Thomas J. Kowalski

(57) ABSTRACT

By a genome-wide gene analysis of expression profiles of over 50,000 known or putative gene sequences in peripheral blood, the present inventors have identified a consensus set of gene expression-based molecular biomarkers associated with chronic allograft nephropathy and/or interstitial fibrosis and tubular atrophy CAN/IFTA and subtypes thereof. These genes sets are useful for diagnosis, prognosis, monitoring and/or subtyping of CAN/IFTA.

29 Claims, 2 Drawing Sheets

(56) References Cited

U.S. PATENT DOCUMENTS

| | | | |
|---|---|---|---|
| 9,752,191 | B2 | 9/2017 | Salomon |
| 2004/0126767 | A1 | 7/2004 | Anderberg et al. |
| 2006/0088836 | A1* | 4/2006 | Wohlgemuth ....... C12Q 1/6888 435/6.14 |
| 2006/0216722 | A1 | 9/2006 | Betsholtz |
| 2006/0263813 | A1 | 11/2006 | Rosenberg et al. |
| 2006/0281122 | A1 | 12/2006 | Bryant |
| 2007/0099251 | A1 | 5/2007 | Zhang et al. |
| 2007/0122806 | A1 | 5/2007 | Strom et al. |
| 2008/0044403 | A1 | 2/2008 | Sawitzki et al. |
| 2008/0131441 | A1 | 6/2008 | Suthanthiran |
| 2009/0053195 | A1 | 2/2009 | Raulf et al. |
| 2009/0053695 | A1 | 2/2009 | Tanigawara et al. |
| 2009/0202531 | A1 | 8/2009 | Aukerman et al. |
| 2009/0311745 | A1 | 12/2009 | Liebeton |
| 2010/0022627 | A1 | 1/2010 | Scherer |
| 2010/0068711 | A1 | 3/2010 | Umansky et al. |
| 2010/0086928 | A1 | 4/2010 | Feinberg |
| 2010/0120041 | A1 | 5/2010 | Quaggin |
| 2010/0196426 | A1 | 8/2010 | Skog |
| 2010/0233716 | A1 | 9/2010 | Saint-Mezard et al. |
| 2010/0266579 | A1 | 10/2010 | Cook et al. |
| 2010/0305000 | A1 | 12/2010 | Mathew et al. |
| 2011/0003708 | A1 | 1/2011 | Kinar et al. |
| 2011/0034532 | A1 | 2/2011 | Li et al. |
| 2011/0039710 | A1 | 2/2011 | Tibbetts |
| 2011/0065599 | A1 | 3/2011 | Labrie et al. |
| 2011/0086051 | A1 | 4/2011 | Zuckerman et al. |
| 2011/0171750 | A1 | 7/2011 | Struck et al. |
| 2012/0003633 | A1 | 1/2012 | Kuijpers et al. |
| 2012/0094853 | A1 | 4/2012 | Clark et al. |
| 2012/0101001 | A1 | 4/2012 | Suthanthiran |
| 2012/0135882 | A1 | 5/2012 | Bottinger |
| 2012/0192878 | A1 | 8/2012 | Toyoda |
| 2012/0219542 | A1 | 8/2012 | Reiser |
| 2012/0251527 | A1 | 10/2012 | Reiser |
| 2013/0012860 | A1 | 1/2013 | Suthanthiran et al. |
| 2013/0040301 | A1 | 2/2013 | Strom et al. |
| 2013/0045873 | A1 | 2/2013 | Hood et al. |
| 2013/0115232 | A1 | 5/2013 | Ferrara et al. |
| 2013/0143223 | A1 | 6/2013 | Hernandez-Fuentes et al. |
| 2013/0143755 | A1 | 6/2013 | Sarwal et al. |
| 2013/0216557 | A1 | 8/2013 | Bienkowska et al. |
| 2013/0236437 | A1 | 9/2013 | Bishopric et al. |
| 2014/0030266 | A1 | 1/2014 | Bucala et al. |
| 2014/0045915 | A1 | 2/2014 | Skog et al. |
| 2014/0121126 | A1 | 5/2014 | Bivona |
| 2015/0011401 | A1 | 1/2015 | Davicioni |
| 2015/0167085 | A1 | 6/2015 | Salomon et al. |

FOREIGN PATENT DOCUMENTS

| | | |
|---|---|---|
| WO | WO 97/10365 A1 | 3/1997 |
| WO | WO 97/27317 A1 | 7/1997 |
| WO | WO 02/38561 A1 | 5/2002 |
| WO | WO 03/082859 A1 | 10/2003 |
| WO | WO 2004/052359 A1 | 6/2004 |
| WO | WO 2004/059293 A2 | 7/2004 |
| WO | WO 2005/066156 A1 | 7/2005 |
| WO | WO 2007/104537 A2 | 9/2007 |
| WO | WO 2008/021290 A2 | 2/2008 |
| WO | WO 2008/048970 A2 | 4/2008 |
| WO | WO 2009/060035 A1 | 5/2009 |
| WO | WO 2009/151600 A2 | 12/2009 |
| WO | WO 2011/066380 A1 | 6/2011 |
| WO | WO 2013/049892 A1 | 4/2013 |
| WO | WO 2014/074501 A1 | 5/2014 |

OTHER PUBLICATIONS

Rodder et al., Renal al log rafts with IF/TA display distinct expression profiles of metzincins and related genes, American Journal of Transplantation (Feb. 2009) vol. 9, No. 3, p. 517-526.

Powell, et al. Managing renal transplant ischemia reperfusion injury: novel therapies in the pipeline, Clin Transplant. Jul.-Aug. 2013;27(4):484-91. doi: 10.1111/cu.12121. Epub Apr. 25, 2013.

Salvadori, et al. Update on ischemia-reperfusion injury in kidney transplantation: Pathogenesis and treatment. World J Transplant. Jun. 24, 2015;5(2):52-67. doi: 10.5500/wjt.v5.i2.52.

Thomas, et al. Chronic kidney disease and its complications. Prim Care. Jun. 2008:35(2):329-44, vii, doi: 10.1016/j.pop.2008.01.008. Review.

Tonelli, et al. Chronic kidney disease and mortality risk: a systematic review. J Am Soc Nephrol. Jul. 2006:17(7):2034-47. Epub May 31, 2006.

Bao, et al. A novel accurate rapid ELISA for detection of urinary connective tissue growth factor, a biomarker of chronic allograft nephropathy. Transplant Proc. Sep. 2008;40(7):2361-4. doi: 10.1016/j.transproceed.2008.07.122.

Chang, et al. Prediction of chronic allograft damage index of renal allografts using serum level of plasminogen activator inhibitor-1. Clin Transplant. Mar.-Apr. 2009;23(2):206-12, doi: 10.1111/j.1399-0012.2009.00970.x. Epub Feb. 11, 2009.

International search report and written opinion dated May 24, 2011 for PCT/US2010/041598.

International search report and written opinion dated Dec. 23, 2014 for PCT/US2014/054735.

Maluf, et al. Molecular pathways involved in loss of kidney graft function with tubular atrophy and interstitial fibrosis. Mol Med. May-Jun. 2008;14(5-6):276-85. doi: 10.2119/2007-00111.Maluf.

Scherer, et al. Transcriptome changes in renal allograft protocol biopsies at 3 months precede the onset of interstitial fibrosis/tubular atrophy (IF/TA) at 6 months. Nephrol Dial Transplant. Aug. 2009:24(8):2567-75. doi: 10.1093/ndt/gfp183. Epub Apr. 27, 2009.

F. Harrell, Regression Modeling Strategies: with applications to linear models, logistic regression, and survivial anaysis. Springer, New York 2001.

Nankivell. Subclinical renal allograft rejection and protocol biopsies: quo vadis? Nat Clin Pract Nephrol. 2008; 4(3): 134-5.

Pascual, et al. The clinical usefulness of the renal allograft biopsy in the cyclosporine era: a prospective study. Transplantation. Mar. 15, 1999;67(5):737-41.

Tou, J.T., and Gonzalez, R.C. 1974: Pattern Recognition Principals, Addison-Wesley, Reading, Massachusetts.

Vasconcellos, et al. Cytotoxic lymphocyte gene expression in peripheral blood leukocytes correlates with rejecting renal allografts. Transplantation. Sep. 15, 1998;66(5):562-6.

U.S. Appl. No. 14/481,167, filed Sep. 9, 2014, Salomon et al.

Banasik, et al. Chronic allograft nephropathy—immunologic and nonimmunologic factors, Ann Transplant, 2006;11(1):7-10.

Bolstad, et al. A comparison of normalization methods for high density oligonucleotide array data based on variance and bias. Bioinformatics, Jan. 22, 2003;19(2):185-93.

Brouard, et al. Identification of a peripheral blood transcriptional biomarker panel associated with operational renal allograft tolerance. Proc Natl Acad Sci U S A. Sep. 25, 2007;104(39):15448-53. Epub Sep. 14, 2007.

Brown, et al. Knowledge-based analysis of microarray gene expression data by using support vector machines. Proc Natl Acad Sci U S A. 2000, 97(1): 262-7.

Calne, et al. Cyclosporin A in patients receiving renal allografts from cadaver donors. Lancet. Dec. 23-30, 1978;2(8104-5):1323-7.

Chapman. Longitudinal analysis of chronic allograft nephropathy: clinicopathologie correlations, Kidney Int Suppl. 2005; (99): S108-12.

Chau, et al. Validation of analytic methods for biomarkers used in drug development, Clin Cancer Res. Oct. 1, 2008;14(19):5967-76. doi: 10.1158/1078-0432.CCR-07-4535.

Clarke, et al. Characterization of renal allograft rejection by urinary proteomic. analysis. Ann Surg. May 2003:237(5):660-4; discussion 664-5.

Colvin, RB. Chronic allograft nephropathy. N Engl J Med. Dec. 11, 2003;349(24):2288-90.

(56) References Cited

OTHER PUBLICATIONS

Dabney, AR, Classification of microarrays to nearest centroids. Bioinformatics, Nov. 15, 2005:21(22):4148-54. Epub Sep. 20, 2005.
De Mattos, et al. Nephrotoxicity of immunosuppressive drugs: long-term consequences and challenges for the future. Am J Kidney Dis. Feb. 2000:35(2):333-46.
Deng, et al. Noninvasive discrimination of rejection in cardiac allograft recipients using gene expression profiling. Am J Transplant. Jan. 2006:6( 1): 150-60.
Derisi, et al. Use of a cDNA microarray to analyse gene ession patterns in human cancer. Nat Genet. Dec. 1996;14(4):457-60.
Diaz-Uriarte, et al. Gene selection and classification of microarray data using random forest. BMC bioinformatics. 2006; 7: 3.
Dudoit. Comparison of discrimination methods for the classification of tumors using gene expression data. Journal of the American Statistical Association 97: 77-87, 2002.
Eisen, et al. Cluster analysis and display of genome-wide expression patterns. Proc Nati Acad Sci U S A. Dec. 8, 1998;95(25):14863-8.
Flechner, et al. De novo kidney transplantation without use of calcineurin inhibitors preserves renal structure and function at two years. Am J Transplant. Nov. 2004;4(11):1776-85.
Flechner, et al. Kidney transplant rejection and tissue injury by gene profiling of biopsies and peripheral blood lymphocytes. Am J Transplant. Sep. 2004;4(9):1475-89.
Flechner, et al. Kidney transplantation with sirolimus and mycophenolate mofetil-based immunosuppression: 5-year results of a randomized prospective trial compared to calcineurin inhibitor drugs. Transplantation. Apr. 15, 2007:83(7):883-92.
Gibbs, et al. Quantitative detection of changes in cytokine gene expression in peripheral blood mononuclear cells correlates with and precedes acute rejection in renal transplant recipients. Transpl Immunol. Jun. 2005;14(2):99-108. Epub Mar. 29, 2005.
Gibson, et al. A novel method for real time quantitative RT-PCR. Genome Res. Oct. 1996;6(10):995-1001.
GP. GraphPad QuickCalcs: free statistical calculators. GraphPad Software. 2014. Accessed Dec. 9, 2014 http://www.graphpad.com/quickcalcs/index.cfm.
Guo, et al. Regularized linear discriminant analysis and its application in microarrays. Biostatistics. Jan. 2007;8(1):86-100. Epub Apr. 7, 2006.
Harrell, et al. Multivariable prognostic models: issues in developing models, evaluating assumptions and adequacy, and measuring and reducing errors. Statistics in medicine. 1996; 15(4): 361-87.
Heid, et al. Real time quantitative PCR. Genome Res. Oct. 1996;6(10):986-94.
Holland, et al. Detection of specific polymerase chain reaction product by utilizing the 5'—3' exonuclease activity of Thermus aquaticus DNA polymerase. Proc Natl Acad Sci U S A. Aug. 15, 1991;88(16):7276-80.
Horwitz, et al. Detection of cardiac allograft rejection and response to immunosuppressive therapy with peripheral blood gene expression. Circulation. Dec. 21, 2004;110(25):3815-21. Epub Dec. 6, 2004.
Hsu, et al. A comparison of methods for multiclass support vector machines. IEEE Trans Neural Netw. 2002;13(2):415-25. doi: 10.1109/72.991427.
Huang, et al. Classification of malignant pediatric renal tumors by gene expression. Pediatr Blood Cancer. Jun. 2006;46(7):728-38.
Hymes, et al. Prevalence of clinical rejection after surveillance biopsies in pediatric renal transplants: does early subclinical rejection predispose to subsequent rejection episodes? Pediatr Transplant. Nov. 2009;13(7):823-6. doi: 10.1111/j.1399-3046.2009.01200.x. Epub Jun. 8, 2009.
Jevnikar, et al. Late kidney allograft loss: what we know about it, and what we can do about it, Clin J Am Soc Nephrol, Mar. 2008;3 Suppl 2:856-67. doi: 10.2215/CJN.03040707.
Kurian, et al. Applying genomics to organ transplantation medicine in both discovery and validation of biomarkers. Int Immunopharmacol. Dec. 20, 2007;7(14):1948-60. Epub Aug. 9, 2007.

Kurian, et al. Biomarkers for early and late stage chronic allograft nephropathy by proteogenomic profiling of peripheral blood. PLoS One. Jul. 10, 2009;4(7):e6212. doi: 10.1371/journal.pone.0006212.
Kurian. Genomics and proteomics in transplantation. Current opinion in organ transplantation. 2005, 10: 193-197.
Kurian, et al. Molecular classifiers for acute kidney transplant rejection in peripheral blood by whole genome gene expression profiling. Am J Transplant. May 2014:14(5):1164-72. doi: 10.1111/ajt.12671. Epub Apr. 11, 2014.
Lachenbruch, et al. Biomarkers and surrogate endpoints in renal transplantation: present status and considerations for clinical trial design. Am J Transplant. Apr. 2004:4(4):451-7.
Lee, et al. Fit-for-purpose method development and validation for successful biomarker measurement. Pharm Res. Feb. 2006;23(2):312-28. Epub Jan. 12, 2006.
Lerut, et al. Acute rejection in non-compliant renal allograft recipients: a distinct morphology, Clin Transplant. 2007; 21(3): 344-51.
Li, et al. A peripheral blood diagnostic test for acute rejection in renal transplantation. Am J Transplant, Oct. 2012;12(10):2710-8. doi: 10.1111/j.1600-6143.2012.04253.x.
Lipshutz, et al. High density synthetic oligonucleotide arrays. Nat Genet, Jan. 1999:21(1 Suppl):20-4.
Liu, et al. A model for random sampling and estimation of relative protein abundance in shotgun proteomics, Anal Chem. Jul. 15, 2004,76(14):4193-201.
Livak, et al. Oligonucleotides with fluorescent dyes at opposite ends provide a quenched probe system useful for detecting PCR product and nucleic acid hybridization, PCR Methods Appl. Jun. 1995;4(6):357-62.
Lockhart, et al. Expression monitoring by hybridization to high-density oligonucleotide arrays. Nat Biotechnol. Dec. 1996;14(13):1675-80.
Mannon, et al. Chronic rejection of mouse kidney allografts. Kidney Int. May 1999;55(5):1935-44.
Mas, et al., Establishing the molecular pathways involved in chronic allograft nephropathy for testing new noninvasive diagnostic markers. Transplantation. Feb. 27, 2007;83(4):448-57.
McCall, et al. Frozen robust multiarray analysis (fRMA). Biostatistics, Apr. 2010;11(2):242-53. doi: 10.1093/biostatistics/kxp059. Epub Jan. 22, 2010.
McCall, et al. Thawing Frozen Robust Multi-array Analysis (fRMA). BMC Bioinformatics, Sep. 16, 2011;12:369. doi: 10.1186/1471-2105-12-369.
Meier-Kriesche, et al. Lack of improvement in renal allograft survival despite a marked decrease in acute rejection rates over the most recent era. Am J Transplant. Mar. 2004;4(3):378-83.
Meier-Kriesche, et al. Survival improvement among patients with end-stage renal disease: trends over time for transplant recipients and wait-listed patients. J Am Soc Nephrol, Jun. 2001;12(6):1293-6.
Mengel, et al., Infiltrates in protocol biopsies from renal allografts, Am J Transplant. 2007; 7(2): 356-65.
Mengel, et al. SWOT analysis of Banff: strengths, weaknesses, opportunities and threats of the international Banff consensus process and classification system for renal allograft pathology, Am J Transplant. Oct. 2007;7(10):2221-6.
Miao, et al. Estimating Harrell's Optimism on Predictive Indices Using Bootstrap Samples. SAS Global Forum, San Francisco; 2013.
Moreso, et al. Early subclinical rejection as a risk factor for late chronic humoral rejection. Transplantation. 2012, 93(1): 41-6.
Moreso, et al. Subclinical rejection associated with chronic allograft nephropathy in protocol biopsies as a risk factor for late graft loss. Am J Transplant. Apr. 2006;6(4):747-52.
Morrissey, et al. Factors contributing to acute rejection in renal transplantation: the role of noncompliance. Transplant Proc. 2005; 37(5): 2044-7.
Nankivell, et al. Chronic allograft nephropathy: current concepts and future directions, Transplantation, Mar. 15, 2006;81(5):643-54.
Nankivell, et al. The natural history of chronic allograft nephropathy. N Engl J Med. Dec. 11, 2003;349(24):2326-33.
Nielsen, et al. Sequence-selective recognition of DNA by strand displacement with a thymine-substituted polyamide. Science, Dec. 6, 1991;254(5037):1497-500.

(56) References Cited

OTHER PUBLICATIONS

Oetting, et al. Urinary beta2-microglobulin is associated with acute renal allograft rejection. Am J Kidney Dis. May 2006;47(5):898-904.
PA. Power Atlas, 2007. Accessed Dec. 9, 2014 http://www.poweratlas.org/.
Pascual, et al. Chronic rejection and chronic cyclosporin toxicity in renal allografts. Immunol Today. Nov. 1998;19(11):514-9.
Pascual, et al. Strategies to improve long-term outcomes after renal transplantation. N Engl J Med. Feb. 21, 2002;346(8):580-90.
Racusen, et al. The Banff 97 working classification of renal allograft pathology. Kidney Int. Feb. 1999:55(2):713-23.
Robin, et al. pROC: an open-source package for R and S+ to analyze and compare ROC curves. BMC Bioinformatics, Mar. 17, 2011;12;77. doi: 10.1186/1471-2105-12-77.
Rush, et al. Subclinical rejection—a potential surrogate marker for chronic rejection—may be diagnosed by protocol biopsy or urine spectroscopy, Ann Transplant. 2000; 5(2): 44-9.
Sabek, et al. Quantitative detection of T-cell activation markers by real-time PCR in renal transplant rejection and correlation with histopathologic evaluation. Transplantation. Sep. 15, 2002;74(5):701-7.
Sadygov, et al. Code developments to improve the efficiency of automated MS/MS spectra interpretation. J Proteome Res. May-Jun. 2002;1(3):211-5.
Sarwal, et al. Molecular heterogeneity in acute renal allograft rejection identified by DNA microarray profiling. N Engl J Med. Jul. 10, 2003;349(2):125-38.
Schena, et al. Quantitative monitoring of gene expression patterns with a complementary DNA microarray, Science. Oct. 20, 1995;270(5235):467-70.
Schuab, et al. Proteomic-based identification of cleaved urinary beta2-microglobulin as a potential marker for acute tubular injury in renal allografts. Am J Transplant. Apr. 2005;5(4 Pt 1):729-38.
Schwarz, et al. Risk factors for chronic allograft nephropathy after renal transplantation: a protocol biopsy study, Kidney Int. 2005; 67(1): 341-8.
Shapiro, et al. An analysis of early renal transplant protocol biopsies—the high incidence of subclinical tubulitis. Am J Transplant. May 2001;1(1):47-50.
Shen, et al. Eigengene-based linear discriminant model for tumor classification using gene expression microarray data. Bioinformatics. Nov. 1, 2006;22(21):2635-42. Epub Aug. 22, 2006.
Simon, et al. Serial peripheral blood perforin and granzyme B gene expression measurements for prediction of acute rejection in kidney graft recipients. Am J Transplant. Sep. 2003;3(9):1121-7.
Sis, et al. Endothelial gene expression in kidney transplants with alloantibody indicates antibody-mediated damage despite lack of C4d staining. Am J Transplant. Oct. 2009;9(10):2312-23. doi: 10.1111/j.1600-6143.2009.02761.x. Epub Jul. 22, 2009.
Solez, et al. Banff '05 Meeting Report: differential diagnosis of chronic allograft injury and elimination of chronic allograft nephropathy ('CAN'). Am J Transplant, Mar. 2007;7(3):518-26.
Solez, et al. Banff 07 classification of renal allograft pathology: updates and future directions. Am J Transplant, Apr. 2008;8(4):753-60, doi: 10.1111/j.1600-6143.2008.02159.x. Epub Feb. 19, 2008.
Tabb, et al. DTASelect and Contrast: tools for assembling and comparing protein identifications from shotgun proteomics. J Proteome Res. Jan.-Feb. 2002;1(1):21-6.
Tibshirani, et al. Class prediction by nearest shrunken centroids with applications to DNA microarrays. Statist, Sci. vol. 18 (1): 104-117. (year 2003).
Tibshirani, et al. Diagnosis of multiple cancer types by shrunken centroids of gene expression. Proc Natl Acad Sci U.S.A. May 14, 2002;99(10):6567-72.
Tussen, P. Chapter 3 of Laboratory Techniques in Biochemistry and Molecular Biology: Hybridization With Nucleic Acid Probes, Part 1. Theory and Nucleic Acid Preparation, Elsevier, N.Y. 1993.
U.S. Department of Health and Human Services. OPTN/SRTR Annual Report. Source: OPTN/SRTR Data as of May 4, 2009. http://www.ustransplant.org/annual_reports/current/509a_ki.htm.
Washburn, et al. Large-scale analysis of the yeast proteome by multidimensional protein identification technology. Nat Biotechnol. Mar. 2001;19(3):242-7.
Wiebe, et al. Evolution and clinical pathologic correlations of de novo donor-specific HLA antibody post kidney transplant. Am J Transplant. May 2012;12(5):1157-67. doi: 10.1111/j.1600-6143.2012.04013.x. Epub Mar. 19, 2012.
Woolf, SH. Screening for prostate cancer with prostate-specific antigen. An examination of the evidence. N Engl J Med. Nov. 23, 1995:333(21):1401-5.
Yates, et al. The aetiology and pathogenesis of chronic allograft nephropathy, Transpl Immunol. Nov. 2006;16(3-4):148-57. Epub Nov. 2, 2006.
Yilmaz, et al. Evaluating the accuracy of functional biomarkers for detecting histological changes in chronic allograft nephropathy. Transpl Int. Jul. 2007;20(7):608-15. Epub May 22, 2007.
Yilmaz, et al. Protocol core needle biopsy and histologic Chronic Allograft Damage Index (CADI) as surrogate end point for long-term graft survival in multicenter studies. J Am Soc Nephrol, Mar. 2003;14(3):773-9.
Zhu, et al. Network-based support vector machine for classification of microarray samples. BMC Bioinformatics. Jan. 30, 2009;10 Suppl I:S21. doi: 10.1186/1471-2105-10-S1-S21.
Anglicheau; et al. Noninvasive prediction of organ graft rejection and outcome using gene expression patterns. Transplantation. Jul. 27, 2008;86(2):192-9. doi: 10.1097/TP.0b013e31817eef7b.
Cardinale; et al. Transcriptome profiling of human ulcerative colitis mucosa reveals altered expression of pathways enriched in genetic susceptibility loci. PLoS One. May 1, 2014;9(5):e96153. doi: 10.1371/journal.pone.0096153. eCollection 2014.
Co-pending U.S. Appl. No. 15/358,390, filed Nov. 22, 2016.
International search report and written opinion dated Oct. 19, 2015 for PCT Application No. US2015/032191.
International search report and written opinion dated Oct. 26, 2015 for PCT Application No. US2015/032195.
International search report and written opinion dated Nov. 4, 2015 for PCT Application No. US2015/032202.
Levitsky; et al. Clinical and plasma proteomic markers correlating with chronic kidney disease after liver transplantation. Am J Transplant. Sep. 2011;11(9):1972-8. doi: 10.1111/j.1600-6143.2011.03669.x. Epub Jul. 27, 2011.
Mueller, et al. Assessment of kidney organ quality and prediction of outcome at time of transplantation. 2011. Semin Immunopathol. vol. 33, pp. 185-199.
Office Action dated Jan. 9, 2017 for U.S. Appl. No. 14/481,167.
Office Action dated Jun. 15, 2016 for U.S. Appl. No. 14/481,167.
Co-pending U.S. Appl. No. 15/313,215, filed Nov. 22, 2016.
Co-pending U.S. Appl. No. 15/313,217, filed Nov. 22, 2016.

* cited by examiner

GENE EXPRESSION PROFILES ASSOCIATED WITH CHRONIC ALLOGRAFT NEPHROPATHY

CROSS-REFERENCE TO RELATED APPLICATIONS

The present application is a continuation of U.S. patent application Ser. No. 16/803,337 (filed Feb. 27, 2020; now allowed) which is a continuation of U.S. patent application Ser. No. 15/666,920 (filed Aug. 2, 2017), which is a continuation of U.S. patent application Ser. No. 13/261,130 (filed Mar. 20, 2012; now issued as U.S. Pat. No. 9,752,191), which is a national stage application of International Application No. PCT/US2010/041598 (filed Jul. 9, 2010), which claims the benefit of priority to U.S. Provisional Patent Application No. 61/224,328 (filed Jul. 9, 2009) and U.S. Provisional Patent Application No. 61/224,317 (filed Jul. 9, 2009). The full disclosures of the priority applications are incorporated herein by reference in their entirety and for all purposes.

STATEMENT OF GOVERNMENT LICENSE RIGHTS

The invention was made with government support under AI063603, AI084146 and AI052349 awarded by the National Institutes of Health. The government has certain rights in the invention.

BACKGROUND OF THE INVENTION

Kidney transplantation offers a significant improvement in life expectancy and quality of life for patients with end stage renal disease[1]. Unfortunately, a chronic, progressive allograft dysfunction of uncertain etiology continues to be a primary cause of graft loss[2,3]. There has been some evolution of terminology for describing the histological basis of this chronic, progressive nephropathy, which is still commonly referred to as chronic allograft nephropathy (CAN) and more recently as interstitial fibrosis and tubular atrophy (IFTA)[4-6]. In current practice CAN refers to a clinical entity of a chronic progressive loss of kidney transplant function associated with a rising serum creatinine and a falling creatinine clearance. In current practice, IFTA refers to the histological findings based on review of a kidney transplant biopsy. Immunologic factors linked to CAN/IFTA are acute, sub-clinical and CAN/IFTA, HLA mismatching and circulating donor-specific anti-HLA antibodies[7,8]. Non-immunologic factors include hypertension, chronic toxicity of calcineurin inhibitors, hyperfiltration and diabetes mellitus[9-12]. The unifying mechanism is thought to be a progressive cycle of vascular and tissue injury, incomplete repair, compensatory hypertrophy, progressive interstitial fibrosis and nephron loss[13]. Moreover, increasing evidence is suggesting that the primary mechanism of CAN/IFTA is a chronic immunological injury mediated by a combination of T cell and antibody-mediated immunity, in other words, chronic rejection.

As early as two years post kidney transplant, protocol biopsies have shown that more than 50% of recipients have mild CAN/IFTA[2,15,16] and by 10 years over 50% of kidney transplant recipients have severe CAN/IFTA that is associated with diminishing graft function[2]. Traditional kidney function measurements like serum creatinine and glomerular filtration rates used to predict CAN/IFTA have poor predictive values[17] and a diagnosis requires a transplant biopsy[18,19]. Predicting graft outcomes strictly based on the kidney biopsy is difficult and this invasive procedure has significant costs and risks for patients. Thus, there is a pressing medical need to identify minimally invasive biomarkers that are able to identify early stages of CAN/IFTA at a time that changes in therapy may alter outcomes.

Rapidly evolving technologies for genomics have created new opportunities to develop minimally invasive biomarkers. Recent studies, including our own, have reported genes that are differentially expressed at the mRNA level in kidney biopsies in the presence of CAN/IFTA[16,20,21]. The limitation of these studies is that they require an invasive transplant biopsy. Others have reported analyzing urine and peripheral blood using RT-qPCR or proteomics to identify small numbers of potential biomarkers for CAN/IFTA, though none is validated for clinical use[22,23].

BRIEF SUMMARY OF THE INVENTION

The invention provides methods of prognosing, diagnosing or monitoring chronic allograft nephropathy and/or interstitial fibrosis and tubular atrophy (CAN/IFTA). The methods entail (a) determining expression levels in a subject of at least 5 genes selected from the genes in Table A, B, C, D, E, F, G, H, I and/or J; and (b) prognosing diagnosing or monitoring CAN/IFTA in a subject from the expression levels. Optionally, for each of the at least five genes, step (b) comprises comparing the expression level of the gene in the subject to one or more reference expression levels of the gene associated with CAN/IFTA or lack of CAN/IFTA. Optionally, step (b) further comprises for each of the at least five genes assigning the expression level of the gene in the subject a value or other designation providing an indication whether the subject has or is at risk of CAN/IFTA. Optionally, the expression level of each of the at least five genes is assigned a value on a normalized scale of values associated with a range of expression levels in kidney transplant patients with and without CAN/IFTA. Optionally, the expression level of each of the at least five genes is assigned a value or other designation providing an indication that the subject has is at risk of CAN/IFTA, lacks and is not at risk of CAN/IFTA, or that the expression level is uninformative. Optionally, step (b) further comprises, combining the values or designations for each of the genes to provide a combined value or designation providing an indication whether the subject has or is at risk of CAN/IFTA. Optionally, the method is repeated at different times on the subject.

In some methods, the subject is receiving a drug, and a change in the combined value or designation over time provides an indication of the effectiveness of the drug. Optionally, the subject has undergone a kidney transplant within 1-10 years of performing step (a). Optionally, step (a) is performed on a blood sample of the subject. Optionally, the blood sample is a plasma sample. Optionally, step (a) is performed on at least ten, 20, 40, or 100 genes from Table A, B, C, D, E, F, G, H, I and/or J.

Some methods further comprise changing the treatment regime of the patient responsive to the prognosing, diagnosing or monitoring step. In some methods, the subject has received a drug before performing the methods, and the change comprises administering an additional drug or administering a higher dose of the same drug. Some methods, further comprise performing an additional procedure, such as a kidney biopsy, to detect CAN/IFTA or risk thereof if the determining step provides an indication the subject has or is at risk of CAN/IFTA.

In some methods, the at least five genes are from Table A, B, C and/or D expression levels are determined at the mRNA level. In some methods, the at least five genes are from Tables E, F, G, H, I, and/or J and expression levels are determined at the protein level. In some methods, step (b) is performed by a computer. In some methods, the at least five genes are selected from Tables C and D. In some methods, the at least five genes are selected from Table C. In some methods, the at least five genes are selected from Table D. In some methods, the at least five genes are selected from Table E and F or H and I and expression levels are determined at the protein level.

The invention further provides an array, comprising a support or supports bearing a plurality of nucleic acid probes complementary to a plurality of mRNAs fewer than 5000 in number, wherein the plurality of mRNAs includes mRNAs expressed by at least five genes selected from Tables A, B, C, D. Optionally, the plurality of mRNAs are fewer than 1000, or 100 in number. Optionally a plurality of nucleic acid probes are attached to a planar support or to beads. Optionally, the at least five genes are selected from Table C and D. Optionally, the at least five genes are selected from Table C. Optionally, the at least five genes are selected from Table D.

The invention further provides an array, comprising a support or supports bearing a plurality of ligands that specifically bind to a plurality of proteins fewer than 5000 in number, wherein the plurality of proteins includes at least five proteins selected from Tables E, F, G, H, I and/or J. Optionally, the plurality of proteins are fewer than 1000 or 100 in number. Optionally, the plurality of ligands are attached to a planar support or to beads. Optionally, the at least five proteins are selected from Tables E and F and/or I and J. Optionally, the ligands are different antibodies, wherein the different antibodies bind to different proteins of the plurality of proteins.

The invention further provides a method of expression analysis, comprising determining expression levels of up to 5000 genes in a sample from a subject having a kidney transplant, wherein the genes include at least 5 genes selected from Table A, B, C, D, E, F, G, H, I and/or J. Optionally, the expression levels of up to 1000 or 100 genes are determined. The expression levels can be determined at the mRNA or protein level. The levels can be determined by, for example, quantitative PCR or hybridization to an array.

The invention further provides methods of screening a compound for activity in inhibiting or treating CAN/IFTA. The methods entail (a) administering the compound to a subject having or at risk of CAN/IFTA; (b) determining expression levels of at least five genes in the subject selected from Table A, B, C, D, E, F, G, H, I, and/or J and species variants thereof before and after administering the drug to the subject, and (c) determining whether the compound has activity in inhibiting or treating CAN/IFTA from a change in expression levels of the genes after administering the compound. Optionally, step (c) comprises for each of the at least five changes assigning a value or designation depending on whether the change in the expression level of the gene relative to one or more reference levels indicating presence or absence of CAN/IFTA. Optionally, the method further comprises determining a combined value or designation for the at least five genes from the values or designations determined for each gene. Optionally, the subject is human or a nonhuman animal model of CAN/IFTA.

The invention further provides methods of subtyping CAN/IFTA. The methods entail (a) determining expression levels in a subject of at least 5 genes selected from the genes in Tables A, B, C, D; E, F, G, H, I and/or J; and (b) determining a subtype of CAN/IFTA from the expression levels. The subtype can be selected from the group consisting of stage 0, 1, 2, or 3 of CAN/IFTA. Optionally, the subtype is stage 0, stage 1 or stage 2 and/or 3. In some methods for each of the at least five genes, step (b) comprises comparing the expression level of the gene in the subject to one or more reference expression levels of the gene associated with the subtype of CAN/IFTA or lack of CAN/IFTA. Some methods further comprise for each of the at least five genes assigning the expression level of the gene in the subject a value or other designation providing an indication whether the subject has or is at risk of the subtype of CAN/IFTA. In some methods, the expression level of each of the at least five genes is assigned a value on a normalized scale of values associated with a range of expression levels in kidney transplant patients with the subtype and without CAN/IFTA. In some methods, the expression level of each of the at least five genes is assigned a value or other designation providing an indication that the subject has or is at risk of the subtype of CAN/IFTA, lacks and is not at risk of the subtype of CAN/IFTA, or that the expression level is uninformative. In some methods, step (b) further comprises, combining the values or designations for each of the genes to provide a combined value or designation providing an indication whether the subject has or is at risk of the subtype of CAN/IFTA. Some methods are repeated at different times on the subject. In some methods, the subject is receiving a drug, and a change in the combined value or designation over time provides an indication of the effectiveness of the drug. In some methods, the subject has undergone a kidney transplant within 1-10 years of performing step (a). Some methods are performed on a blood sample of the subject, such as a plasma or whole blood sample. Some methods are performed on at least ten, 20, 40 or 100 genes selected from Tables A, B, C, D, E, F, G, H, I and/or J. Some methods further comprise changing the treatment regime of the patient responsive to the whether the subtype is present. In some methods, the subject has received a drug before performing the methods, and the change comprises administering an additional drug or administering a higher dose of the same drug. Some methods further comprise performing an additional procedure, such as a kidney biopsy, to detect CAN/IFTA or risk thereof if the determining step provides an indication the subject has or is at risk of the subtype of CAN/IFTA. Expression levels can be determined at the mRNA or protein level. In some methods, step (b) is performed by a computer. In some methods, the at least five genes are selected from Table C. In some methods, the at least five genes are selected from Table D. In some methods, the at least five genes are selected from Table E and expression levels are determined at the protein level. In some methods, the at least five genes are selected from Table F and the expression levels are determined at the protein level. In some methods, the at least five genes are selected from Table H and the expression levels are determined at the protein level. In some methods, the at least five genes are selected from Table I and the expression levels are determined at the protein level.

DEFINITIONS

Figure 1:
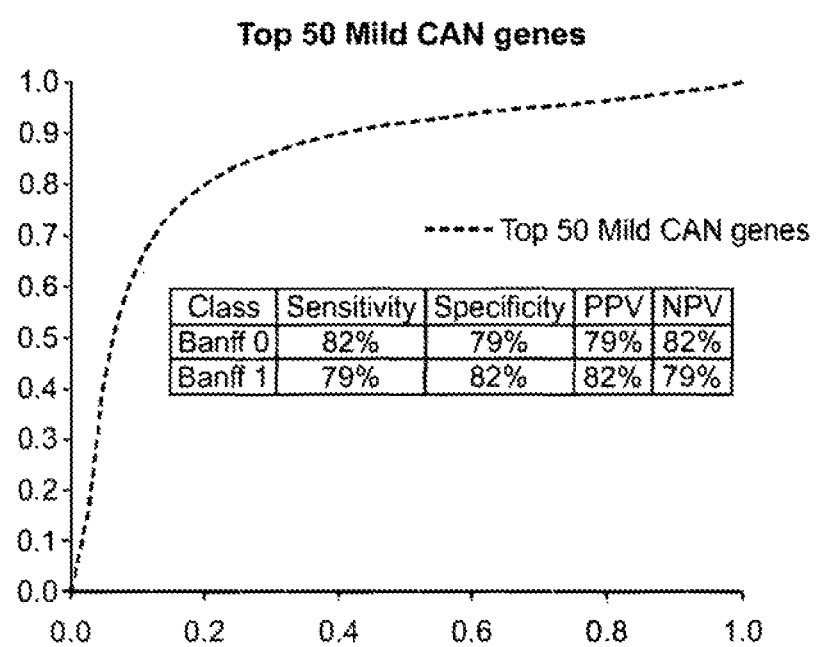
FIG. 1: Class prediction analysis of Banff 0 vs. Banff 1 (mild CAN/IFTA) based on Diagonal Linear Discriminant Analysis for the top 50 Banff 0 vs. Banff 1 consensus genes ranked by p values. A) depicts the Receiver Operating Characteristic (ROC) curves and provides the Sensitivity, Specificity, Positive Predictive Value (PPV) and Negative Predictive Value (NPV)

The term Chronic Allograft Nephropathy/Interstitial Fibrosis and Tubular Atrophy (CAN/IFTA) refers to a progressive, chronic, kidney tissue injury that eventually causes a progressive, chronic deterioration of kidney transplant function. The histological changes of CAN/IFTA can be found in protocol kidney transplant biopsies as early as 6 months post transplant and frequently the clinical changes of progressive kidney transplant dysfunction evolve subsequently over the next year or several years (e.g., six months to ten years). CAN/IFTA is usually a consequence of combined immunological injury (e.g. chronic rejection) and non-immunological damage (e.g. hypertensive nephrosclerosis, or nephrotoxicity of immunosuppressants like cyclosporine A), taking place months or years after transplantation and ultimately leading to histologically detectable fibrosis and sclerosis of the transplant and progressive loss of kidney function. Chronic rejection of a transplanted kidney is increasingly thought to be the major mechanism of CAN/IFTA mediated through both T cell mediated immunity and antibodies directed at antigens expressed in the kidney transplant. The hybrid term, CAN/IFTA includes histological changes and/or functional deterioration of the kidneys or both. In some patients, the present methods can provide an indication of histological changes before detectable functional deterioration of the kidneys has occurred, thereby allowing early therapeutic intervention.

Transplantation is the transfer of tissues, cells or an organ from a donor into a recipient. If the donor and recipient as the same person, the graft is referred to as an autograft and as is usually the case between different individuals of the same species an allograft. Transfer of tissue between species is referred to as a xenograft.

A biopsy is a specimen obtained from a living patient for diagnostic evaluation. Kidney biopsies can be obtained with a needle.

An average value can refer to any of a mean, median or mode.

A gene expression level is associated with a particular phenotype e.g., presence of CAN/IFTA or a subtype thereof if the gene is differentially expressed in a patient having the phenotype relative to a patient lacking the phenotype to a statistically significant extent. Unless otherwise apparent from the context a gene expression level can be measured at the mRNA and/or protein level.

A target nucleic acids is a nucleic acid (often derived from a biological sample), to which a polynucleotide probe is designed to specifically hybridize. The probe can detect presence, absence and/or amount of the target. The term can refer to the specific subsequence of a larger nucleic acid to which the probe is directed or to the overall sequence (e.g., c DNA or mRNA) whose expression level it is desired to detect.

The term subject or patient can include human or non-human animals. Thus, the methods and described herein are applicable to both human and veterinary disease and animal models. Preferred subjects are "patients," i.e., living humans that are receiving medical care for a disease or condition. This includes persons with no defined illness who are being investigated for signs of pathology.

Diagnosis refers to methods of estimating or determining whether or not a patient is suffering from a given disease or condition or severity of the condition. Diagnosis does not require ability to determine the presence or absence of a particular disease with 100% accuracy, or even that a given course or outcome is more likely to occur than not. Instead, the "diagnosis" refers to an increased probability that a certain disease or condition is present in the subject compared to the probability before the diagnostic test was performed.

Similarly, a prognosis signals an increased probability that a given course or outcome will occur in a patient relative to the probability before the prognostic test.

A probe or polynucleotide probe is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe can include natural (i.e., A, G, C, or T) or modified bases (e.g., 7-deazaguanosine, inosine). A probe can be an oligonucleotide which is a single-stranded DNA. Polynucleotide probes can be synthesized or produced from naturally occurring polynucleotides. In addition, the bases in a probe can be joined by a linkage other than a phosphodiester bond, so long as it does not interfere with hybridization. Thus, probes can include, for example, peptide nucleic acids in which the constituent bases are joined by peptide bonds rather than phosphodiester linkages (see, e.g., Nielsen et al., Science 254, 1497-1500 (1991)). Some probes can have leading and/or trailing sequences of noncomplementarity flanking a region of complementarity.

A perfectly matched probe has a sequence perfectly complementary to a particular target sequence. The probe is typically perfectly complementary to a portion (subsequence) of a target sequence. The term "mismatch probe" refer to probes whose sequence is deliberately selected not to be perfectly complementary to a particular target sequence.

The term "isolated," "purified" or "substantially pure" means an object species (e.g., a nucleic acid sequence described herein or a polypeptide encoded thereby) has been at least partially separated from the components with which it is naturally associated.

Differential expression refers to a statistically significant difference in expression levels of a gene between two populations of samples (e.g., samples with and without CAN/IFTA). The expression levels can differ for example by at least a factor of 1.5 or 2 between such populations of samples. Differential expression includes genes that are expressed in one population and are not expressed (at least at detectable levels) in the other populations. Unique expression refers to detectable expression in one population and undetectable expression (i.e., insignificantly different from background) in the other population using the same technique (e.g., as in the present example for detection).

Control populations for comparison with populations undergoing CAN/IFTA are usually referred to as being without CAN/IFTA. Unless otherwise indicated, such a control population also means subjects without acute kidney rejection.

Hybridization reactions are preferably performed under stringent conditions in which probes or primers hybridize to their intended target with which they have perfect complementarity and not to or at least to a reduced extent to other targets. An example of stringent hybridization conditions are hybridization in 6× sodium chloride/sodium citrate (SSC) at about 45° C., followed by one or more washes in 0.2×SSC, 0.1% SDS at 50° C., 55° C., 60° C., and even more or 65° C.

Statistical significance means $p<0.05$ or $<0.01$ or even $<0.001$ level.

DETAILED DESCRIPTION OF THE INVENTION

I. General

By a genome-wide gene analysis of expression profiles of over 50,000 known or putative gene sequences in peripheral blood, the present inventors have identified consensus sets of gene expression-based molecular biomarkers associated with CAN/IFTA. A set of 393 genes has differential expression levels between mild chronic allograft nephropathy (CAN/IFTA) and non-rejected transplants. A set of 63 genes have differential expression between moderate or severe CAN/IFTA and non-rejected transplants. Additional set of protein markers showing differential or unique expression between CAN/IFTA and non rejected transplants are also provided.

II. Genes in Profiles

Table A lists 393 genes whose expression changes significantly between kidney transplant patients undergoing mild CAN/IFTA, Banff stage 1 compared with patients not undergoing such rejection (Banff stage 0) one year post transplant. The columns in the table have the following meanings: column 1 is a number assigned to a gene, column 2 is a measure of the statistical significance of change in gene expression between the above populations, column 3 is a mean expression level of a gene in kidney transplant patients undergoing chronic rejection (normalized as described below), column 4 is mean expression level of the gene in kidney transplant patients not undergoing CAN/IFTA (similarly normalized), column 5 is a ratio of the expression levels, column 6 is an Affymetrix number indicating a set of probes suitable for measuring expression of the gene, column 7 is a gene name (recognized names of HUGO or similar bodies are used when available), and column 8 is a further description of the gene. Table B provides similar information for 62 genes that show differential expression between kidney transplant patients undergoing moderate or severe CAN/IFTA (Banff stage 2 or 3) with kidney transplant patients not undergoing CAN/IFTA. Tables C and D provide subsets of 50 preferred genes from Tables A and B respectively.

Table E provides 117 genes and corresponding proteins for which the proteins is uniquely expressed in patients not undergoing CAN/IFTA and not at detectable levels in patients undergoing CAN/IFTA level 1. Column 1 is a sequential number for a gene/protein, column 2 is a protein symbol, column 3 is a gene symbol, and column 4 is a gene name. Table F provides similar information about 143 proteins uniquely expressed in patients undergoing CAN/IFTA and not at detectable levels in kidney transplant patients without CAN/IFTA. Table G provides similar information regarding 188 proteins that are differentially expressed between CAN/IFTA levels 0 and 1. The right hand column of the table indicates the degree of differential expression with positive numbers being upregulated in Banff stage 1 patients. Table H provides similar information to Table E for 28 genes uniquely expressed in kidney transplant patients not undergoing CAN/ITFA and not at detectable levels in patients undergoing CAN/IFTA level 2 or 3. Table I provides similar information to Table F for 510 proteins uniquely expressed in CAN/IFTA level 2 or 3 and not detectable in kidney transplant patients not undergoing CAN/IFTA. Table J provides similar information to Table G for 284 proteins differentially expressed between kidney transplant patients at CAN/IFTA level 0 versus level 2 or 3. If a gene symbol or gene name is not available, the protein symbol should be understood as referring to both the genes.

The genes referred to in the above tables are human genes. In some methods, species variants or homologs of these genes are used in a non-human animal model. Species variants are the genes in different species having greatest sequence identity and similarity in functional properties to one another. Many species variants of the above human genes are listed in the Swiss-Prot database.

Raw gene expression levels are comparable between different genes in the same sample but not necessarily between different samples. As noted above, values given for gene expression levels can be normalized so that values for particular genes are comparable within and between the populations being analyzed. The normalization eliminates or at least reduces to acceptable levels any sample to sample differences arising from factors other than CAN/IFTA (e.g. differences in overall transcription levels of patients due to general state of health and differences in sample preparation or nucleic acid amplification between samples). The normalization effectively applies a correction factor to the measured expression levels from a given array such that a profile of many expression levels in the array are the same between different patient samples. Software for normalizing overall expression patterns between different samples is both commercially and publically available (e.g., XRAY from Biotique Systems or BRB ArrayTools from the National Cancer Institute). After applying appropriate normalizing factors to the measured expression value of a particular gene in different samples, an average value of the expression level is determined for the samples in a population. The average values between different populations are then compared to determine whether expression level has changed significantly between the populations. The changes in expression level indicated for a given gene represent the relative expression level of that gene in samples from a population of individuals with a defined condition (e.g., transplant patients with CAN/IFTA of specified Banff stage) relative to samples from a control population (kidney transplant patients not undergoing CAN/IFTA). Similar principles apply in normalizing gene expression levels at the mRNA and protein levels. Comparisons between populations are made at the same level (e.g., mRNA levels in one population are compared with mRNA levels in another population or protein levels in one population with protein levels in another population).

III. Subject Population

The methods are particularly useful on human subjects who have undergone a kidney transplant although can also be used on subjects who have gone other types of transplant (e.g., heart, liver, lungs, stem cell) or on non-humans who have undergone kidney or other transplant. Gene expression levels in such subjects can be measured, for example, within, three months, six months, one year, two years, five years or ten years after a kidney transplant In some methods, gene expression levels are determined at regular intervals, e.g., every 3 months, 6 months or every year posttransplant, either indefinitely, or until evidence of CAN/IFTA is observed, in which case the frequency of monitoring is sometimes increased. In some methods, baseline values of expression levels are determined in a subject before a kidney transplant in combination with determining expression levels at one or more time points thereafter. In other methods, a measurement is initiated responsive to some other indication of potential kidney impairment, such as a rise in levels of creatinine or BUN or a decrease in glomerular filtration rate. Similar methods can be practiced in non-human species, in which cases, the expression levels measured are the species equivalent of the human genes referenced above.

IV. Chronic Allograft Nephropathy (CAN/IFTA) and its Subtypes

The methods are particularly useful for detecting CAN/IFTA. CAN/IFTA can be further classified by histological analysis of kidney transplant biopsies based on the Banff 2007 schema and the following four subtypes or stages are recognized indicating severity: 0 (no CAN/IFTA), 1 (mild CAN/IFTA), 2 (moderate CAN/IFTA) and 3 (severe CAN/IFTA) [4]. An alternative and complementary histology grading schema is the Chronic Allograft Damage Index (CADI) score and this score is often provided by pathologists with the Banff classification score as supplemental information (for example, see Yilmaz et al, J Am Soc Nephrol 2003 14: 773-779). There is also a Banff 2007 classification for acute rejection [4]. Acute rejection is characterized histologically by an active, inflammatory/immune cell infiltration comprised of various numbers of T cells and B cells as well as sometimes plasma cells, eosinophils, neutrophils and macrophages.

V. Methods of Measuring Profiles

The preferred sample type for analysis is a blood sample, which refers to whole blood or fractions thereof, such as plasma, or lymphocytes. Other samples that can be analyzed include urine, feces, saliva, and a kidney biopsy. The samples are typically isolated from a subject, particularly as a peripheral blood sample, and not returned to the subject. The analytes of interests in the samples can be analyzed with or without further processing of the sample, such as purification and amplification. Samples not requiring biopsy to obtain, particularly peripheral blood, are preferred.

Expression profiles are preferably measured at the nucleic acid level, meaning that levels of mRNA or nucleic acid derived therefrom (e.g., cDNA or cRNA). An expression profile refers to the expression levels of a plurality of genes in a sample. A nucleic derived from mRNA means a nucleic acid synthesized using mRNA as a template. Methods of isolation and amplification of mRNA are well known as described for example WO 97/10365, WO 97/27317, Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993). If mRNA or a nucleic acid therefrom is amplified, the amplification is performed under conditions that approximately preserve the relative proportions of mRNA in the original samples, such that the levels of the amplified nucleic acids can be used to establish phenotypic associations representative of the mRNAs.

A variety of approaches are available for determining mRNA levels including probe arrays and quantitative PCR. A number of distinct array formats are available. Some arrays, such as an Affymetrix GeneChip® array, have different probes occupying discrete known areas of a contiguous support. Other arrays, such as arrays from Illumina, have different probes attached to different particles or beads. In such arrays, the identity of which probe is attached to which particle or beads is usually determinable from an encoding system. The probes can be oligonucleotides. In such case, typically several match probes are included with perfect complementarity to a given target mRNA together, optionally together with mismatch probes differing from the match probes are a known number of oligonucleotides (Lockhart, et al., Nature Biotechnology 14:1675-1680 (1996); and Lipschutz, et al., Nature Genetics Supplement 21: 20-24, 1999). Other arrays including full length cDNA sequences with perfect or near perfect complementarity to a particular cDNA (Schena et al. (Science 270:467-470 (1995); and DeRisi et al. (Nature Genetics 14:457-460 (1996)). Such arrays can also include various control probes, such as a probe complementarity with a house keeping gene likely to be expressed in most samples. Regardless of the specifics of array design, an array contains one or more probes either perfectly complementary to a particular target mRNA or sufficiently complementary to the target mRNA to distinguish it from other mRNAs in the sample, and the presence of such a target mRNA can be determined from the hybridization signal of such probes, optionally by comparison with mismatch or other control probes included in the array. Typically, the target bears a fluorescent label, in which case hybridization intensity can be determined by, for example, a scanning confocal microscope in photon counting mode. Appropriate scanning devices are described by e.g., U.S. Pat. Nos. 5,578,832, and 5,631,734. The intensity of labeling of probes hybridizing to a particular mRNA or its amplification product provides a raw measure of expression level.

In other methods, expression levels are determined by so-called "real time amplification" methods also known as quantitative PCR or Taqman (see, e.g., U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995)). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified. mRNA levels can also be measured without amplification by hybridization to a probe, for example, using a branched nucleic acid probe, such as a QuantiGene® Reagent System from Panomics.

Alternatively or additionally, expression levels of genes can be determined at the protein level, meaning that levels of proteins encoded by the genes discussed above are measured. Several methods and devices are well known for determining levels of proteins including immunoassays such as described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. These assays include various sandwich, competitive, or non-competitive assay formats, to generate a signal that is related to the presence or amount of an protein analyte of interest. Any suitable immunoassay may be utilized, for example, lateral flow, enzyme-linked immunoassays (ELISA), radioimmunoassays (RIAs), competitive binding assays, and the like. Numerous formats for antibody arrays have been described proposed employing antibodies. Such arrays typically include different antibodies having specificity for different proteins intended to be detected. For example, usually at least one hundred different antibodies are used to detect one hundred different protein targets, each antibody being specific for one target. Other ligands having specificity for a particular protein target can also be used, such as the synthetic antibodies disclosed in WO/2008/048970. Other compounds with a desired binding specificity can be selected from random libraries of peptides or small molecules. U.S. Pat. No. 5,922,615 describes a device that utilizes multiple discrete zones of immobilized antibodies on membranes to detect multiple target antigens in an array. U.S. Pat. Nos. 5,458,852, 6,019,944, 6,143,576. Microtiter plates or automation can be used to facilitate detection of large numbers of different proteins. Protein levels can also be determined by mass spectrometry as described in the examples.

The selection of genes for determination of expression levels depends on the particular application (e.g., analysis of CAN/IFTA in general or one of the subtypes described above). In general, the genes are selected from one of the tables indicated above as appropriate for the application. In some methods, expression levels of at least 2, 3, 4, 5, 10, 20, 25, 50, 100, 150, 250 (e.g. 100-250) genes shown in any of Table A, B, C or D are determined. In some methods, expression levels of at least 2, 3, 4, 5, 10, 20, 25, 50, 100, 150, 250 or all genes shown in Table A are determined and/or expression levels of 2, 3, 4, 5, 10, 20, 25, 50 or all genes shown in Table B are determined. In some methods, expression levels of at least 2, 3, 4, 5, 10, 20, 25, or all 50 genes in Table C and at least 2, 3, 4, 5, 10, 20, 25, or all 50 genes in Table D are determined. In some methods, expression levels of 2, 3, 4, 5, 10, 20, 25, 50 or all genes shown in Tables 2, 3, 4, 5 and/or 6 are determined (genes for which both mRNAs and proteins are differentially expressed). In some methods, all genes are from the same table (i.e., all genes with differential expression associated with mild CAN/IFTA). In some methods, genes from different tables (i.e., including genes associated with mild CAN/IFTA and moderate/severe CAN/IFTA) are tested. In some methods, genes are selected such that genes from several different pathways are represented (e.g., at least one gene from at least 2, 3, 5, or 10 pathways, such as those described in the Examples). The genes within a pathway tend to be expressed in a co-ordinated expression whereas genes from different pathways tend to be expressed more independently. Thus, changes in expression based on the aggregate changes of genes from different pathways can have greater statistical significance than aggregate changes of genes within a pathway.

In some methods, expression levels of at least 2, 3, 4, 5, 10, 20, 25, 50, 100, or 150 proteins or corresponding genes shown in any of Tables E, F, G, H, I and/or J are determined. In some methods, expression levels of at least 2, 3, 4, 5, 10, 20, 25, 50, 100, 150 or all proteins or genes shown in Table E, F, and/or G are determined and/or expression levels of 2, 3, 4, 5, 10, 20, 25, 50 or all proteins or genes shown in Tables H, I and/or J are determined. In some methods, proteins or genes are selected from the same table (e.g., proteins uniquely expressed in Banff stage 1, or corresponding genes). In some methods, proteins or genes are selected from two tables (e.g., proteins uniquely expressed in Banff stage 0 (or corresponding genes) and proteins uniquely expressed in Banff stage 1 (or corresponding genes). In some methods, proteins or genes are selected from three tables (e.g., proteins uniquely expressed in Banff stage 0 or corresponding genes, proteins uniquely expressed in Banff stage 1 and corresponding genes, and proteins differentially expressed between Banff stages 1 and 0. Analogous selections of proteins can be made from Tables H-J for purposes of distinguishing Banff stages 0 and 2/3. In some methods, proteins or corresponding genes are selected such that proteins from several different pathways are represented (e.g., at least one gene from at least 2, 3, 5, or 10 pathways, such as those described in the Examples).

Expression levels of the present genes and/or proteins can be combined with or without determination of expression levels of any other genes or proteins of interest (e.g., genes or proteins associated with rejection of kidneys or other organs in WO 2007/104537, WO 2009/060035), Anglicheau et al., PNAS 106, 5330-5335 (2009)) and references, 16, 20, 21, 22, 23, 25, 26, 37 and 39. In some methods, the gene is not DPYD or IRS2 or the method includes determining the expression level of at least 5, 10, 25 or 50 genes other than DPYD and IRS2.

Regardless of the format adopted, the present methods can (but need not) be practiced by detection expression levels of a relatively small number of genes or proteins compared with the whole genome level expression analysis described in the Examples. In some methods, the total number of genes whose expression levels are determined is less than 5000, 1000, 500, 200, 100, 50, 25, 10, 5 or 3. In some methods, the total number of genes whose expression level is determined is 100-1500, 100-250, 500-1500 or 750-1250. In some methods, the total number of proteins whose expression levels are determined is less than 5000, 1000, 500, 200, 100, 50, 25, 10, 5 or 3. In some methods, the total number of proteins whose expression level is determined is 100-1500, 100-250, 500-1500 or 750-1250. Correspondingly, when an array form is used for detection of expression levels, the array includes probes or probes sets for less than 5000, 1000, 500, 200, 100, 50, 25, 10, 5 or 3 genes. Thus, for example, an Affymetrix GeneChip® expression monitoring array contains a set if about 20-50 oligonucleotide probes (half match and half-mismatch) for monitoring each gene of interest. Such an array design would include less than 5000, 1000, 500, 200, 100, 50, 25, 10, 5 or 3 such probes sets for detecting less than 5000, 1000, 500, 200, 100, 50, 25, 10, 5 or 3 genes. By further example, an alternative array including one cDNA for each gene whose expression level is to be detected would contain less than 5000, 1000, 500, 200, 100, 50, 25, 10, 5 or 3 such cDNAs for analyzing less than 5000, 1000, 500, 200, 100, 50, 25, 10, 5 or 3 genes. By further example, an array containing a different antibody for each protein to be detected would containing less than 5000, 1000, 500, 200, 100, 50, 25, 10, 5 or 3 different antibodies for analyzing less than 5000, 1000, 500, 200, 100, 50, 25, 10, 5 or 3 gene products.

VI. Analysis of Expression Levels

Analysis of expression levels initially provides a measurement of the expression level of each of several individual genes. The expression level can be absolute in terms of a concentration of an expression product, or relative in terms of a relative concentration of an expression product of interest to another expression product in the sample. For example, relative expression levels of genes can be expressed with respect to the expression level of a housekeeping gene in the sample. Relative expression levels can also be determined by simultaneously analyzing differentially labeled samples hybridized to the same array. Expression levels can also be expressed in arbitrary units, for example, related to signal intensity.

The individual expression levels, whether absolute or relative, can be converted into values or other designations providing an indication of presence or risk of CAN/IFTA by comparison with one or more reference points. The principles are first discussed with respect to CAN/IFTA without regarding to subtype. However, the same principles apply for analysis of subtypes except that the gene sets used may be different. For example, mild CAN/IFTA can be determined using genes or proteins from Tables A, C, E, F and/or G. Mid to severe CAN/IFTA can be determine using genes or proteins from Tables B, D, H, I and/or J. Genes or proteins from any of the tables can be used in analyzing CAN/IFTA without regard to subtype. Preferably, genes in both Tables A/C and B/D or proteins occurring in at least one of Tables E-G and at least one of Tables H-J are used for such analysis. Genes or proteins are found in both Banff 1 and Banff 2,3 CAN/IFTA but not found in Banff 0 are also useful in distinguishing the presence of CAN/IFTA in a patient. A combination of genes and/or proteins associated with mild CAN/IFTA and genes and/or proteins associated with mid to severe CAN/IFTA can be used.

The reference points can include a measure of an average expression level of a gene in subjects having had a kidney transplant without CAN/IFTA, and/or an average value of expression levels in subjects having had a kidney transplant with CAN/IFTA. The reference points can also include a scale of values found in kidney transplant patients including patients having and not having CAN/IFTA. The reference points can also or alternatively include a reference value in the subject before kidney transplant, or a reference value in a population of a patients who have not undergone kidney transplant. Such reference points can be expressed in terms of absolute or relative concentrations of gene products as for measured values in a sample.

For comparison between a measured expression level and reference level(s), the measured level sometimes needs to be normalized for comparison with the reference level(s) or vice versa. The normalization serves to eliminate or at least minimize changes in expression level unrelated to CAN/IFTA (e.g., from differences in overall health of the patient or sample preparation). Normalization can be performed by determining what factor is needed to equalize a profile of expression levels measured from different genes in a sample with expression levels of these genes in a set of reference samples from which the reference levels were determined. Commercial software is available for performing such normalizations between different sets of expression levels.

Comparison of the measured expression level of a gene with one or more of the above reference points provides a value (i.e., numerical) or other designation (e.g., symbol or word(s)) of presence or susceptibility to CAN/IFTA. In some methods, a binary system is used; that is a measured expression level of a gene is assigned a value or other designation indicating presence or susceptibility to CAN/IFTA or lack thereof without regard to degree. For example, the expression level can be assigned a value of 1 to indicate presence or susceptibility to CAN/IFTA and −1 to indicate absence or lack of susceptibility to CAN/IFTA. Such assignment can be based on whether the measured expression level is closer to an average level in kidney transplant patients having or not having CAN/IFTA. In other methods, a ternary system is used in which an expression level is assigned a value or other designation indicating presence or susceptibility to CAN/IFTA or lack thereof or that the expression level is uninformative. Such assignment can be based on whether the expression level is closer to the average level in kidney transplant patient undergoing CAN/IFTA, closer to an average level in kidney transplant patients lacking CAN/IFTA or intermediate between such levels. For example, the expression level can be assigned a value of +1, −1 or 0 depending on whether it is closer to the average level in patients undergoing CAN/IFTA, is closer to the average level in patients not undergoing CAN/IFTA or is intermediate. In other methods, a particular expression level is assigned a value on a scale, where the upper level is a measure of the highest expression level found in kidney transplant patients and the lowest level of the scale is a measure of the lowest expression level found in kidney transplant patients at a defined time point at which patients may be susceptible to CAN/IFTA (e.g., one year post transplant). Preferably, such a scale is normalized scale (e.g., from 0-1) such that the same scale can be used for different genes. Optionally, the value of a measured expression level on such a scale is indicated as being positive or negative depending on whether the upper level of the scale associates with presence or susceptibility to CAN/IFTA or lack thereof. It does not matter whether a positive or negative sign is used for chronic ejection or lack thereof as long as the usage is consistent for different genes.

Values or other designation can also be assigned based on a change in expression level of a gene relative to a previous measurement of the expression level of gene in the same patient. Here as elsewhere expression level of a gene can be measured at the protein or nucleic acid level. Such a change can be characterized as being toward, away from or neutral with respect to average expression levels of the gene in kidney transplant patients undergoing or not undergoing CAN/IFTA. For example, a gene whose expression level changes toward an average expression level in kidney transplant patients undergoing CAN/IFTA can be assigned a value of 1 and a gene whose express level changes way from an average expression level in kidney transplant patients undergoing CAN/IFTA and toward an average expression level in kidney transplant patients not undergoing CAN/IFTA can be assigned a value −1. Of course, more sophisticated systems of assigning values are possible based on the magnitude of changes in expression of a gene in a patient.

Having determined values or other designations of expression levels of individual genes providing an indication of presence or susceptibility to chronic ejection or lack thereof, the values or designations are combined to provide an aggregate value for all of the genes being analyzed. If each gene is assigned a score of +1 if its expression level indicates presence or susceptibility to CAN/IFTA and −1 if its expression level indicates absence or lack of susceptibility to CAN/IFTA and optionally zero if uninformative, the different values can be combined by addition. The same approach can be used if each gene is assigned a value on the same normalized scale and assigned as being positive or negative depending whether the upper point of the scale is associate with presence or susceptibility to CAN/IFTA or lack thereof. Other methods of combining values for individual markers of disease into a composite value that can be used as a single marker are described in US20040126767 and WO/2004/059293.

VII. Subtyping

CAN/IFTA can be classified into three subtypes, mild, mid and severe by the Banff scheme. These subtypes differ by histology and severity. The subtypes can be distinguished by the same principles and strategy as just discussed for presence or absence of CAN/IFTA, except that the set of genes whose expression levels is determined may be different for presence and absence of CAN/IFTA overall and each of the subtypes as indicated above. In some methods, one first analyzes CAN/IFTA independent of subtype and then looks at profiles of one or more sets of genes characteristic of one of the above subtypes. In some methods, detection of CAN/IFTA and subtypes are performed simultaneously, for example, by including probes for the sets of genes required for each analysis on the same array. In other methods, analysis of multiple subtypes is performed sequentially or simultaneously and analysis of overall CAN/IFTA is performed by aggregating the results from the different subtypes.

The principles for subtyping are closely analogous to those for analyzing CAN/IFTA independent of subtype. For example, to analyze whether mild CAN/IFTA is present, one determines expression levels of a set of genes whose expression levels are characterized of this subtype (Tables A, C, E, F and/or G). The measured expression levels are then compared with one or more reference levels of the genes. The reference levels can, for example, represent an average expression level of a gene in kidney transplant patients undergoing mild CAN/IFTA with borderline phenotype and an average expression level of the gene in kidney transplant patients not undergoing any kidney rejection, an average expression level of the gene in kidney transplant patients undergoing CAN/IFTA of a different subtype, or an earlier measurement of expression level of the gene in the same patient. The same principles are used for analyzing combined moderate/severe CAN/IFTA except that the set of genes is selected from Tables B, D, H, I and/or J and the reference levels represent an average expression level of a gene in transplant patients undergoing CAN/IFTA with Banff subtype 2 or 3, an average expression level of the gene in kidney transplant patients not undergoing kidney rejection of any kind, an average expression level of the gene in kidney transplant patients undergoing CAN/IFTA of a different subtype, or an earlier measurement of expression level of the gene in the same patient.

If subtyping is performed for both mild CAN/IFTA and moderate/severe CAN/IFTA, the aggregate of the results also indicates overall CAN/IFTA. For example, if the patient is assigned a value or other designation indicating absence or relatively low risk of developing mild CAN/IFTA and a value or other designation indicating absence or relatively low risk of developing moderate/severe CAN/IFTA, then the patient is also indicated as having absence of overall CAN/IFTA and/or a relatively low risk of developing the same. Conversely, if the patient is assigned a value or other designation indicating presence or enhanced risk to either mild CAN/IFTA or mid/severe CAN/IFTA, or both, the patients is also indicated as having presence or enhanced risk of overall CAN/IFTA.

VIII. Diagnosis, Prognosis and Monitoring

The above described methods can provide a value or other designation for a patient which indicates whether the aggregate measured expression levels in a patient is more like kidney transplant patients with or without CAN/IFTA or a subtype thereof. Such a value provides an indication that the patient either has or is at enhanced risk of CAN/IFTA or a subtype thereof, or conversely does not have or is at reduced risk of CAN/IFTA or a subtype thereof. Risk is a relative term in which risk of one patient is compared with risk of other patients either qualitatively or quantitatively. For example, the a value of one patient can be compared with a scale of values for a population of patients having undergone kidney transplant to determine whether the patient's risk relative to that of other patients. In general, diagnosis is the determination of the present condition of a patient (e.g., presence or absence of CAN/IFTA) and prognosis is developing future course of the patient (e.g., risk of developing CAN/IFTA in the future or likelihood of improvement in response to treatment); however, the analyses contemplated by these terms may overlap or even be the same. For example, the present methods alone do not necessarily distinguish between presence and enhanced risk of CAN/IFTA or a subtype thereof. However, these possibilities can be distinguished by additional testing.

If a patient is indicated as having or being at enhanced risk of CAN/IFTA or a subtype thereof, the physician can subject the patient to additional testing including performing a kidney biopsy or performing other analyses such as creatinine, BUN or glomerular filtration rate at increased frequency. Additionally or alternatively, the physician can change the treatment regime being administered to the patient. A change in treatment regime can include administering an additional or different drug, or administering a higher dosage or frequency of a drug already being administered to the patient Many different drugs are available for treating rejection, such as immunosuppressive drugs used to treat transplant rejection calcineurin inhibitors (e.g., cyclosporine, tacrolimus), mTOR inhibitors (e.g., sirolimus and everolimus), anti-proliferatives (e.g., azathioprine, mycophenolic acid), corticosteroids (e.g., prednisolone and hydrocortisone) and antibodies (e.g., basiliximab, daclizumab, Orthoclone, anti-thymocyte globulin and anti-lymphocyte globulin). Conversely, if the value or other designation of aggregate expression levels of a patient indicates the patient does not have or is at reduced risk of CAN/IFTA, the physician need not order further diagnostic procedures, particularly not invasive ones such as biopsy. Further, the physician can continue an existing treatment regime, or even decrease the dose or frequency of an administered drug.

In some methods, expression levels are determined at intervals in a particular patient (i.e., monitoring). Such methods can provide a series of values changing over time indicating whether the aggregate expression levels in a particular patient are more like the expression levels in patients undergoing CAN/IFTA or not undergoing CAN/IFTA. Movement in value toward or away from CAN/IFTA or a subtype can provide an indication whether an existing immunosuppressive regime is working, whether the immunosuppressive regime should be changed or whether a biopsy or increased monitoring by markers such as creatinine or glomerular filtration rate should be performed.

Information from subtyping analysis can provide further guidance in whether to perform additional diagnostic measures and/or change the immunosuppressive regime administered to a subject. For example, presence or risk of subtype 2 or 3 is more suggestive of performing an additional diagnostic procedure (e.g., biopsy) and/or increasing the rigor of an immunosuppressive regime that is the presence or risk of subtype 1.

IX. Drug Screening

The expression profiles associated with CAN/IFTA (including subtypes) or lack thereof provided by the invention are useful in screening drugs, either in clinical trials or in animal models of CAN/IFTA. A clinical trial can be performed on a drug in similar fashion to the monitoring of a individual patient described above, except that drug is administered in parallel to a population of kidney transplant patients, usually in comparison with a control population administered a placebo.

The changes in expression levels of genes can be analyzed in individual patients and across a treated or control population. Analysis at the level of an individual patient provides an indication of the overall status of the patient at the end of the trial (i.e., whether gene expression profile indicates presence or enhanced susceptibility to CAN/IFTA) and/or an indication whether that profile has changed toward or away from such indication in the course of the trial. Results for individual patients can be aggregated for a population allowing comparison between treated and control population.

Similar trials can be performed in non-human animal models of chronic kidney disease, e.g., the mouse model of Mannon et al., Kidney International (1999) 55, 1935-1944 In this case, the expression levels of genes detected are the species variants or homologs of the human genes referenced above in whatever species of non-human animal on which tests are being conducted. Although the average expression levels of human genes determined in human kidney transplant patients undergoing or not undergoing CAN/IFTA are not necessarily directly comparable to those of homolog genes in an animal model, the human values can nevertheless be used to provide an indication whether a change in expression level of a non-human homolog is in a direction toward or away from CAN/IFTA or susceptibility thereto. The expression profile of individual animals in a trial can provide an indication of the status of the animal at the end of the trial with respect to presence or susceptibility to CAN/IFTA and/or change in such status during the trial. Results from individual animals can be aggregated across a population and treated and control populations compared. Average changes in the expression levels of genes can then be compared between the two populations.

X. Computer Implemented Methods

Expression levels can be analyzed and associated with status of a subject (e.g., presence or susceptibility to chronic kidney infection) in a digital computer. Optionally, such a computer is directly linked to a scanner or the like receiving experimentally determined signals related to expression levels. Alternatively, expression levels can be input by other means. The computer can be programmed to convert raw signals into expression levels (absolute or relative), compare measured expression levels with one or more reference expression levels, or a scale of such values, as described above. The computer can also be programmed to assign values or other designations to expression levels based on the comparison with one or more reference expression levels, and to aggregate such values or designations for multiple genes in an expression profile. The computer can also be programmed to output a value or other designation providing an indication of presence or susceptibility to CAN/IFTA as well as any of the raw or intermediate data used in determining such a value or designation.

A typically computer (see U.S. Pat. No. 6,785,613 FIGS. 4 and 5) includes a bus which interconnects major subsystems such as a central processor, a system memory, an input/output controller, an external device such as a printer via a parallel port, a display screen via a display adapter, a serial port, a keyboard, a fixed disk drive and a floppy disk drive operative to receive a floppy disk. Many other devices can be connected such as a scanner via I/O controller, a mouse connected to serial port or a network interface. The computer contains computer readable media holding codes to allow the computer to perform a variety of functions. These functions include controlling automated apparatus, receiving input and delivering output as described above. The automated apparatus can include a robotic arm for delivering reagents for determining expression levels, as well as small vessels, e.g., microtiter wells for performing the expression analysis.

EXAMPLES

Materials and Methods:

Patient Populations: Test Set 1 comprised 42 kidney transplant patients randomized to either cyclosporine or de novo rapamycin at the Cleveland Clinic, whose clinical courses have been previously, described [15,16,24]. Density gradient-purified peripheral blood lymphocytes (PBL) were collected at the time of protocol two-year biopsies. Test Set 2 comprised 35 patients from 3 clinical centers (St. Vincent's Medical Center, Scripps Clinic, and Cleveland Clinic). All patients were on FK506. Whole blood was collected directly into PaxGene Tubes (PreAnalytix) at the time of biopsies for suspected CAN/IFTA or protocol one-year biopsies. All the studies in this manuscript were covered by Human Subjects Research Protocols approved by each Center's Institutional Review Board and by the IRB of The Scripps Research Institute as the parent institution. Informed consent was obtained from all study subjects in the study.

Pathology: Banff IFTA grades based on tubulointerstitial features were determined for all patients by kidney biopsies: grade 0 (no evidence CAN/IFTA), 1 (mild CAN/IFTA), and 2 (moderate CAN/IFTA) and 3 (severe CAN/IFTA). We merged patients with Banff 2 and Banff 3 IF/TA to increase numbers. Diagnosis was done first by local pathologists and reviewed in a blinded fashion. C4d staining was only available in the more recently acquired Test Set 2.

Gene expression profiling and analysis: RNA was extracted from Test Set 1 using Trizol (Invitrogen) and in Test Set 2 using Paxgene Blood RNA system (PreAnalytix) and globin transcripts were reduced using GlobinClear (Ambion). Biotinylated cRNA was prepared using Ambion MessageAmp Biotin II (Ambion) and hybridized to Affymetrix Human Genome U133 Plus 2.0 GeneChips. Normalized signals that were generated using a quantile normalization strategy (RMAExpress[25]) were used for class comparisons (ANOVA) and class predictions (BRB Array Tools; linus.nci.nih.gov/BRB-ArrayTools.html). We chose the Diagonal Linear Discriminant Analysis (DLDA) method for class predictions, which is based on maximum likelihood discriminant rules that give consistently good results with our data set and others[26]. Receiver Operating Characteristics (ROC) analysis was done using JROCFIT (rad.jhmi.edu/jeng/javarad/roc/JROCFITi.html). Heatmaps were generated using Cluster and Treeview[27] and functional analysis was performed using Gene Ontology (GO) (geneontology.org/) and Ingenuity Pathway Analysis (IPA). Consensus analysis was designed to identify true classifiers in the two independently collected data sets. Variability between the two test sets within each class (i.e. Banff 1/Test Set 1 vs. Banff 1/Test Set 2) was eliminated by removing all genes with a Student's t-test p-value of <0.05 after which the remaining genes were used to identify consensus candidates by class comparisons. All the microarray data for this study is available for review at the private GEO accession site ncbi.nlm.nih.gov/geo/query/acc.cgi?token=vbgvzkwuggqiqpy&acc=GSE12187.

Shotgun LC/MS/MS proteomics: All protein samples were prepared from density gradient-purified PBL. Individual patient samples were pooled within each Test Set (3 samples/pool) based on Banff classifications and pools were run in triplicates. Total protein was proteolytically digested with trypsin and samples run using Multidimensional Protein Identification Tool (MudPIT) protocol as previously described[28] using an LTQ XL mass spectrometer (ThermoFisher). Raw data were searched against the EBI-IPI_human_12_01_2006 database supplemented with a decoy database where each entry of the original protein contains its reversed sequence. Database searching used SEQUEST (v27)[29] and outcomes were filtered using DTASelect[30]. Relative quantifications were done using spectral counts normalized to the median of the total spectral counts[31]. Pair-wise comparisons between CAN/IFTA biopsy classes were done by differentially expressed proteins (Student's t-test, p≤0.05) and as all-or-none/unique events.

Results:

Study Population

Recipients in both Test Sets were sex and age matched (Table 1). The only significant differences in Test Set 1 were Donor age between Banff 0 and Banff 1 groups. In Test Set 2 there were significant differences in induction therapy between Banff 0 and Banff 1 and between Banff 0 and the Banff 2,3; time to biopsy between Banff 0 and Banff 1 and between Banff 0 and the Banff 2,3; and steroid use between Banff 0 and Banff 1 and between Banff 0 and Banff 2,3. Only the Banff 2,3 group in Test Set 2 had a significantly higher serum creatinine compared to the Banff 0, thus, renal function levels per se were not a major determinant of the gene profiles. The higher creatinine levels in the Banff 2,3 group of Test Set 2 most likely reflect the fact that this group was "biopsy for cause," whereas Test Set 1 were all protocol biopsies done regardless of any renal function change. However, by design, the two Test Sets differed significantly in recipient age, HLA mismatch, induction therapy, clinical center, immunosuppression, serum creatinines, and time to biopsy.

Gene Expression Profiling of Mild CAN/IFTA

We performed ANOVA-based class comparisons between Banff 0 (no histological evidence of CAN/IFTA) and Banff 1 (mild CAN/IFTA). At p-values <0.005, 1066 genes (1307 probe sets) were differentially expressed. Annotation of function by Gene Ontology (GO) shows 8 categories comprised of >25 genes each including 58 genes linked to immunity and inflammation. The percentage of genes in each category was immune/inflammatory 5%, apoptosis, 4%, cell adhesion 3%, signal transduction 5%, regulation of transcription 6%, protein phosphorylation 3%, cell cycle 3%, metabolism 11%, other functions 40%, unknown functions 20%. IPA shows that these 1066 genes fall into 27 networks with >15 genes per network. The top network was immune response and two additional networks in the top 10 were also immune response with 27 and 22 focus genes, respectively. The top canonical pathway was Toll-like Receptor Signaling followed by SAPK/JNK, Apoptosis, Notch and Death Receptor and Interferon Signaling. Finding 1066 significantly differentially expressed genes is a first indication that PBL transcript profiling is capable of classifying subjects defined by CAN/IFTA biopsy histology. Class prediction using DLDA demonstrates 90% mean correct classification[32,33]. Supervised hierarchical clustering shows misclassification of only 2 samples.

Based on gene expression profiles of the whole blood samples in Test Set 2, there were 1429 genes (1591 probe sets) differentially expressed at p-values <0.005. GO annotation of gene functions revealed the same groups as PBL including 50 immune response genes. The percentage of genes in each category was immune/inflammatory 4%, apoptosis, 2%, cell adhesion 2%, signal transduction 8%, regulation of transcription 6%, protein phosphorylation 1%, cell cycle 1%, metabolism 4%, other functions 35%, unknown functions 37%. IPA reveals 30 networks with >15 genes per network. The top canonical pathways were: B Cell Receptor, Toll-like Receptor, Death Receptor, Chemokine, Glucocorticoid Receptor, and IL-4 Signaling. DLDA demonstrates 88% mean correct classification. Supervised hierarchical clustering shows misclassification of only 1 sample.

A consensus analysis for Banff 0 vs. Banff 1 was performed with these two independently collected data sets by a class comparison at p-values <0.005 and identified 393 genes (424 probe sets) significantly differentially expressed in both data sets. This "consensus" gene list represents the intersection of these two significantly different test sets classifying mild CAN/IFTA by blood transcription profiling. We then combined all the samples of both Test Sets (n=55) and performed class predictions using the top 50 differentially expressed, consensus genes ranked by p values to obtain a class prediction accuracy of 80% depicted as a ROC curve (FIG. 1). A heat map classifying Banff 0 vs. Banff 1 using the 50 genes shows there are large "blocks" of up- or down-regulated genes that classify the Banff 0 vs. Banff 1 (mild CAN/IFTA). However, signatures of multiple genes are advantageous to achieve high class predictive accuracies in heterogeneous clinical populations that are the reality of transplantation medicine. We took the top 10 and top 3 genes from our consensus set for mild CAN/IFTA and performed class prediction using the DLDA method. The top 10 had a predictive accuracy of 80%, sensitivity of 85% and specificity of 77%, whereas the top 3 genes had a predictive accuracy of 80%, sensitivity of 74% and specificity of 86%.

Gene Expression Profiling of Moderate/Severe CAN/IFTA

Figure 2:
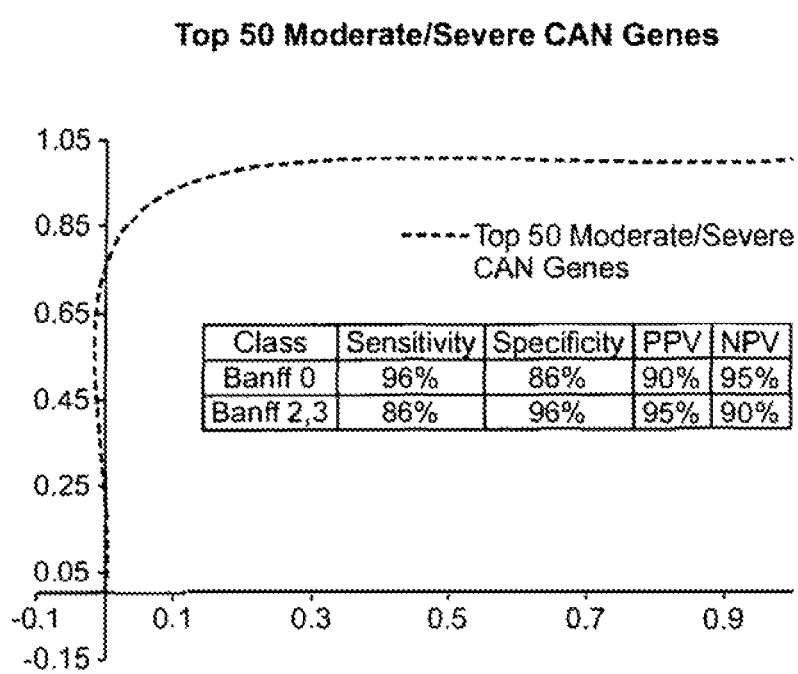
FIG. 2: Class prediction analysis of Banff 0 vs. Banff 2,3 (moderate to severe CAN/IFTA) based on Diagonal Linear Discriminant Analysis for the top 50 Banff 0 vs. Banff 2,3 consensus genes ranked by p values. A) depicts the Receiver Operating Characteristic (ROC) curves and provides the Sensitivity, Specificity, Positive Predictive Value (PPV) and Negative Predictive Value (NPV); B) depicts the heat map classifying Banff 0 vs. Banff 2,3 using the top 50 consensus genes where (red) is up-regulated and (green) is down-regulated.

Class comparisons between Banff 0 and Banff 2,3 identified genes differentially expressed between patients without CAN/IFTA and those with moderate to severe CAN/IFTA. In Test Set 1, 172 genes were differentially expressed (p<0.005) and classified the samples by DLDA with 78% accuracy. In Test Set 2 there were 545 differentially expressed genes. DLDA classified 95% of the samples accurately. The percentage of genes in each category for sets 1 and 2 was immune/inflammatory 4%, 3%, apoptosis, 2%, 3%, cell adhesion 2%, 3%, signal transduction 8%, 7%, regulation of transcription 6%, 8%, protein phosphorylation 1%, 3%, cell cycle 1%, 1%, metabolism 4%, 6% other functions 33%, 30%, unknown functions 37%, 36%. A consensus analysis was done as already described to yield 62 differentially expressed genes (p<0.005) shared for both Test Sets of moderate/severe CAN/IFTA (n=49). The ROC curve for the top 50 genes from this consensus gene set shows a class prediction accuracy of 92% (FIG. 2).

Proteomic Expression of Mild and Moderate/Severe CAN/IFTA

To investigate using proteomics to define blood cell biomarkers for CAN/IFTA, we performed shotgun tandem mass spectrometry. All samples represented purified PBL obtained at the same time as biopsies. We did not use the whole blood samples from Test Set 2 because high quality protein preparations cannot be obtained from PaxGene tubes. Differential protein expression was performed using a relative quantification strategy based on normalized spectral counts [31]. We identified 206 differentially expressed proteins ($p<0.05$) for Banff 0 vs. Banff 1 (mild CAN/IFTA). In addition, we identified 135 proteins unique to Banff 0 and 167 proteins unique to Banff 1. Class comparisons for Banff 0 vs. Banff 2,3 (moderate/severe CAN/IFTA) yielded 282 differentially expressed proteins ($p<0.05$) and 509 proteins unique to Banff 2,3. We found 95 proteins differentially expressed in mild and moderate/severe CAN/IFTA as compared to Banff 0, representing candidate protein markers for any stage of CAN/IFTA. In parallel, 94 proteins were differentially expressed only in mild CAN/IFTA and these were linked to cell death, cell signaling, and post-translational protein modifications. The 168 proteins differentially expressed only in moderate/severe CAN/IFTA were linked to cellular morphology, growth and proliferation and signaling via ERK/MAPK, acute phase responses, IGF1 and PPARa/RXRa.

There were 135 proteins unique to mild CAN/IFTA and 322 proteins unique to moderate/severe CAN/IFTA. Both mild and moderate/severe CAN/IFTA had immune and inflammation related proteins (20 and 37, respectively) but many of these proteins are not mapped to the same functional pathways (e.g. calcium signaling in mild CAN/IFTA and apoptosis, NK cell and PTEN signaling for moderate/severe CAN/IFTA). In other cases, such as signaling via T and B cell receptors, IL4 and JAK/STAT, the same canonical pathways were found but different unique proteins were identified.

Using only the differentially expressed proteins, DLDA obtained a 64% mean correct classification of mild CAN/IFTA and an 83% correct classification for moderate/severe CAN/IFTA. In contrast, the unique proteins identified only in the blood of patients with biopsy-documented mild (n=135) or moderate/severe CAN/IFTA (n=322), represent candidate biomarkers with a 100% class prediction value in this data set.

We compiled the matches between proteins identified by mass spectrometry and mRNA transcripts identified using microarrays. The premise is that protein/transcript matches are a form of candidate biomarker validation based on two independent technologies. There were 11 matches for the 393 consensus genes for mild CAN/IFTA, 32 matches for the 1066 genes for mild CAN/IFTA in Test Set 1 and 40 matches for the 1429 genes for mild CAN/IFTA in Test Set 2. There were no matches for the 62 consensus genes for moderate/severe CAN/IFTA but 9 matches in the 172 genes for moderate/severe CAN/IFTA in Test Set 1 and 9 matches in the 545 genes for moderate/severe CAN/IFTA in Test Set 2. All protein/transcript matches are listed in Tables 2-6.

DISCUSSION

The primary objective of this study (also reported as [40]) was the discovery of biomarkers in the peripheral blood of kidney transplant patients with biopsy-documented interstitial fibrosis and tubular atrophy (IF/TA) and no known cause, which we refer to here as Chronic Allograft Nephropathy (CAN/IFTA)[14]. To this end, we integrated the results of two, independently collected sets of patient samples that were significantly different in multiple clinical elements. Thus, the selection of biomarker candidates was not significantly influenced by the time of biopsy (ranging from 1 to 6 years post-transplant), the specific immunosuppressive protocols (use of different calcineurin inhibitors vs. sirolimus) or the technology used to purify the mRNA transcripts (density gradient-separated cells vs. whole blood). This experimental design was chosen for its advantages in defining a consensus set of robust candidate biomarkers for CAN/IFTA suitable for clinical use.

Using more closely matched sets of patient samples, for example, patients only 2 years post-transplant or only one source of blood cell RNA such as the PaxGene tubes might have resulted in higher total numbers of differentially expressed candidate mRNA transcripts and proteins. However, classifications for CAN/IFTA based on the consensus mRNA candidates described here for these otherwise very heterogeneous clinical data sets are 80% for mild CAN/IFTA and 92% for moderate/severe CAN/IFTA. By contrast, the widely used prostate specific antigen (PSA) biomarker, tested in an equally heterogenous human population, was originally introduced with a predictive value of 28-35%[34] because there was no other minimally invasive option for early detection of prostate cancer at that time, which is true for CAN/IFTA today.

We obtain very reasonable predictive accuracy, sensitivity and specificity with 150, 100 and 50 total genes per signature. There are now several technology platforms perfectly suitable for point of clinical service implementation that can measure 100 genes or more cost effectively and within hours. In clinical practice, the differentially expressed genes and proteins can be used for serial, prospective measurements of the signature at regular intervals for the life of the kidney transplant. The absence of a positive CAN/IFTA signature at any point in time will indicate adequate immunosuppression or over-immunosuppression. Careful reductions in immunosuppressive drug doses can then be used with repeat monitoring of the signature to establish the optimal drug combination and level for each patient to prevent CAN/IFTA and ensure the long term safety of the therapy.

Biomarker discovery has been reported using peripheral blood profiling for acute rejection in heart transplantation [35,36]. Peripheral blood studies of kidney transplant patients with "operational tolerance" included 22 patients with biopsy-documented CAN/IFTA[37]. Two of the genes (DPYD, IRS2) reported to distinguish "operational tolerance" are identified in our consensus sets. Our earlier study of 42 kidney biopsies showed that gene expression profiles of CAN/IFTA had significant up-regulation of immune/inflammation, fibrosis and tissue remodeling genes[16]. However, only 5 genes from these CAN/IFTA biopsies were identified in the current peripheral blood consensus sets. A study of 11 CAN/IFTA biopsies identified 3 genes linked to immunity and fibrosis that were tested by quantitative PCR in urine and peripheral blood with good correlations in urine but none in peripheral blood[38]. Therefore, gene biomarkers identified in peripheral blood are mostly distinct from those identified in tissue.

Although practice of the invention is not dependent on an understanding of mechanism, we propose that the peripheral blood represents a fully functional and distinct compartment of the immune system that actively serves to traffic and modulate all the components of effector immunity. Although the tissue injury that causes the progression of CAN/IFTA is occurring in the kidney, we believe that a significant determinant of the phenotype of the host immune response, either acceptance of the graft or CAN/IFTA, is actually established and subsequently regulated within the peripheral blood compartment, lymph nodes and spleen.

Urine based proteomics have been used to report biomarkers for acute rejection using SELDI-TOF mass spectroscopy [23,39] but to our knowledge this is the first study to identify blood cell-based proteomic markers for transplantation using tandem mass spectroscopy. We have identified several hundred proteins that are significantly differentially expressed in peripheral blood of patients with CAN/IFTA as a function of histology grade, mild to moderate/severe. The group of uniquely identified proteins potentially represents the highest value biomarker candidates giving 100% accuracy in our tests. Integrating proteomics with gene expression, we identified over 80 protein/transcript matches for CAN/IFTA providing candidate validation based on two independent technologies.

However, genes in which differential expression is found only at the gene or protein level but not both also allow accurate analyses.

Although the invention has been described with reference to the presently preferred embodiments, it should be understood that various modifications can be made without departing from the invention. Unless otherwise apparent from the context any step, element, embodiment, feature or aspect of the invention can be used with any other.

All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with Genbank, Unigene, International Protein Index, Entrez, UniProtKB/Swiss-Prot accession numbers and the like, the application refers to the sequences associated with the cited accession numbers as of Jul. 9, 2009.

REFERENCES

1. Meier-Kriesche (2001) J Am Soc Nephrol 12: 1293-1296.
2. Nankivell (2003) N Engl J Med 349: 2326-2333.
3. Pascual (2002) N Engl J Med 346: 580-590.
4. Solez (2008) Am J Transplant 8: 753-760.
5. Racusen (1999) Kidney Int 55: 713-723.
6. Solez K, (2007) Am J Transplant 7: 518-526.
7. Banasik M, Klinger M (2006) Am J Transplant 11: 7-10.
8. Yates (2006) Transpl Immunol 16: 148-157.
9. Calne (1978) Lancet 2: 1323-1327.
10. de Mattos (2000) Am J Kidney Dis 35: 333-346.
11. Jevnikar (2008) Clin J Am Soc Nephrol 3 Suppl 2: S56-67.
12. Pascual. (1998) Immunol Today 19: 514-519.
13. Nankivell (2006) Transplantation 81: 643-654.
14. Colvin R B (2003) N Engl J Med 349: 2288-2290.
15. Flechner (2007) Transplantation 83: 883-892.
16. Flechner (2004) Am J Transplant 4: 1776-1785.
17. Yilmaz (2007) Transpl Int 20: 608-615.
18. Lachenbruch (2004) Am J Transplant 4: 451-457.
19. Pascual (1999) Transplantation 67: 737-741.
20. Kurian (2005) Current Opinion in Organ Transplantation 10: 193-197.
21. Kurian (2007) Int Immunopharmacol 7: 1948-1960.
22. Oetting (2006) Am J Kidney Dis 47: 898-904.
23. Schaub (2005) Am J Transplant 5: 729-738.
24. Flechner (2004) Am J Transplant 4: 1475-1489.
25. Bolstad (2003) Bioinformatics 19: 185-193.
26. Dudoit (2002) Journal of the American Statistical Association 97: 77-87.
27. Eisen (1998) Proc Natl Acad Sci USA 95: 14863-14868.
28. Washburn (2001) Nat Biotechnol 19: 242-247.
29. Sadygov (2002) J Proteome Res 1: 211-215.
30. Tabb (2002) J Proteome Res 1: 21-26.
31. Liu (2004) Anal Chem 76: 4193-4201.
32. Guo (2007) Biostatistics 8: 86-100.
33. Huang (2006) Pediatr Blood Cancer 46: 728-738.
34. Woolf (1995) N Engl J Med 333: 1401-1405.
35. Deng (2006) Am J Transplant 6: 150-160.
36. Horwitz (2004) Circulation 110: 3815-3821.
37. Brouard (2007) Proc Natl Acad Sci USA 104: 15448-15453.
38. Mas (2007) Transplantation 83: 448-457.
39. Clarke (2003) Ann Surg 237: 660-664; discussion 664-665.
40. Kurian et al., PLoS One. 2009 Jul. 10; 4(7):e6212

TABLE 1

Clinical Characteristics of the Study Populations.

| | Test Set 1 | | | | Test Set 2 | | | | Test Set 1 vs. Test Set 2 |
|---|---|---|---|---|---|---|---|---|---|
| | Banff 0 | Banff 1 | Banff 2, 3 | Significance | Banff 0 | Banff 1 | Banff 2, 3 | Significance | Significance |
| Number | 18 | 15 | 9 | NA | 8 | 14 | 13 | NA | NS |
| Recipient age | 42.61 ± 12.8 | 48.47 ± 11.6 | 45.67 ± 17.5 | NS | 56.88 ± 12.2 | 51.36 ± 12.6 | 49.08 ± 12.9 | NS | Banff0 = 0.01 |
| Recipient gender (% female) | 38.9 | 20 | 44.4 | NS | 62.5 | 35.7 | 53.8 | NS | NS |
| Recipient race African American | 22.22 | 13.33 | 11.11 | NS | 0 | 14.3 | 7.7 | NS | NS |
| Pre tx diabetes | 16.7 | 26.7 | 22.2 | NS | 25 | 14.3 | 7.7 | NS | NS |
| PRA >20% (%) | 5.6 | 6.7 | 11.1 | NS | 12.5 | 7.1 | 15.4 | NS | NS |
| HLA mismatch | 3.06 ± 1.7 | 2.66 ± 1.6 | 2.67 ± 2.2 | NS | 3.43 ± 2.4 | 4.33 ± 1.4 | 3.58 ± 1.6 | NS | Banff1 = 0.008 |
| Deceased donor | 55.6 | 73.3 | 77.8 | NS | 75 | 71.4 | 46.2 | NS | NS |
| % re-transplant | 0 | 0 | 0 | — | 0 | 14.3 | 15.4 | NS | NS |
| Donor age | 32.39 ± 15.7 | 42.33 ± 11.8 | 37.11 ± 12.1 | Banff0 vs. Banff1 p = 0.05 | 31.25 ± 19.3 | 41.54 ± 17.7 | 44.62 ± 13.4 | NS | NS |

TABLE 1-continued

Clinical Characteristics of the Study Populations.

| | Test Set 1 | | | | Test Set 2 | | | | Test Set 1 vs. Test Set 2 |
|---|---|---|---|---|---|---|---|---|---|
| | Banff 0 | Banff 1 | Banff 2, 3 | Significance | Banff 0 | Banff 1 | Banff 2, 3 | Significance | Significance |
| Donor gender female | 50 | 53.3 | 33.3 | NS | 12.5 | 57 | 53.8 | NS | NS |
| Donor race African American | 16.7 | 13.3 | 11.1 | NS | 0 | 7.1 | 7.7 | NS | NS |
| Induction | 100 | 100 | 100 | NS | 75 | 21.4 | 23.1 | Banff0 vs. Banff1 p = 0.026; Banff0 vs. Banff2, 3 p = 0.032 | Banff1 = 0.0001 Banff2, 3 = 0.0005 |
| Serum Creatinine | 1.32 ± 0.38 | 1.45 ± 0.51 | 1.84 ± 0.77 | NS | 1.70 ± 1.3 | 2.41 ± 0.7 | 3.09 ± 1.2 | Banff0 vs. Banff2, 3 p = 0.025 | Banff1 = 0.0002 Banff2, 3 = 0.007 |
| Time to Biopsy | 755 ± 101 | 710 ± 109 | 659 ± 133 | NS | 420 ± 309 | 1664 ± 1364 | 2398 ± 1120 | Banff0 vs. Banff1 p = 0.005; Banff0 vs. Banff2, 3 p = 0.00002 | Banff0 = 0.05 Banff1 = 0.02 Banff2, 3 = 0.0001 |
| CNI | 38.9 | 60 | 77.8 | NS | 100 | 100 | 84.6 | NS | Banff0 = 0.007 |
| MMF | 100 | 93.3 | 88.9 | NS | 75 | 78.6 | 76.9 | NS | NS |
| Steroids | 100 | 100 | 100 | NS | 37.5 | 100 | 92.3 | Banff0 vs. Banff1 p = 0.0002; Banff0 vs. Banff2, 3 p = 0.0022 | Banff1 = 0.0009 |
| C4d+ staining* | ND | ND | ND | NA | NA | 2 | 3 | NS | NA |

ND-Not Done
NA-Not Applicable
NS-Not Significant

TABLE A

Differentially expressed consensus genes for mild CAN for both Test
Mild CAN = CAN Banff Class 1; No evidence of CAN = CAN Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 1 | 0.000002 | 27.9 | 19.3 | −1.45 | 203796_s_at | BCL7A | B-cell CLL/lymphoma 7A |
| 2 | 2.1E−06 | 11.6 | 16.7 | 1.44 | 233650_at | CEP63 | centrosomal protein 63 kDa |
| 3 | 3.2E−06 | 50.5 | 40.1 | −1.26 | 1552892_at | TNFRSF13C | tumor necrosis factor receptor superfamily, member 13C |
| 4 | 5.9E−06 | 19.2 | 33.6 | 1.75 | 1565597_at | EST1 | Homo sapiens, clone IMAGE: 4275461, mRNA |
| 5 | 8.3E−06 | 15.1 | 23.5 | 1.56 | 241752_at | SLC8A1 | solute carrier family 8 (sodium/calcium exchanger), member 1 |
| 6 | 1.25E−05 | 803.7 | 1050.5 | 1.31 | 213702_x_at | ASAH1 | N-acylsphingosine amidohydrolase (acid ceramidase) 1 |
| 7 | 1.61E−05 | 224.8 | 174.8 | −1.29 | 223259_at | ORMDL3 | ORM1-like 3 (S. cerevisiae) |
| 8 | 1.84E−05 | 135.4 | 189.9 | 1.40 | 204054_at | PTEN | phosphatase and tensin homolog (mutated in multiple advanced cancers 1) |
| 9 | 1.86E−05 | 26 | 46 | 1.77 | 239012_at | IBRDC2 | IBR domain containing 2 |
| 10 | 2.39E−05 | 1182 | 1724.7 | 1.46 | 200975_at | PPT1 | Palmitoyl-protein thioesterase 1 (ceroid-lipofuscinosis, neuronal 1, infantile) |
| 11 | 0.000024 | 174.3 | 363.5 | 2.09 | 206584_at | LY96 | Lymphocyte antigen 96 |
| 12 | 3.35E−05 | 9 | 7.6 | −1.18 | 228044_at | C13orf21 | Chromosome 13 open reading frame 21 |
| 13 | 4.41E−05 | 250.1 | 327.6 | 1.31 | 225492_at | EST2 | — |
| 14 | 4.53E−05 | 7828 | 10660.2 | 1.36 | 202917_s_at | S100A8 | S100 calcium binding protein A8 |
| 15 | 0.000047 | 374.1 | 724.5 | 1.94 | 223501_at | TNFSF13B | Tumor necrosis factor (ligand) superfamily, member 13b |
| 16 | 4.75E−05 | 112.7 | 204 | 1.81 | 222496_s_at | FLJ20273 | RNA-binding protein |
| 17 | 5.11E−05 | 22.4 | 38.8 | 1.73 | 224996_at | EST3 | CDNA FLI39064 fis, clone NT2RP7014583 |
| 18 | 5.13E−05 | 21.6 | 17.5 | −1.23 | 244863_at | EST4 | Transcribed locus |
| 19 | 0.000052 | 7.5 | 9 | 1.20 | 238791_at | ZNF100 | Zinc finger protein 100 |
| 20 | 5.66E−05 | 85.2 | 123.8 | 1.45 | 218177_at | CHMP1B | Chromatin modifying protein 1B |
| 21 | 5.67E−05 | 203.3 | 336.4 | 1.65 | 226208_at | ZSWIM6 | Zinc finger, SWIM-type containing 6 |
| 22 | 7.26E−05 | 180.8 | 237.2 | 1.31 | 203778_at | MANBA | Mannosidase, beta A, lysosomal |

TABLE A-continued

Differentially expressed consensus genes for mild CAN for both Test
Mild CAN = CAN Banff Class 1; No evidence of CAN = CAN Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 23 | 0.000089 | 86.6 | 123.4 | 1.42 | 238903_at | LOC137886 | Hypothetical protein LOC137886 |
| 24 | 0.000094 | 19.7 | 14.5 | −1.36 | 214308_s_at | HGD | Homogentisate 1,2-dioxygenase (homogentisate oxidase) |
| 25 | 0.000103 | 492.9 | 744.6 | 1.51 | 211368_s_at | CASP1 | Caspase 1, apoptosis-related cysteine peptidase (interleukin 1, beta, convertase) |
| 26 | 0.000103 | 132.8 | 184.8 | 1.39 | 227017_at | ERICH1 | Glutamate-rich 1 |
| 27 | 0.000107 | 10.3 | 15.5 | 1.50 | 228624_at | TMEM144 | Transmembrane protein 144 |
| 28 | 0.000108 | 128.7 | 170.2 | 1.32 | 232149_s_at | NSMAF | Neutral sphingomyelinase (N-SMase) activation associated factor |
| 29 | 0.000112 | 26.4 | 35.2 | 1.33 | 243287_s_at | OSTM1 | Osteopetrosis associated transmembrane protein 1 |
| 30 | 0.000116 | 59.5 | 134.7 | 2.26 | 1552773_at | CLEC4D | C-type lectin domain family 4, member D |
| 31 | 0.000121 | 2887.4 | 3972.4 | 1.38 | 202902_s_at | CTSS | Cathepsin S |
| 32 | 0.000125 | 142.4 | 229 | 1.61 | 211744_s_at | CD58 | CD58 molecule |
| 33 | 0.000133 | 35.6 | 26.9 | −1.32 | 243507_s_at | C20orf196 | Chromosome 20 open reading frame 196 |
| 34 | 0.000137 | 101.9 | 77.4 | −1.32 | 228832_at | FLJ20021 | Hypothetical LOC90024 |
| 35 | 0.000149 | 1057.6 | 1433.5 | 1.36 | 202727_s_at | IFNGR1 | Interferon gamma receptor 1 |
| 36 | 0.000169 | 40.5 | 55.5 | 1.37 | 213952_s_at | ALOX5 | Arachidonate 5-lipoxygenase |
| 37 | 0.000174 | 364.6 | 288.1 | −1.27 | 219045_at | RHOF | Ras homolog gene family, member F (in filopodia) |
| 38 | 0.000175 | 666 | 974.1 | 1.46 | 212268_at | SERPINB1 | Serpin peptidase inhibitor, clade B (ovalbumin), member 1 |
| 39 | 0.00018 | 80.3 | 119.4 | 1.49 | 203276_at | LMNB1 | Lamin B1 |
| 40 | 0.00019 | 347.2 | 814.1 | 2.34 | 219666_at | MS4A6A | Membrane-spanning 4-domains, subfamily A, member 6A |
| 41 | 0.000204 | 54.9 | 110.9 | 2.02 | 204860_s_at | NAIP/// NAIP1B | NLR family, apoptosis inhibitory protein///neuronal apoptosis inhibitory protein (centromeric) |
| 42 | 0.000212 | 3812.4 | 4958.6 | 1.30 | 202388_at | RGS2 | Regulator of G-protein signaling 2, 24 kDa |
| 43 | 0.000226 | 24.5 | 43.9 | 1.79 | 1553514_a_at | VNN3 | Vanin 3 |
| 44 | 0.000239 | 84.6 | 108.3 | 1.28 | 218364_at | LRRFIP2 | Leucine rich repeat (in FLII) interacting protein 2 |
| 45 | 0.000242 | 15.5 | 21.5 | 1.39 | 218888_s_at | NETO2 | Neuropilin (NRP) and tolloid (TLL)-like 2 |
| 46 | 0.000258 | 64.6 | 87.8 | 1.36 | 204108_at | NFYA | Nuclear transcription factor Y, alpha |
| 47 | 0.000273 | 35.6 | 50.1 | 1.41 | 213935_at | ABHD5 | Abhydrolase domain containing 5 |
| 48 | 0.000278 | 54 | 75.5 | 1.40 | 208883_at | UBR5 | Ubiquitin protein ligase E3 component n-recognin 5 |
| 49 | 0.000282 | 334.9 | 425 | 1.27 | 222148_s_at | RHOT1 | Ras homolog gene family, member T1 |
| 50 | 0.000284 | 564.8 | 712.6 | 1.26 | 227266_s_at | FYB | FYN binding protein (FYB-120/130) |
| 51 | 0.000287 | 75.4 | 138.6 | 1.84 | 204714_s_at | F5 | Coagulation factor V (proaccelerin, labile factor) |
| 52 | 0.000302 | 6.3 | 5.6 | −1.13 | 229777_at | CLRN3 | Clarin 3 |
| 53 | 0.000302 | 16.9 | 19.2 | 1.14 | 241073_at | EST5 | Transcribed locus |
| 54 | 0.000309 | 29.8 | 52.7 | 1.77 | 1558549_s_at | VNN1 | Vanin 1 |
| 55 | 0.000319 | 584.3 | 710 | 1.22 | 201007_at | HADHB | Hydroxyacyl-Coenzyme A dehydrogenase/2-ketoacyl-Coenzyme A thiolase/enoyl-Coenzyme A hydratase (trifunctional protein), beta subunit |
| 56 | 0.000323 | 9 | 7.8 | −1.15 | 241171_at | EST6 | Transcribed locus |
| 57 | 0.000328 | 18.4 | 33.5 | 1.82 | 239759_at | EST7 | Transcribed locus |
| 58 | 0.000368 | 44.5 | 76.4 | 1.72 | 209684_at | RIN2 | Ras and Rab interactor 2 |
| 59 | 0.000369 | 22.6 | 18.4 | −1.23 | 240654_at | EST8 | Transcribed locus |
| 60 | 0.00037 | 356 | 693 | 1.95 | 217738_at | PBEF1 | Pre-B-cell colony enhancing factor 1 |
| 61 | 0.000377 | 48.8 | 73.7 | 1.51 | 228540_at | QKI | Quaking homolog, KH domain RNA binding (mouse) |
| 62 | 0.000386 | 24.1 | 20 | −1.21 | 221261_x_at | MAGED4/// MAGED4B | Melanoma antigen family D, 4B///melanoma antigen family D, 4 |
| 63 | 0.000393 | 8.3 | 9.9 | 1.19 | 1562458_at | UBE2W | Ubiquitin-conjugating enzyme E2W (putative) |
| 64 | 0.000399 | 28.9 | 40.2 | 1.39 | 227403_at | PIGX | Phosphatidylinositol glycan anchor biosynthesis, class X |
| 65 | 0.000406 | 21.6 | 27.6 | 1.28 | 226827_at | TMEM165 | Transmembrane protein 165 |
| 66 | 0.000418 | 61.4 | 54.1 | −1.13 | 1568691_at | EST9 | CDNA clone IMAGE: 3613441 |
| 67 | 0.000444 | 31 | 51.9 | 1.67 | 230343_at | EST10 | Transcribed locus |
| 68 | 0.000445 | 10.3 | 8.2 | −1.26 | 212650_at | EHBP1 | EH domain binding protein 1 |
| 69 | 0.000448 | 168.6 | 306.1 | 1.82 | 238066_at | RBP7 | Retinol binding protein 7, cellular |
| 70 | 0.000451 | 69.6 | 97.7 | 1.40 | 213292_s_at | SNX13 | Sorting nexin 13 |
| 71 | 0.000463 | 38.7 | 63.7 | 1.65 | 228362_s_at | FAM26F | Family with sequence similarity 26, member F |
| 72 | 0.000477 | 30 | 23.6 | −1.27 | 236139_at | EST11 | Transcribed locus |
| 73 | 0.000486 | 15.4 | 20.2 | 1.31 | 220775_s_at | UEVLD | UEV and lactate/malate dehydrogenase domains |
| 74 | 0.000493 | 55.2 | 46.9 | −1.18 | 221189_s_at | TARS2 | Threonyl-tRNA synthetase 2, mitochondrial (putative) |
| 75 | 0.000497 | 24.5 | 20 | −1.23 | 210150_s_at | LAMA5 | Laminin, alpha 5 |
| 76 | 0.000509 | 49.3 | 41.2 | −1.20 | 211304_x_at | KCNJ5 | Potassium inwardly-rectifying channel, subfamily J, member 5 |
| 77 | 0.000524 | 5.4 | 4.7 | −1.15 | 233609_at | PTPRK | Protein tyrosine phosphatase, receptor type, K |
| 78 | 0.000538 | 12.2 | 17.6 | 1.44 | 202422_s_at | ACSL4 | Acyl-CoA synthetase long-chain family member 4 |
| 79 | 0.000539 | 360.3 | 442.2 | 1.23 | 225284_at | DNAJC3/// LOC144871 | DnaJ (Hsp40) homolog, subfamily C, member 3/// hypothetical protein LOC144871 |
| 80 | 0.000549 | 10.4 | 8.7 | −1.20 | 204983_s_at | GPC4 | Glypican 4 |
| 81 | 0.000555 | 15.5 | 13.4 | −1.16 | 231318_at | C15orf51 | Chromosome 15 open reading frame 51 |
| 82 | 0.000564 | 59.4 | 83.9 | 1.41 | 208158_s_at | OSBPL1A | Oxysterol binding protein-like 1A |

TABLE A-continued

Differentially expressed consensus genes for mild CAN for both Test
Mild CAN = CAN Banff Class 1; No evidence of CAN = CAN Banff Class 0
Probesets with positive fold changes are upregulated in mild CAN

|  | Parametric p-value | Geom mean of intensities in class 1: Banff 0 | Geom mean of intensities in class 2: Banff 1 | Fold Change | Probe Set ID | Gene Symbol | Gene Title |
| --- | --- | --- | --- | --- | --- | --- | --- |
| 83 | 0.000571 | 9.2 | 8.1 | −1.14 | 205542_at | STEAP1 | Six transmembrane epithelial antigen of the prostate 1 |
| 84 | 0.000573 | 186.9 | 235.8 | 1.26 | 218905_at | INTS8 | Integrator complex subunit 8 |
| 85 | 0.000588 | 100.3 | 177.5 | 1.77 | 212820_at | DMXL2 | Dmx-like 2 |
| 86 | 0.000594 | 160.5 | 341.8 | 2.13 | 215049_x_at | CD163 | CD163 molecule |
| 87 | 0.000595 | 20.8 | 34.4 | 1.65 | 206674_at | FLT3 | Fms-related tyrosine kinase 3 |
| 88 | 0.000595 | 52.3 | 40.2 | −1.30 | 233487_s_at | LRRC8A | Leucine rich repeat containing 8 family, member A |
| 89 | 0.000607 | 17.5 | 21.1 | 1.21 | 33197_at | MYO7A | Myosin VIIA |
| 90 | 0.000642 | 26.5 | 23.5 | −1.13 | 203793_x_at | PCGF2 | Polycomb group ring finger 2 |
| 91 | 0.000648 | 9.1 | 8.2 | −1.11 | 1566935_at | TYRO3P | TYRO3P protein tyrosine kinase pseudogene |
| 92 | 0.000663 | 10.8 | 15.2 | 1.41 | 203767_s_at | STS | Steroid sulfatase (microsomal), isozyme S |
| 93 | 0.000668 | 303.5 | 421.8 | 1.39 | 226136_at | GLIPR1 | GLI pathogenesis-related 1 (glioma) |
| 94 | 0.00067 | 52.1 | 81.1 | 1.56 | 216252_x_at | FAS | Fas (TNF receptor superfamily, member 6) |
| 95 | 0.000694 | 244.7 | 420.5 | 1.72 | 221724_s_at | CLEC4A | C-type lectin domain family 4, member A |
| 96 | 0.000696 | 11.6 | 13.1 | 1.13 | 230419_at | FLJ37644 | Hypothetical gene supported by AK094963 |
| 97 | 0.000701 | 26.8 | 33.2 | 1.24 | 225778_at | FUT1 | Fucosyltransferase ! (galactoside 2-alpha-L-fucosyltransferase, H blood group) |
| 98 | 0.000702 | 14.8 | 10.3 | −1.44 | 216063_at | HBBP1 | Hemoglobin, beta pseudogene 1 |
| 99 | 0.000745 | 6.9 | 6.2 | −1.11 | 207516_at | CHRNB4 | Cholinergic receptor, nicotinic, beta 4 |
| 100 | 0.000749 | 21.8 | 17.3 | −1.26 | 216910_at | XPNPEP2 | X-prolyl aminopeptidase (aminopeptidase P) 2, membrane-bound |
| 101 | 0.00075 | 14.7 | 12.5 | −1.18 | 1555655_at | OR10A4 | Olfactory receptor, family 10, subfamily A, member 4 |
| 102 | 0.000755 | 266.1 | 339 | 1.27 | 225606_at | BCL2L11 | BCL2-like 11 (apoptosis facilitator) |
| 103 | 0.000768 | 17 | 14.8 | −1.15 | 207967_at | VPS45 | Vacuolar protein sorting 45 homolog (S. cerevisiae) |
| 104 | 0.000775 | 253.9 | 336.8 | 1.33 | 219079_at | CYB5R4 | Cytochrome b5 reductase 4 |
| 105 | 0.000803 | 94.6 | 134.1 | 1.42 | 222498_at | AZI2 | 5-azacytidine induced 2 |
| 106 | 0.00081 | 570.4 | 686.2 | 1.20 | 210817_s_at | CALCOCO2 | Calcium binding and coiled-coil domain 2 |
| 107 | 0.00082 | 344.4 | 494.4 | 1.44 | 211404_s_at | APLP2 | Amyloid beta (A4) precursor-like protein 2 |
| 108 | 0.000824 | 9.6 | 16.4 | 1.71 | 1562481_at | EST12 | — |
| 109 | 0.000834 | 78.3 | 105.7 | 1.35 | 203693_s_at | E2F3 | E2F transcription factor 3 |
| 110 | 0.00084 | 23.2 | 33.6 | 1.45 | 205841_at | JAK2 | Janus kinase 3 (a protein tyrosine kinase) |
| 111 | 0.000847 | 10.2 | 9.1 | −1.12 | 1553504_at | MRGPRX4 | MAS-related GPR, member X4 |
| 112 | 0.00085 | 140.6 | 212.9 | 1.51 | 203139_at | DAPK1 | Death-associated protein kinase 1 |
| 113 | 0.000864 | 186.1 | 235.2 | 1.26 | 226850_at | SUMF1 | Sulfatase modifying factor 1 |
| 114 | 0.000896 | 4.9 | 5.4 | 1.10 | 230684_at | GTPBP10 | GTP-binding protein 10 (putative) |
| 115 | 0.000907 | 34.8 | 21.7 | −1.60 | 228802_at | RBPMS2 | RNA binding protein with multiple splicing 2 |
| 116 | 0.000969 | 7.6 | 6.8 | −1.12 | 204596_s_at | STC1 | Stanniocalcin 1 |
| 117 | 0.000972 | 45.3 | 57 | 1.26 | 228061_at | CCDC126 | Coiled-coil domain containing 126 |
| 118 | 0.000979 | 31.4 | 22.6 | −1.39 | 244876_at | EST13 | — |
| 119 | 0.000992 | 12.4 | 10.7 | −1.16 | 233015_at | MBNL1 | Muscleblind-like (Drosophila) |
| 120 | 0.001033 | 21.6 | 14.5 | −1.49 | 234284_at | GNG8 | Guanine nucleotide binding protein (G protein), gamma 8 |
| 121 | 0.001036 | 38.2 | 24.8 | −1.54 | 1560262_at | EST14 | Homo sapiens, clone IMAGE:5751523, mRNA |
| 122 | 0.001037 | 5.4 | 4.8 | −1.13 | 1562902_at | EST15 | Homo sapiens, clone IMAGE: 5176738, mRNA |
| 123 | 0.001045 | 1215.1 | 2084.9 | 1.72 | 205863_at | S100A12 | S100 calcium binding protein A12 |
| 124 | 0.001057 | 37.8 | 31.9 | −1.18 | 222302_at | EST16 | — |
| 125 | 0.001065 | 44.9 | 51.1 | 1.14 | 212932_at | RAB3GAP1 | RAB3 GTPase activating protein subunit 1 (catalytic) |
| 126 | 0.001066 | 36.3 | 49.6 | 1.37 | 233924_s_at | EXOC6 | Exocyst complex component 6 |
| 127 | 0.001087 | 34.5 | 41.5 | 1.20 | 230209_at | EST17 | CDNA FLI36477 fis, clone THYMU2017158 |
| 128 | 0.001103 | 498.4 | 419.3 | −1.19 | 41047_at | C9orf16 | Chromosome 9 open reading frame 16 |
| 129 | 0.001136 | 57.1 | 40.8 | −1.40 | 200884_at | CKB | Creatine kinase, brain |
| 130 | 0.001137 | 177 | 245.9 | 1.39 | 219157_at | KLHL2 | Kelch-like 2, Mayven (Drosophila) |
| 131 | 0.001153 | 7.3 | 6.4 | −1.14 | 207818_s_at | HTR7 | 5-hydroxytryptamine (serotonin) receptor 7 (adenylate cyclase-coupled) |
| 132 | 0.001162 | 13.3 | 16.1 | 1.21 | 234977_at | ZADH2 | Zinc binding alcohol dehydrogenase, domain containing 2 |
| 133 | 0.001164 | 4.6 | 4.3 | −1.07 | 238391_at | EST18 | Transcribed locus |
| 134 | 0.001173 | 125.2 | 160.3 | 1.28 | 222759_at | SUV420H1 | Suppressor of variegation 4-20 homolog 1 (Drosophila) |
| 135 | 0.001197 | 16.5 | 13.5 | −1.22 | 233962_at | C20orf120 | Chromosome 20 open reading frame 120 |
| 136 | 0.001212 | 183 | 250.9 | 1.37 | 204526_s_at | TBC1D8 | TBC1 domain family, member 8 (with GRAM domain) |
| 137 | 0.001214 | 39.9 | 31.5 | −1.27 | 235417_at | SPOCD1 | SPOC domain containing 1 |
| 138 | 0.001228 | 67.2 | 87.8 | 1.31 | 1552472_a_at | CENTB2 | Centaurin, beta 2 |
| 139 | 0.001232 | 423 | 513.3 | 1.21 | 200768_s_at | MAT2A | Methionine adenosyltransferase II, alpha |
| 140 | 0.001246 | 17 | 14.7 | −1.16 | 229536_at | REC8 | REC8 homolog (yeast) |
| 141 | 0.001283 | 1790.8 | 2281.3 | 1.27 | 204220_at | GMFG | Glia maturation factor, gamma |
| 142 | 0.001291 | 41.6 | 35.4 | −1.18 | 234958_at | EST19 | Clone HQ0352 PRO0352 |
| 143 | 0.001294 | 1519.9 | 1803 | 1.19 | 207168_s_at | H2AFY | H2A histone family, member Y |
| 144 | 0.001329 | 9.9 | 8.3 | −1.19 | 1557235_at | EST20 | CDNA FLI44051 fis, clone TESTI4033433 |
| 145 | 0.001329 | 7.7 | 6.8 | −1.13 | 207120_at | ZNF667 | Zinc finger protein 667 |
| 146 | 0.001348 | 12 | 15.3 | 1.28 | 226688_at | C3orf23 | Chromosome 3 open reading frame 23 |
| 147 | 0.001363 | 201.6 | 311.2 | 1.54 | 224374_s_at | EMILIN2 | Elastin microfibril interfacer 2 |

TABLE A-continued

Differentially expressed consensus genes for mild CAN for both Test
Mild CAN = CAN Banff Class 1; No evidence of CAN = CAN Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 148 | 0.001364 | 79.4 | 48.9 | −1.62 | 244523_at | MMD | Monocyte to macrophage differentiation-associated |
| 149 | 0.001415 | 10.4 | 9.1 | −1.14 | 226533_at | HINT3 | Histidine triad nucleotide binding protein 3 |
| 150 | 0.001421 | 505.7 | 358.5 | −1.41 | 202074_s_at | OPTN | Optineurin |
| 151 | 0.001438 | 10.9 | 9.6 | −1.14 | 234372_at | LOC644728 | Similar to Glyceraldehyde-3-phosphate dehydrogenase (GAPDH) (38 kDa 8FA-dependent ADP-ribosylation substrate) (BARS-38) |
| 152 | 0.001448 | 239.8 | 331.7 | 1.38 | 202192_s_at | GAS7 | Growth arrest-specific 7 |
| 153 | 0.001464 | 16.6 | 20.7 | 1.25 | 1559052_s_at | PAK2 | p21 (CDKN1A)-activated kinase 2 |
| 154 | 0.001472 | 32.5 | 47.6 | 1.46 | 223304_at | SLC37A3 | Solute carrier family 37 (glycerol-3-phosphate transporter), member 3 |
| 155 | 0.001491 | 43.1 | 58.5 | 1.36 | 213582_at | ATP11A | ATPase, Class VI, type 11A |
| 156 | 0.001507 | 6.5 | 5.8 | −1.12 | 233770_at | EST21 | CDNA FLI12077 fis, clone HEMBB1002453 |
| 157 | 0.001515 | 14.1 | 12.7 | −1.11 | 234627_at | FLJ21408 | Hypothetical gene supported by AK025061 |
| 158 | 0.00152 | 815.3 | 1047.6 | 1.28 | 209007_s_at | C1orf63 | Chromosome 1 open reading frame 63 |
| 159 | 0.00153 | 15.6 | 11.2 | −1.39 | 214502_at | HIST1H2BJ | Histone cluster 1, H2bj |
| 160 | 0.001533 | 206.6 | 140.7 | −1.47 | 202124_s_at | TRAK2 | Trafficking protein, kinesin binding 2 |
| 161 | 0.001538 | 16.1 | 12.9 | −1.25 | 223709_at | WNT10A | Wingless-type MMTV integration site family, member 10A |
| 162 | 0.001544 | 143.1 | 194.3 | 1.36 | 219132_at | PELI2 | Pellino homolog 2 (Drosophila) |
| 163 | 0.001561 | 556.9 | 684.6 | 1.23 | 217492_s_at | LOC731292///PTEN///PTENP1 | Phosphatase and tensin homolog (mutated in multiple advanced cancers 1)///phosphatase and tensin homolog (mutated in multiple advanced cancers 1), pseudogene 1///similar to Phosphatidylinositol-3,4,5-trisphosphate 3-phosphatase and dual-specificity protein phosphatase PTEN (Phosphatase and tensin homolog) (Mutated in multiple advanced cancers1) |
| 164 | 0.001562 | 7.4 | 6.7 | −1.10 | 241226_at | EST22 | Transcribed locus |
| 165 | 0.001565 | 12.1 | 10.6 | −1.14 | 231965_at | FAM113A | Family with sequence similarity 113, member A |
| 166 | 0.00157 | 39.4 | 69.3 | 1.76 | 207605_x_at | ZNF117 | Zinc finger protein 117 |
| 167 | 0.001602 | 22.4 | 19.4 | −1.15 | 232249_at | FMNL3 | Formin-like 3 |
| 168 | 0.001612 | 81.2 | 116 | 1.43 | 205698_s_at | MAP2K6 | Mitogen-activated protein kinase kinase 6 |
| 169 | 0.001613 | 110.4 | 140.3 | 1.27 | 229798_s_at | EST23 | — |
| 170 | 0.00162 | 21 | 17.7 | −1.19 | 219554_at | RHCG | Rh family, C glycoprotein |
| 171 | 0.001625 | 7 | 6.1 | −1.15 | 244690_at | EST24 | Transcribed locus |
| 172 | 0.00163 | 343.7 | 497.4 | 1.45 | 225919_s_at | C9orf72 | Chromosome 9 open reading frame 72 |
| 173 | 0.001642 | 74.3 | 101.7 | 1.37 | 213792_s_at | INSR | Insulin receptor |
| 174 | 0.001677 | 23.1 | 26.8 | 1.16 | 208328_s_at | MEF2A | Myocyte enhancer factor 2A |
| 175 | 0.00168 | 6.9 | 6.2 | −1.11 | 207362_at | SLC30A4 | Solute carrier family 30 (zinc transporter), member 4 |
| 176 | 0.001709 | 17.5 | 15.4 | −1.14 | 206521_s_at | GTF2A1 | General transcription factor IIA, 1, 19/37 kDa |
| 177 | 0.001735 | 100.2 | 142 | 1.42 | 218027_at | MRPL15 | Mitochondrial ribosomal protein L15 |
| 178 | 0.001737 | 19.6 | 22.8 | 1.16 | 224198_at | ELA1 | Elastase 1, pancreatic |
| 179 | 0.001741 | 69.6 | 97.1 | 1.40 | 212572_at | STK38L | Serine/threonine kinase 38 like |
| 180 | 0.001743 | 22.3 | 18.6 | −1.20 | 206993_at | ATP5S | ATP synthase, H+ transporting, mitochondrial F0 complex, subunit s (factor B) |
| 181 | 0.001788 | 45.4 | 36.5 | 1.24 | 203479_s_at | OTUD4 | OTU domain containing 4 |
| 182 | 0.001835 | 13.4 | 11 | −1.22 | 232820_s_at | FAM112A | Family with sequence similarity 112, member A |
| 183 | 0.001854 | 7.2 | 6.6 | 1.09 | 1558621_at | CABLES1 | Cdk5 and Abl enzyme substrate 1 |
| 184 | 0.001854 | 59.1 | 49.6 | −1.19 | 220765_s_at | LIMS2 | LIM and senescent cell antigen-like domains 2 |
| 185 | 0.001859 | 24.3 | 20.6 | −1.18 | 205477_s_at | AMBP | Alpha-1-microglobulin/bikunin precursor |
| 186 | 0.00189 | 102.8 | 59 | 0.57 | 207826_s_at | ID3 | Inhibitor of DNA binding 3, dominant negative helix-loop-helix protein |
| 187 | 0.001892 | 10.5 | 17.8 | 1.70 | 209992_at | PFKFB2 | 6-phosphofructo-2-kinase/fructose-2,6-biphosphatase 2 |
| 188 | 0.001928 | 207.8 | 151.9 | −1.37 | 201841_s_at | HSPB1 | Heat shock 27 kDa protein 1 |
| 189 | 0.001936 | 61.4 | 83.5 | 1.36 | 210768_x_at | TMCO1 | Transmembrane and coiled-coil domains 1 |
| 190 | 0.001951 | 43.1 | 63.6 | 1.48 | 242794_at | MAML3 | Mastermind-like 3 (Drosophila) |
| 191 | 0.001976 | 58.7 | 79.2 | 1.35 | 213379_at | COQ2 | Coenzyme Q2 homolog, prenyltransferase (yeast) |
| 192 | 0.001983 | 425.9 | 650.8 | 1.53 | 202446_s_at | PLSCR1 | Phospholipid scramblase 1 |
| 193 | 0.001984 | 24.7 | 28.7 | 1.16 | 204210_s_at | PCYT1A | Phosphate cytidylyltransferase 1, choline, alpha |
| 194 | 0.001993 | 31.8 | 58.3 | 1.83 | 236898_at | EST25 | Transcribed locus. strongly similar to XP_0011011634.1 similar to tripartite motif-containing 25 (Macaca mulatta) |
| 195 | 0.002 | 8.8 | 7.4 | −1.19 | 242661_x_at | ALS2CR12 | Amyotrophic lateral sclerosis 2 (juvenile) chromosome region, candidate 12 |
| 196 | 0.002013 | 19.4 | 15.4 | −1.26 | 1558773_s_at | RANBP10 | RAN binding protein 10 |
| 197 | 0.002032 | 63.6 | 79.5 | 1.25 | 218896_s_at | C17orf85 | Chromosome 17 open reading frame 85 |

TABLE A-continued

Differentially expressed consensus genes for mild CAN for both Test
Mild CAN = CAN Banff Class 1; No evidence of CAN = CAN Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 198 | 0.002033 | 27.8 | 37.2 | 1.34 | 220865_s_at | PDSS1 | Prenyl (decaprenyl) diphosphate synthase, subunit 1 |
| 199 | 0.002038 | 214.1 | 282.4 | 1.32 | 224511_s_at | TXNDC17 | Thioredoxin domain containing 17 |
| 200 | 0.002045 | 7.6 | 6.4 | -1.19 | 243347_at | EST26 | — |
| 201 | 0.002054 | 8.1 | 7 | -1.16 | 236336_at | EST27 | CDNA clone IMAGE:4796690 |
| 202 | 0.002098 | 153.9 | 205.6 | 1.34 | 224983_at | SCARB2 | Scavenger receptor class B, member 2 |
| 203 | 0.002099 | 30.1 | 26 | -1.16 | 1569144_a_at | LOC653325/// MGC59937 | Similar to RIKEN cDNA 2310002J15 gene///hypothetical LOC653325 |
| 204 | 0.002104 | 15.9 | 13.7 | -1.16 | 234511_at | C20orf86 | Chromosome 20 open reading frame 86 |
| 205 | 0.002106 | 20.3 | 17.2 | -1.18 | 237254_at | SLC5A11 | Solute carrier family 5 (sodium/glucose cotransporter), member 11 |
| 206 | 0.002112 | 9.3 | 10.5 | 1.13 | 231310_at | EST28 | Transcribed locus |
| 207 | 0.002171 | 15.7 | 13 | -1.21 | 244226_s_at | EST29 | — |
| 208 | 0.0022 | 13.3 | 11.4 | -1.17 | 230957_at | PCDHB19P | Protocadherin beta 19 pseudogene |
| 209 | 0.002206 | 10.8 | 9.5 | -1.14 | 232321_at | MUC17 | Mucin 17, cell surface associated |
| 210 | 0.00221 | 27.4 | 19.8 | -1.38 | 235557_at | LOC150763 | Hypothetical protein LOC150763 |
| 211 | 0.002218 | 11251.4 | 8508.5 | -1.32 | 214414_x_at | HBA2 | Hemoglobin, alpha 2 |
| 212 | 0.00222 | 16.1 | 13.8 | -1.17 | 1558118_at | DGCR5 | DiGeorge syndrome critical region gene 5 (non-coding) |
| 213 | 0.002223 | 18.1 | 15.9 | -1.14 | 231994_at | CHDH | Choline dehydrogenase |
| 214 | 0.002229 | 29.1 | 34.7 | 1.19 | 212710_at | CAMSAP1 | Calmodulin regulated spectrin-associated protein 1 |
| 215 | 0.002253 | 94.3 | 73.7 | -1.28 | 243579_at | MSI2 | Musashi homolog 2 (Drosophila) |
| 216 | 0.002256 | 446.2 | 305.3 | -1.46 | 200702_s_at | DDX24 | DEAD (Asp-Glu-Ala-Asp) box polypeptide 24 |
| 217 | 0.002266 | 94.9 | 124.4 | 1.31 | 227046_at | SLC39A11 | Solute carrier family 39 (Metal ion transporter), member 11 |
| 218 | 0.002294 | 36 | 31.2 | -1.15 | 40020_at | CELSR3 | Cadherin, EGF LAG seven-pass G-type receptor 3 (flamingo homolog, Drosophila) |
| 219 | 0.002303 | 27.6 | 22.9 | -1.21 | 218903_s_at | OBFC2B | Oligonucleotide/oligosaccharide-binding fold containing 2B |
| 220 | 0.002329 | 5.5 | 6.7 | 1.22 | 223861_at | HORMAD1 | HORMA domain containing 1 |
| 221 | 0.002348 | 508.5 | 692.2 | 1.36 | 201926_s_at | CD55 | CD55 molecule, decay accelerating factor for complement (Cromer blood group) |
| 222 | 0.00235 | 1265.9 | 1098.5 | -1.15 | 209075_s_at | ISCU | Iron-sulfur cluster scaffold homolog (E.coli) |
| 223 | 0.002351 | 7.1 | 6 | -1.18 | 231721_at | JAM3 | Junctional adhesion molecule 3 |
| 224 | 0.002354 | 8.2 | 7.4 | -1.11 | 237505_at | EST30 | Transcribed locus |
| 225 | 0.002368 | 67.4 | 100.4 | 1.49 | 201952_at | ALCAM | Activated leukocyte cell adhesion molecule |
| 226 | 0.002389 | 10 | 8.7 | 1.15 | 211896_s_at | DCN | Decorin |
| 227 | 0.002394 | 40.2 | 31.8 | -1.26 | 216080_s_at | FADS3 | Fatty acid desaturase 3 |
| 228 | 0.002427 | 252.5 | 326.4 | 1.29 | 202277_at | SPTLC1 | Serine palmitoyltransferase, long chain base subunit 1 |
| 229 | 0.002435 | 37.7 | 56.3 | 1.49 | 208488_s_at | CR1 | Complement component (3b/4b) receptor 1 (Knops blood group) |
| 230 | 0.002437 | 100.3 | 135.1 | 1.35 | 213868_s_at | DHRS7 | Deydrogenase/reductase (SDR family) member 7 |
| 231 | 0.002443 | 314.9 | 419.1 | 1.33 | 225921_at | NIN | Ninein (GSK3B interacting protein) |
| 232 | 0.002447 | 56.7 | 82.8 | 1.46 | 233329_s_at | KRCC1 | Lysine-rich coiled-coil 1 |
| 233 | 0.002472 | 28.3 | 24.6 | -1.15 | 232663_s_at | LOC390595 | Similar to ubiquitin-associated protein 1 (predicted) |
| 234 | 0.002474 | 88.9 | 143.5 | 1.61 | 204150_at | STAB1 | Stabilin 1 |
| 235 | 0.002511 | 10 | 11.5 | 1.15 | 219831_at | CDKL3 | Cyclin-dependent kinase-like 3 |
| 236 | 0.002528 | 69.8 | 101.9 | 1.46 | 216202_s_at | SPTLC2 | Serine palmitoyltransferase, long chain base subunit 2 |
| 237 | 0.002536 | 28.7 | 24.3 | -1.18 | 233381_at | RUFY1 | RUN and FYVE domain containing 1 |
| 238 | 0.002552 | 67.7 | 84 | 1.24 | 222842_at | EIF2C4 | Eukaryotic translation initiation factor 2C, 4 |
| 239 | 0.002566 | 13.7 | 10.6 | -1.29 | 1554413_s_at | RUNDC2B/// RUNDC2C | RUN domain containing 2B///RUN domain containing 2C |
| 240 | 0.002598 | 13.9 | 12.2 | -1.14 | 202403_s_at | COL1A2 | Collagen, type 1, alpha 2 |
| 241 | 0.002603 | 531.4 | 440.6 | -1.21 | 210950_s_at | FDFT1 | Farnesyl-diphosphate farnesyltransferase 1 |
| 242 | 0.002605 | 10.1 | 8.5 | -1.19 | 215742_at | EST31 | CDNA FLI12157 fis, clone MAMMA1000500 |
| 243 | 0.002672 | 35.9 | 42.2 | 1.18 | 221567_at | NOL3 | Nucleolar protein 3 (apoptosis repressor with CARD domain) |
| 244 | 0.002691 | 16 | 12 | -1.33 | 203151_at | MAP1A | Microtubule-associated protein 1A |
| 245 | 0.002693 | 406.6 | 540.5 | 1.33 | 208864_s_at | TXN | Thioredoxin |
| 246 | 0.002706 | 83 | 62.3 | -1.33 | 201072_s_at | SMARCC1 | SWI/SNF related, matrix associated, actin dependent regulator of chromatin, subfamily c, member 1 |
| 247 | 0.002715 | 77.7 | 63.5 | -1.22 | 211358_s_at | CIZ1 | CDKN1A interacting zinc finger protein 1 |
| 248 | 0.002724 | 11.1 | 13.7 | 1.23 | 205416_s_at | ATXN3 | Ataxin 3 |
| 249 | 0.002731 | 27 | 23.9 | -1.13 | 244694_at | LOC402665 | hCG1651476 |
| 250 | 0.002731 | 94.6 | 135.6 | 1.43 | 212511_at | PICALM | Phosphatidylinositol binding clathrin assembly protein |
| 251 | 0.002736 | 81.1 | 112.4 | 1.39 | 223978_s_at | CRLS1 | Cardiolipin synthase 1 |
| 252 | 0.002737 | 12.1 | 10.7 | -1.13 | 210923_at | SLC1A7 | Solute carrier family 1 (glutamate transporter), member 7 |

TABLE A-continued

Differentially expressed consensus genes for mild CAN for both Test
Mild CAN = CAN Banff Class 1; No evidence of CAN = CAN Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 253 | 0.002738 | 5.6 | 5.1 | −1.10 | 204320_at | COL11A1 | Collagen, type XI, alpha 1 |
| 254 | 0.002739 | 61 | 83.3 | 1.37 | 209666_s_at | CHUK | Conserved helix-loop-helix ubiquitous kinase |
| 255 | 0.002747 | 29.9 | 24.5 | −1.22 | 238097_at | EST32 | — |
| 256 | 0.002749 | 10.1 | 8.6 | −1.17 | 205295_at | CKMT2 | Creatine kinase, mitochondrial 2 (sarcomeric) |
| 257 | 0.002773 | 240.1 | 331.4 | 1.38 | 1555797_a_at | ARPC5 | Actin related protein 2/3 complex, subunit 5, 16 kDa |
| 258 | 0.002776 | 32.5 | 28.1 | −1.16 | 235402_at | C11orf66 | Chromosome 11 open reading frame 66 |
| 259 | 0.002793 | 30.8 | 25.5 | 1.21 | 216562_at | EST33 | — |
| 260 | 0.002823 | 19.6 | 17.1 | −1.15 | 1553967_at | ADAT3 | Adenosine deaminase, tRNA-specific 3, TAD3 homolog (S. cerevisiae) |
| 261 | 0.002831 | 883.8 | 1069.3 | 1.21 | 226525_at | EST34 | Transcribed locus |
| 262 | 0.002853 | 65.1 | 109.4 | 1.68 | 220034_at | IRAK3 | Interleukin-1 receptor-associated kinase 3 |
| 263 | 0.002856 | 7.7 | 7.1 | −1.08 | 1563656_at | EST35 | MRNA; cDNA DKFZp586H1217 (from clone DKFZp586H1217) |
| 264 | 0.002859 | 60.5 | 53.8 | −1.12 | 233235_x_at | EST36 | CDNA: FLI21443 fis, clone COL04430 |
| 265 | 0.002876 | 5 | 5.5 | 1.10 | 1558640_a_at | LOC728411 | Similar to Beta-glucuronidase precursor |
| 266 | 0.00288 | 143.4 | 216.8 | 1.51 | 204646_at | DPYD | Dihydropyrimidine dehydrogenase |
| 267 | 0.002888 | 52.8 | 83.6 | 1.58 | 207719_x_at | CEP170 | Centrosomal protein 170 kDa |
| 268 | 0.00289 | 41.3 | 50.9 | 1.23 | 228791_at | C15orf38 | Chromosome 15 open reading frame 38 |
| 269 | 0.002915 | 17.6 | 15 | −1.17 | 240705_at | CYP19A1 | Cytochrome P450, family 19, subfamily A, polypeptide 1 |
| 270 | 0.002927 | 50.7 | 42.9 | −1.18 | 218725_at | SLC25A22 | Solute carrier family 25 (mitochondrial carrier: glutamate), member 22 |
| 271 | 0.002996 | 105.1 | 163.4 | 1.55 | 201328_at | ETS2 | v-ets erythroblastosis virus E26 oncogene homolog 2 (avian) |
| 272 | 0.002997 | 13.9 | 16.3 | 1.17 | 239332_at | EST37 | Homo sapiens, clone IMAGE: 3897156, mRNA |
| 273 | 0.00302 | 14 | 16.9 | 1.21 | 240394_at | EST38 | Transcribed locus |
| 274 | 0.003049 | 60.3 | 51.8 | −1.16 | 1556900_at | LOC149773 | Hypothetical protein LOC149773 |
| 275 | 0.003057 | 43.4 | 33.4 | −1.30 | 220588_at | BCAS4 | Breast carcinoma amplified sequence 4 |
| 276 | 0.003067 | 10.1 | 8.4 | −1.20 | 210127_at | RAB6B | RAB6B, member RAS oncogene family |
| 277 | 0.003068 | 5.5 | 4.9 | −1.12 | 1559450_at | EST39 | CDNA clone IMAGE: 5286225 |
| 278 | 0.003109 | 22 | 36.6 | 1.66 | 1558920_at | EST40 | CDNA FLI43417 fis, clone OCBBF2026025 |
| 279 | 0.003116 | 9.2 | 8.2 | −1.12 | 206847_s_at | HOXA7 | Homeobox A7 |
| 280 | 0.003117 | 12.9 | 11.3 | −1.14 | 216303_s_at | MTMR1 | Myotubularin related protein 1 |
| 281 | 0.003131 | 14 | 12.3 | −1.14 | 216799_at | EST41 | MRNA; cDNA DKFZp547G044 (from clone DKFZp547G044) |
| 282 | 0.003131 | 5.8 | 5.3 | −1.09 | 242130_at | EST42 | Transcribed locus |
| 283 | 0.003145 | 10.6 | 9.4 | −1.13 | 1562106_at | EST43 | Homo sapiens, clone IMAGE: 5240933, mRNA |
| 284 | 0.003147 | 40.2 | 46.9 | 1.17 | 224416_s_at | MED28 | Mediator complex subunit 28 |
| 285 | 0.003153 | 441.7 | 716.5 | 1.62 | 203799_at | CD302 | CD302 molecule |
| 286 | 0.00318 | 23.2 | 19.5 | −1.19 | 243062_at | FLCN | Folliculin |
| 287 | 0.003188 | 15.1 | 19.7 | 1.30 | 239574_at | EST44 | Transcribed locus |
| 288 | 0.003189 | 5.7 | 5.2 | −1.10 | 1559518_at | HSD17B12 | Hydroxysteroid (17-beta) dehydrogenase 12 |
| 289 | 0.0032 | 27.3 | 38.8 | 1.42 | 207601_at | SULT1B1 | Sulfotransferase family, cytosolic, 1B, member 1 |
| 290 | 0.003219 | 14.6 | 13 | −1.12 | 219576_at | MAP7D3 | MAP7 domain containing 3 |
| 291 | 0.003229 | 98.4 | 127.1 | 1.29 | 209234_at | KIF1B | Kinesin family member 1B |
| 292 | 0.003234 | 151.4 | 100.7 | −1.50 | 225775_at | TSPAN33 | Tetraspanin 33 |
| 293 | 0.003255 | 10.8 | 12.9 | 1.19 | 238921_at | LOC641767/// LOC644794 | Hypothetical protein LOC641767///hypothetical LOC644794 |
| 294 | 0.003276 | 5.2 | 5.8 | 1.12 | 236262_at | MMRN2 | Multimerin 2 |
| 295 | 0.003296 | 20.4 | 16.2 | −1.26 | 215526_at | EST45 | MRNA; cDNA DKFZp586C2020 (from clone DKFZp586C2020) |
| 296 | 0.003296 | 14.9 | 13.2 | −1.13 | 236914_at | EST46 | Transcribed locus, moderately similar to XP_001137307.1 hypothetical protein (Pantroglodytes) |
| 297 | 0.003306 | 43.6 | 58.4 | 1.34 | 236465_at | RNF175 | Ring finger protein 175 |
| 298 | 0.00334 | 106.2 | 210.1 | 1.98 | 204619_s_at | VCAN | Versican |
| 299 | 0.003365 | 15.3 | 12.5 | −1.22 | 243365_s_at | AUTS2 | Autism susceptibility candidate 2 |
| 300 | 0.003378 | 165.7 | 146 | −1.13 | 201618_x_at | GPAA1 | Glycosylphosphatidylinositol anchor attachment protein 1 homolog (yeast) |
| 301 | 0.003383 | 82.2 | 97.6 | 1.19 | 209445_x_at | C7orf44 | Chromosome 7 open reading frame 44 |
| 302 | 0.003388 | 66.1 | 101.4 | 1.53 | 1552485_at | LACTB | Lactamase, beta |
| 303 | 0.003393 | 6 | 5.5 | −1.09 | 1558010_s_at | SLC1A2 | Solute carrier family 1 (glial high affinity glutamate transporter), member 2 |
| 304 | 0.003404 | 8 | 11 | 1.38 | 225008_at | EST47 | CDNA FLI39064 fis, clone NT2RP7014583 |
| 305 | 0.003412 | 13.5 | 11.3 | −1.19 | 1560108_at | EST48 | CDNA FLI30757 fis, clone FEBRA2000468 |
| 306 | 0.003423 | 29.3 | 27.2 | −1.08 | 244055_at | EST49 | Transcribed locus |
| 307 | 0.003447 | 16.6 | 20 | 1.20 | 233750_s_at | C1orf25 | Chromosome 1 open reading frame 25 |
| 308 | 0.00346 | 5.4 | 5 | −1.08 | 220361_at | IQCH | IQ motif containing H |
| 309 | 0.003472 | 110 | 181.2 | 1.65 | 222303_at | EST50 | — |
| 310 | 0.003502 | 58.3 | 80.3 | 1.38 | 230937_at | LOC285835 | Hypothetical protein LOC285835 |
| 311 | 0.003535 | 39.4 | 52 | 1.32 | 207627_s_at | TFCP2 | Transcription factor CP2 |

TABLE A-continued

Differentially expressed consensus genes for mild CAN for both Test
Mild CAN = CAN Banff Class 1; No evidence of CAN = CAN Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 312 | 0.003539 | 20.3 | 17.5 | −1.16 | 1555752_at | STH | Saitohin |
| 313 | 0.003542 | 3088.2 | 3805.3 | 1.23 | 212501_at | CEBPB | CCAAT/enhancer binding protein (C/EBP), beta |
| 314 | 0.003551 | 6.2 | 5.7 | −1.09 | 244675_at | RGS8 | Regulator of G-protein signaling 8 |
| 315 | 0.003571 | 12.7 | 11.2 | −1.13 | 208275_x_at | UTF1 | Undifferentiated embryonic cell transcription factor 1 |
| 316 | 0.003572 | 397.4 | 524.7 | 1.32 | 210951_x_at | RAB27A | RAB27A, member RAS oncogene family |
| 317 | 0.003582 | 7.8 | 6.7 | −1.16 | 219840_s_at | TCL6 | T-cell leukemia/lymphoma 6 |
| 318 | 0.003626 | 124.1 | 166.3 | 1.34 | 219256_s_at | SH3TC1 | SH3 domain and tetratricopeptide repeats 1 |
| 319 | 0.003657 | 5.3 | 4.8 | −1.10 | 1558778_s_at | MKL2 | MKL/myocardin-like 2 |
| 320 | 0.00366 | 32.1 | 27.1 | −1.18 | 218480_at | AGBL5 | ATP/GTP binding protein-like 5 |
| 321 | 0.003672 | 118 | 176.7 | 1.50 | 204099_at | SMARCD3 | SWI/SNF related, matrix associated, actin dependent regulator of chromatin, subfamily d, member 3 |
| 322 | 0.003678 | 480.1 | 579 | 1.21 | 225750_at | EST51 | CDNA FLI14162 fis, clone NT2RM4002504 |
| 323 | 0.003715 | 50.7 | 43.5 | −1.17 | 214253_s_at | DTNB | Dystrobrevin, beta |
| 324 | 0.003718 | 12.1 | 10.8 | −1.12 | 243048_at | CECR7 | Cat eye syndrome chromosome region, candidate 7 |
| 325 | 0.003757 | 9 | 7.9 | −1.14 | 1556012_at | KLHDC7A | Kelch domain containing 7A |
| 326 | 0.003773 | 17.6 | 23.4 | 1.33 | 215285_s_at | PHTF1 | Putative homeodomain transcription factor 1 |
| 327 | 0.00378 | 64.4 | 81.7 | 1.27 | 231321_s_at | PHCA | Phytoceramidase, alkaline |
| 328 | 0.003783 | 5.4 | 4.9 | −1.10 | 238901_at | EST52 | Full length insert cDNA clone ZE01A04 |
| 329 | 0.003793 | 25.4 | 21.4 | −1.19 | 214595_at | KCNG1 | Potassium voltage-gated channel, subfamily G, member 1 |
| 330 | 0.0038 | 10.5 | 9.4 | −1.12 | 216470_x_at | PRSS1/// PRSS2/// PRSS3/// TRY6 | Protease, serine, 1 (trypsin1)///protease, serine, 2 (trypsin2)///protease, serine, 3 (mesotrypsin) trypsinogen 3 |
| 331 | 0.003819 | 36.6 | 59.4 | 1.62 | 204787_at | VSIG4 | V-set and immunoglobulin domain containing 4 |
| 332 | 0.003841 | 11.7 | 10.2 | −1.15 | 216101_at | EST53 | Full length insert cDNA clone YR67C11 |
| 333 | 0.003845 | 51 | 75.1 | 1.47 | 224862_at | GNAQ | Guanine nucleotide binding protein (G protein), q polypeptide |
| 334 | 0.003873 | 17.6 | 23.6 | 1.34 | 234664_at | LOC284701 | Hypothetical protein LOC284701 |
| 335 | 0.003878 | 16.8 | 14 | −1.20 | 202796_at | SYNPO | Synaptopodin |
| 336 | 0.003884 | 11.4 | 10 | −1.14 | 238217_at | EST54 | Transcribed locus |
| 337 | 0.003905 | 559.2 | 823.8 | 1.47 | 209184_s_at | IRS2 | Insulin receptor substrate 2 |
| 338 | 0.003905 | 5.6 | 5.2 | −1.08 | 1565578_at | EST55 | CDNA FLI34486 fis, clone HLUNG2004217 |
| 339 | 0.003909 | 202.6 | 269.2 | 1.33 | 217823_s_at | UBE2J1 | Ubiquitin-conjugating enzyme E2, J1 (UBC6 homolog, yeast) |
| 340 | 0.003952 | 7 | 6.2 | −1.13 | 240873_x_at | DAB2 | Disabled homolog 2, mitogen-responsive phosphoprotein (Drosophila) |
| 341 | 0.003967 | 206.9 | 281.1 | 1.36 | 212795_at | KIAA1033 | KIAA1033 |
| 342 | 0.003968 | 36 | 48.9 | 1.36 | 239085_at | EST56 | Transcribed locus |
| 343 | 0.003972 | 110.8 | 171.2 | 1.55 | 223423_at | GPR160 | G protein-coupled receptor 160 |
| 344 | 0.003992 | 12.3 | 10.8 | −1.14 | 238917_s_at | MGC24039 | Hypothetical protein MGC24039 |
| 345 | 0.003999 | 36.9 | 48.4 | 1.31 | 226395_at | LOC286170 | Hypothetical protein LOC286170 |
| 346 | 0.004021 | 155.6 | 222.8 | 1.43 | 215000_s_at | FEZ2 | Fasciculation and elongation protein zeta 2 (zygin II) |
| 347 | 0.004032 | 196.3 | 235.6 | 1.20 | 203605_at | SRP54 | Signal recognition particle 54 kDa |
| 348 | 0.004054 | 7.7 | 6.6 | −1.17 | 242805_at | EST57 | — |
| 349 | 0.004085 | 50.4 | 66.2 | 1.31 | 204043_at | TCN2 | Transcobalamin II; macrocytic anemia |
| 350 | 0.004142 | 9.8 | 11.4 | 1.16 | 237845_at | EST58 | Transcribed locus, moderately similar to XP_001103240.1 similar to kinesin family member 27 (Macaca mulatta) |
| 351 | 0.004144 | 28.5 | 22.5 | −1.27 | 1569499_at | EST59 | CDNA clone IMAGE:3840913 |
| 352 | 0.004179 | 21.1 | 18.5 | −1.14 | 217876_at | GTF3C5 | General transcription factor IIIC, polypeptide 5, 63 kDa |
| 353 | 0.004185 | 9.9 | 15.3 | 1.55 | 223660_at | ADORA3 | Adenosine A3 receptor |
| 354 | 0.004186 | 5.8 | 6.3 | 1.09 | 231160_at | EST60 | Transcribed locus |
| 355 | 0.00419 | 9.7 | 15.7 | 1.62 | 236901_at | EST61 | Transcribed locus |
| 356 | 0.0042 | 20.9 | 18 | −1.16 | 215979_s_at | SLC7A1 | Solute carrier family 7 (cationic amino acid transporter, y+ system), member 1 |
| 357 | 0.004234 | 1525.2 | 1779.3 | 1.17 | 208736_at | ARPC3 | Actin related protein 2/3 complex, subunit 3, 21 kDa |
| 358 | 0.004238 | 82.6 | 123.2 | 1.49 | 229383_at | EST62 | CDNA FLI34016 fis, clone FCBBF2002541 |
| 359 | 0.004265 | 32 | 27.2 | −1.18 | 32137_at | JAG2 | Jagged 2 |
| 360 | 0.004278 | 7.6 | 6.9 | −1.10 | 213249_at | FBXL7 | F-box and leucine-rich repeat protein 7 |
| 361 | 0.004288 | 2770.3 | 3252 | 1.17 | 202803_s_at | ITGB2 | Integrin, beta 2 (complement component 3 receptor 3 and 4 subunit) |
| 362 | 0.004321 | 119 | 159.5 | 1.34 | 203310_at | STXBP3 | Syntaxin binding protein 3 |
| 363 | 0.004335 | 798.5 | 1181 | 1.48 | 202295_s_at | CTSH | Cathepsin H |
| 364 | 0.004354 | 10.4 | 9.1 | −1.14 | 220994_s_at | STXBP6 | Syntaxin binding protein 6 (amisyn) |
| 365 | 0.004355 | 49 | 90.4 | 1.84 | 212224_at | ALDH1A1 | Aldehyde dehydrogenase 1 family, member A1 |
| 366 | 0.004381 | 208.3 | 260.9 | 1.25 | 212120_at | RHOQ | Ras homolog gene family, member Q |
| 367 | 0.004435 | 32.8 | 29.9 | −1.10 | 37586_at | ZNF142 | Zinc finger protein 142 |
| 368 | 0.004453 | 285.1 | 404.8 | 1.42 | 219356_s_at | CHMP5 | Chromatin modifying protein 5 |
| 369 | 0.004458 | 118.6 | 152.6 | 1.29 | 241370_at | LOC286052 | Hypothetical protein LOC286052 |

TABLE A-continued

Differentially expressed consensus genes for mild CAN for both Test
Mild CAN = CAN Banff Class 1; No evidence of CAN = CAN Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 370 | 0.004465 | 13.1 | 11.4 | −1.15 | 1558476_at | C1orf165 | Chromosome 1 open reading frame 165 |
| 371 | 0.004485 | 5.5 | 6.2 | 1.13 | 206533_at | CHRNA5 | Cholinergic receptor, nicotinic, alpha 5 |
| 372 | 0.004489 | 33.2 | 28.8 | −1.15 | 229979_x_at | EST63 | Transcribed locus |
| 373 | 0.004526 | 66.2 | 83.5 | 1.26 | 200764_s_at | CTNNA1 | Catenin (cadherin-associated protein), alpha 1, 102 kDa |
| 374 | 0.004556 | 7.3 | 6.5 | −1.12 | 240874_at | EST64 | Transcribed locus |
| 375 | 0.004558 | 20.4 | 17.2 | −1.19 | 1556672_a_at | RBM6 | RNA binding motif protein 6 |
| 376 | 0.004559 | 13.6 | 10.9 | −1.25 | 236268_at | SEC22C | SEC22 vesicle trafficking protein homolog C (*S. cerevisiae*) |
| 377 | 0.004594 | 68.3 | 57 | −1.20 | 220968_s_at | TSPAN9 | Tetraspanin 9 |
| 378 | 0.004616 | 363.3 | 284.7 | −1.28 | 223042_s_at | FUNDC2 | FUN14 domain containing 2 |
| 379 | 0.004683 | 6.9 | 9.4 | 1.36 | 226311_at | EST65 | CDNA clone IMAGE: 30924414 |
| 380 | 0.004699 | 5 | 4.7 | −1.06 | 1570482_at | EST66 | Pp14356 |
| 381 | 0.00476 | 5.9 | 6.6 | 1.12 | 1562274_at | EST67 | MRNA; cDNA DKFZp 31310929 (from clone DKFZp31310929) |
| 382 | 0.004769 | 40.5 | 32.8 | −1.23 | 201792_at | AEBP1 | AE binding protein 1 |
| 383 | 0.004776 | 11.7 | 13.7 | 1.17 | 229671_s_at | C21orf45 | Chromosome 21 open reading frame 45 |
| 384 | 0.004783 | 23 | 15.8 | −1.46 | 208501_at | GFI1B | Growth factor independent 1B (potential regulator of CDKN1A, translocated in CML) |
| 385 | 0.004788 | 6.6 | 5.9 | −1.12 | 206142_at | ZNF135 | Zing finger protein 135 |
| 386 | 0.004813 | 6.9 | 6.4 | −1.08 | 233594_at | EST68 | CDNA clone IMAGE: 4823221 |
| 387 | 0.004845 | 9 | 8 | −1.13 | 1565407_at | LHX9 | LIM homeobox 9 |
| 388 | 0.004861 | 7.1 | 6.3 | −1.13 | 1559634_at | CHRM3 | Cholinergic receptor, muscarinic 3 |
| 389 | 0.004927 | 23.8 | 36.5 | 1.53 | 236297_at | EST69 | CDNA FLI45742 fis, clone KIDNE2016327 |
| 390 | 0.004932 | 29.6 | 33.1 | 1.12 | 215930_s_at | CTAGE5 | CTAGE family, member 5 |
| 391 | 0.004946 | 101.1 | 128.9 | 1.27 | 209463_s_at | TAF12 | TAF12 RNA polymerase II, TATA box binding protein (TBP)-associated factor, 20 kDa |
| 392 | 0.004975 | 26.4 | 18.6 | −1.42 | 206759_at | FCER2 | Fc fragment of IgE, low affinity II, receptor for (CD23) |
| 393 | 0.004988 | 14.3 | 12.3 | −1.16 | 230950_at | EST70 | Transcribed locus |

TABLE B

Differentially expressed consensus genes for moderate/severe CAN/IFTA for both Test Sets
Moderate/Severe CAN/IFTA = CAN/IFTA Banff Class 2, 3; No evidence of CAN/IFTA = CAN/IFTA Banff Class 0
Probesets with positive fold changes are upregulated in moderate/severe CAN

| | Parametric p-value | Geom mean of intensities in class 1: Banff 0 | Geom mean of intensities in class 2: Banff 2, 3 | Ratio of geom means | Probe Set ID | Gene Symbol | Gene Title |
|---|---|---|---|---|---|---|---|
| 1 | 0.0001775 | 11.1 | 9 | −1.23 | 1566879_at | EST1 | ATP/GTP binding protein-like 1 |
| 2 | 0.0003852 | 4.9 | 4.5 | −1.09 | 241139_at | EST2 | — |
| 3 | 0.0004281 | 5.5 | 6.1 | 1.11 | 231591_at | BHMT | anthrax toxin receptor 2 |
| 4 | 0.0004852 | 20.5 | 26.2 | 1.28 | 242619_x_at | EST3 | — |
| 5 | 0.0005716 | 20.8 | 34.5 | 1.66 | 206674_at | FLT3 | LIM homeobox 9 |
| 6 | 0.0005983 | 5.6 | 4.9 | −1.14 | 204005_s_at | PAWR | — |
| 7 | 0.0006361 | 23 | 39.6 | 1.72 | 220112_at | ANKRD55 | — |
| 8 | 0.0006841 | 6.6 | 5.9 | −1.12 | 239312_at | EST4 | Phospholipase C epsilon |
| 9 | 0.0007962 | 21.4 | 28.1 | 1.31 | 205977_s_at | EPHA1 | — |
| 10 | 0.0008868 | 9.3 | 8.1 | −1.15 | 210412_at | GRIN2B | olfactory receptor, family 8, subfamily G, member 1 |
| 11 | 0.0008881 | 5 | 4.5 | −1.11 | 216089_at | MCFD2L | — |
| 12 | 0.0009531 | 10 | 8.5 | −1.18 | 226211_at | MEG3 | PRKC, apoptosis, WT1, regulator |
| 13 | 0.001086 | 58.7 | 72.7 | 1.24 | 226856_at | MUSTN1 | CUG triplet repeat, RNA binding protein 1 |
| 14 | 0.001156 | 11.7 | 14.7 | 1.26 | 229671_s_at | C21orf45 | PBX/knotted 1 homeobox 1 |
| 15 | 0.001212 | 10 | 11.6 | 1.16 | 219831_at | CDKL3 | cleavage stimulation factor, 3′ pre-RNA, subunit 2, 64 kDa |
| 16 | 0.0013123 | 8.7 | 10 | 1.15 | 233429_at | FLJ23577 | matrix metallopeptidase 1 (interstitial collagenase) |
| 17 | 0.0013489 | 14 | 19 | 1.36 | 210896_s_at | ASPH | IKAROS family zinc finger 1 (Ikaros) |
| 18 | 0.0014846 | 9.7 | 15 | 1.55 | 236901_at | EST5 | EPH receptor A1 |
| 19 | 0.0015437 | 7.7 | 6.8 | −1.13 | 213994_s_at | SPON1 | fms-related tyrosine kinase 3 |
| 20 | 0.0015498 | 11 | 9.5 | −1.16 | 242417_at | LOC283278 | cytochrome P450, family 4, subfamily B, polypeptide 1 |
| 21 | 0.0015652 | 6.3 | 5.6 | −1.13 | 229777_at | CLRN3 | glutamate receptor, ionotropic, N-methyl D-aspartate 2B |
| 22 | 0.0016885 | 311.3 | 218.7 | −1.42 | 205039_s_at | IKZF1 | aspartate beta-hydroxylase |
| 23 | 0.0017597 | 18.8 | 22.5 | 1.20 | 204113_at | CUGBP1 | nuclear factor of kappa light polypeptide gene enhancer in B-cells 2 (p49/p100) |
| 24 | 0.0019344 | 11.6 | 14.8 | 1.28 | 233650_at | CEP63 | met proto-oncogene (hepatocyte growth factor receptor) |
| 25 | 0.0019513 | 42.8 | 57 | 1.33 | 236832_at | LOC221442 | spondin 1, extracellular matrix protein |

TABLE B-continued

Differentially expressed consensus genes for moderate/severe CAN/IFTA for both Test Sets
Moderate/Severe CAN/IFTA = CAN/IFTA Banff Class 2, 3; No evidence of CAN/IFTA = CAN/IFTA Banff Class 0
Probesets with positive fold changes are upregulated in moderate/severe CAN

| | Parametric p-value | Geom mean of intensities in class 1: Banff 0 | Geom mean of intensities in class 2: Banff 2, 3 | Ratio of geom means | Probe Set ID | Gene Symbol | Gene Title |
|---|---|---|---|---|---|---|---|
| 26 | 0.0019757 | 21.9 | 18.6 | −1.18 | 228721_at | C3orf41 | — |
| 27 | 0.0020356 | 6.9 | 8.9 | 1.29 | 226311_at | EST6 | secretogranin III |
| 28 | 0.0020555 | 5.5 | 4.6 | −1.20 | 1566428_at | EST7 | cyclin-dependent kinase-like 3 |
| 29 | 0.0020848 | 18.7 | 15 | −1.25 | 229532_at | ZNF502 | ankyrin repeat domain 55 |
| 30 | 0.0021794 | 10.6 | 12 | 1.13 | 1554615_at | EST8 | heparan-alpha-glucosaminide N-acetyltransferase |
| 31 | 0.0022636 | 5.9 | 5.4 | −1.09 | 230650_at | EST9 | family with sequence similarity 135, member A |
| 32 | 0.0022797 | 76.1 | 62.4 | −1.22 | 204459_at | CSTF2 | maternally expressed 3 (non-protein coding) |
| 33 | 0.0023808 | 5.3 | 4.8 | −1.10 | 1570050_at | EST10 | — |
| 34 | 0.0023855 | 4.7 | 4.3 | −1.09 | 1566096_x_at | EST11 | musculoskeletal, embryonic nuclear protein 1 |
| 35 | 0.0025531 | 9 | 8 | −1.13 | 1565407_at | LHX9 | hexokinase domain containing 1 |
| 36 | 0.0025848 | 5.1 | 5.6 | 1.10 | 232770_at | TUSC3 | — |
| 37 | 0.0026131 | 6.4 | 5.6 | −1.14 | 204475_at | MMP1 | hypothetical protein LOC90784 |
| 38 | 0.0026527 | 11.3 | 14.3 | 1.27 | 243349_at | KIAA1324 | thyroid hormone receptor, beta (erythroblastic leukemia viral (v-erb-a) oncogene homolog 2, avian) |
| 39 | 0.0027257 | 5.7 | 5.1 | 1.12 | 240604_at | EXOD1 | chromosome 3 open reading frame 41 |
| 40 | 0.0027342 | 6 | 5.6 | −1.07 | 210096_at | CYP4B1 | RNA binding protein with multiple splicing 2 |
| 41 | 0.0027896 | 39.3 | 22 | −1.79 | 228390_at | EST12 | hypothetical protein LOC729680 |
| 42 | 0.0027907 | 6.3 | 6.9 | 1.10 | 228977_at | LOC729680 | nuclear receptor subfamily 2, group F, member 2 |
| 43 | 0.0028215 | 9.5 | 10.6 | 1.12 | 213807_x_at | MET | zinc finger protein 502 |
| 44 | 0.0028343 | 7.9 | 6.7 | −1.18 | 228716_at | THRB | CDNA FLJ90800 fis, clone Y79AA1000127 |
| 45 | 0.0029105 | 6.1 | 10.7 | 1.75 | 1560800_at | EST13 | clarin 3 |
| 46 | 0.0031196 | 12.6 | 14.3 | 1.13 | 1567060_at | OR8G1 | — |
| 47 | 0.0033408 | 24.1 | 19.6 | −1.23 | 223497_at | FAM135A | Betaine: homocysteine methyltransferase |
| 48 | 0.0039416 | 5.3 | 5.9 | 1.11 | 211524_at | NFKB2 | tumor suppressor candidate 3 |
| 49 | 0.0039539 | 14.2 | 12.3 | −1.15 | 241261_x_at | EST14 | sperm flagellar 2 |
| 50 | 0.003958 | 12.1 | 10.5 | −1.15 | 243048_at | CECR7 | centrosomal protein 63 kDa |
| 51 | 0.0040206 | 34.8 | 22.1 | 1.57 | 228802_at | RBPMS2 | — |
| 52 | 0.004032 | 4.7 | 4.4 | 1.07 | 219196_at | SCG3 | hypothetical LOC221442 |
| 53 | 0.0041033 | 18.9 | 24.7 | 1.31 | 227614_at | HKDC1 | — |
| 54 | 0.0041799 | 39.2 | 46 | 1.17 | 204195_s_at | PKNOX1 | — |
| 55 | 0.0042431 | 25 | 30.2 | 1.21 | 228515_at | LOC90784 | exoribonuclease 2 |
| 56 | 0.0042468 | 9.7 | 8.7 | −1.11 | 1566739_at | PLCE1 | — |
| 57 | 0.0043315 | 27.7 | 33.5 | 1.21 | 222491_at | HGSNAT | — |
| 58 | 0.0044839 | 7.3 | 8.1 | 1.11 | 1553447_at | AGBL1 | — |
| 59 | 0.0045669 | 6.7 | 6.2 | −1.08 | 229092_at | EST15 | hypothetical protein LOC283278 |
| 60 | 0.0047554 | 9.7 | 11.1 | 1.14 | 233993_at | EST16 | — |
| 61 | 0.004775 | 17.7 | 21 | 1.19 | 242264_at | EST17 | cat eye syndrome chromosome region, candidate 7 |
| 62 | 0.0048752 | 34.1 | 38.1 | 1.12 | 1555536_at | ANTXR2 | KIAA1324 |

TABLE C

Differentially expressed consensus genes for mild CAN/IFTA for both Test Sets
Mild CAN/IFTA = CAN/IFTA Banff Class 1; No evidence of CAN/IFTA = CAN/IFTA Banff Class 0
Probesets with positive fold changes are upregulated in mild CAN

| | Parametric p-value | Geom mean of intensities in class 1: Banff 0 | Geom mean of intensities in class 2: Banff 1 | Fold Change | Probe Set ID | Gene Symbol | Gene Title |
|---|---|---|---|---|---|---|---|
| 1 | 0.000002 | 27.9 | 19.3 | −1.45 | 203796_s_at | BCL7A | B-cell CLL/lymphoma 7A |
| 2 | 2.1E−06 | 11.6 | 16.7 | 1.44 | 233650_at | CEP63 | centrosomal protein 63 kDa |
| 3 | 3.2E−06 | 50.5 | 40.1 | −1.26 | 1552892_at | TNFRSF13C | tumor necrosis factor receptor superfamily, member 13C |
| 4 | 5.9E−06 | 19.2 | 33.6 | 1.75 | 1565597_at | EST1 | *Homo sapiens*, clone IMAGE: 4275461, mRNA |
| 5 | 8.3E−06 | 15.1 | 23.5 | 1.56 | 241752_at | SLC8A1 | solute carrier family 8 (sodium/calcium exchanger), member 1 |
| 6 | 1.25E−05 | 803.7 | 1050.5 | 1.31 | 213702_x_at | ASAH1 | N-acylsphingosine amidohydrolase (acid ceramidase) 1 |
| 7 | 1.61E−05 | 224.8 | 174.8 | −1.29 | 223259_at | ORMDL3 | ORM1-like 3 (*S. cerevisiae*) |
| 8 | 1.84E−05 | 135.4 | 189.9 | 1.40 | 204054_at | PTEN | phosphatase and tensin homolog (mutated in multiple advanced cancers 1) |
| 9 | 1.86E−05 | 26 | 46 | 1.77 | 239012_at | IBRDC2 | IBR domain containing 2 |
| 10 | 2.39E−05 | 1182 | 1724.7 | 1.46 | 200975_at | PPT1 | palmitoyl-protein thioesterase 1 (ceroid-lipofuscinosis, neuronal 1, infantile) |
| 11 | 0.000024 | 174.3 | 363.5 | 2.09 | 206584_at | LY96 | lymphocyte antigen 96 |
| 12 | 3.35E−05 | 9 | 7.6 | −1.18 | 228044_at | C13orf21 | chromosome 13 open reading frame 21 |
| 13 | 4.41E−05 | 250.1 | 327.6 | 1.31 | 225492_at | EST2 | — |

TABLE C-continued

Differentially expressed consensus genes for mild CAN/IFTA for both Test Sets
Mild CAN/IFTA = CAN/IFTA Banff Class 1; No evidence of CAN/IFTA = CAN/IFTA Banff Class 0
Probesets with positive fold changes are upregulated in mild CAN

|    | Parametric p-value | Geom mean of intensities in class 1: Banff 0 | Geom mean of intensities in class 2: Banff 1 | Fold Change | Probe Set ID | Gene Symbol | Gene Title |
|----|---|---|---|---|---|---|---|
| 14 | 4.53E−05 | 7828 | 10660.2 | 1.36 | 202917_s_at | S100A8 | S100 calcium binding protein A8 |
| 15 | 0.000047 | 374.1 | 724.5 | 1.94 | 223501_at | TNFSF13B | tumor necrosis factor (ligand) superfamily, member 13b |
| 16 | 4.75E−05 | 112.7 | 204 | 1.81 | 222496_s_at | FLJ20273 | RNA-binding protein |
| 17 | 5.11E−05 | 22.4 | 38.8 | 1.73 | 224996_at | EST3 | CDNA FLJ39064 fis, clone NT2RP7014583 |
| 18 | 5.13E−05 | 21.6 | 17.5 | −1.23 | 244863_at | EST4 | Transcribed locus |
| 19 | 0.000052 | 7.5 | 9 | 1.20 | 238791_at | ZNF100 | zinc finger protein 100 |
| 20 | 5.66E−05 | 85.2 | 123.8 | 1.45 | 218177_at | CHMP1B | chromatin modifying protein 1B |
| 21 | 5.67E−05 | 203.3 | 336.4 | 1.65 | 226208_at | ZSWIM6 | zinc finger, SWIM-type containing 6 |
| 22 | 7.26E−05 | 180.8 | 237.2 | 1.31 | 203778_at | MANBA | mannosidase, beta A, lysosomal |
| 23 | 0.000089 | 86.6 | 123.4 | 1.42 | 238903_at | LOC137886 | hypothetical protein LOC137886 |
| 24 | 0.000094 | 19.7 | 14.5 | −1.36 | 214308_s_at | HGD | homogentisate 1,2-dioxygenase (homogentisate oxidase) |
| 25 | 0.000103 | 492.9 | 744.6 | 1.51 | 211368_s_at | CASP1 | caspase 1, apoptosis-related cysteine peptidase (interleukin 1, beta, convertase) |
| 26 | 0.000103 | 132.8 | 184.8 | 1.39 | 227017_at | ERICH1 | glutamate-rich 1 |
| 27 | 0.000107 | 10.3 | 15.5 | 1.50 | 228624_at | TMEM144 | transmembrane protein 144 |
| 28 | 0.000108 | 128.7 | 170.2 | 1.32 | 232149_s_at | NSMAF | neutral sphingomyelinase (N-SMase) activation associated factor |
| 29 | 0.000112 | 26.4 | 35.2 | 1.33 | 243287_s_at | OSTM1 | osteopetrosis associated transmembrane protein 1 |
| 30 | 0.000116 | 59.5 | 134.7 | 2.26 | 1552773_at | CLEC4D | C-type lectin domain family 4, member D |
| 31 | 0.000121 | 2887.4 | 3972.4 | 1.38 | 202902_s_at | CTSS | cathepsin S |
| 32 | 0.000125 | 142.4 | 229 | 1.61 | 211744_s_at | CD58 | CD58 molecule |
| 33 | 0.000133 | 35.6 | 26.9 | −1.32 | 243507_s_at | C20orf196 | chromosome 20 open reading frame 196 |
| 34 | 0.000137 | 101.9 | 77.4 | −1.32 | 228832_at | FLJ20021 | hypothetical LOC90024 |
| 35 | 0.000149 | 1057.6 | 1433.5 | 1.36 | 202727_s_at | IFNGR1 | interferon gamma receptor 1 |
| 36 | 0.000169 | 40.5 | 55.5 | 1.37 | 213952_s_at | ALOX5 | Arachidonate 5-lipoxygenase |
| 37 | 0.000174 | 364.6 | 288.1 | −1.27 | 219045_at | RHOF | ras homolog gene family, member F (in filopodia) |
| 38 | 0.000175 | 666 | 974.1 | 1.46 | 212268_at | SERPINB1 | serpin peptidase inhibitor, clade B (ovalbumin), member 1 |
| 39 | 0.00018 | 80.3 | 119.4 | 1.49 | 203276_at | LMNB1 | lamin B1 |
| 40 | 0.00019 | 347.2 | 814.1 | 2.34 | 219666_at | MS4A6A | membrane-spanning 4-domains, subfamily A, member 6A |
| 41 | 0.000204 | 54.9 | 110.9 | 2.02 | 204860_s_at | NAIP///NAIP1B | NLR family, apoptosis inhibitory protein///neuronal apoptosis inhibitory protein (centromeric) |
| 42 | 0.000212 | 3812.4 | 4958.6 | 1.30 | 202388_at | RGS2 | regulator of G-protein signaling 2, 24 kDa |
| 43 | 0.000226 | 24.5 | 43.9 | 1.79 | 1553514_a_at | VNN3 | vanin 3 |
| 44 | 0.000239 | 84.6 | 108.3 | 1.28 | 218364_at | LRRFIP2 | leucine rich repeat (in FLII) interacting protein 2 |
| 45 | 0.000242 | 15.5 | 21.5 | 1.39 | 218888_s_at | NETO2 | neuropilin (NRP) and tolloid (TLL)-like 2 |
| 46 | 0.000258 | 64.6 | 87.8 | 1.36 | 204108_at | NFYA | nuclear transcription factor Y, alpha |
| 47 | 0.000273 | 35.6 | 50.1 | 1.41 | 213935_at | ABHD5 | abhydrolase domain containing 5 |
| 48 | 0.000278 | 54 | 75.5 | 1.40 | 208883_at | UBR5 | ubiquitin protein ligase E3 component n-recognin 5 |
| 49 | 0.000282 | 334.9 | 425 | 1.27 | 222148_s_at | RHOT1 | ras homolog gene family, member T1 |
| 50 | 0.000284 | 564.8 | 712.6 | 1.26 | 227266_s_at | FYB | FYN binding protein (FYB-120/130) |

TABLE D

Top 50 Differentially expressed consensus genes for moderate/severe CAN/IFTA for both Test Sets
Moderate/Severe CAN/IFTA = CAN/IFTA Banff Class 2, 3; No evidence of CAN/IFTA = CAN/IFTA Banff Class 0

|    | Parametric p-value | Geom mean of intensities in class 1: Banff 0 | Geom mean of intensities in class 2: Banff 2, 3 | Ratio of geom means | Probe Set ID | Gene Symbol | Gene Title |
|----|---|---|---|---|---|---|---|
| 1  | 0.000178 | 11.1 | 9 | −1.23 | 1566879_at | EST1 | ATP/GTP binding protein-like 1 |
| 2  | 0.000385 | 4.9 | 4.5 | −1.09 | 241139_at | EST2 | — |
| 3  | 0.000428 | 5.5 | 6.1 | 1.11 | 231591_at | BHMT | anthrax toxin receptor 2 |
| 4  | 0.000485 | 20.5 | 26.2 | 1.28 | 242619_x_at | EST3 | — |
| 5  | 0.000572 | 20.8 | 34.5 | 1.66 | 206674_at | FLT3 | LIM homeobox 9 |
| 6  | 0.000598 | 5.6 | 4.9 | −1.14 | 204005_s_at | PAWR | — |
| 7  | 0.000636 | 23 | 39.6 | 1.72 | 220112_at | ANKRD55 | — |
| 8  | 0.000684 | 6.6 | 5.9 | −1.12 | 239312_at | EST4 | Phospholipase C epsilon |
| 9  | 0.000796 | 21.4 | 28.1 | 1.31 | 205977_s_at | EPHA1 | — |
| 10 | 0.000887 | 9.3 | 8.1 | −1.15 | 210412_at | GRIN2B | olfactory receptor, family 8, subfamily G, member 1 |
| 11 | 0.000888 | 5 | 4.5 | −1.11 | 216089_at | MCFD2L | — |
| 12 | 0.000953 | 10 | 8.5 | −1.18 | 226211_at | MEG3 | PRKC, apoptosis, WT1, regulator |
| 13 | 0.001086 | 58.7 | 72.7 | 1.24 | 226856_at | MUSTN1 | CUG triplet repeat, RNA binding protein 1 |
| 14 | 0.001156 | 11.7 | 14.7 | 1.26 | 229671_s_at | C21orf45 | PBX/knotted 1 homeobox 1 |
| 15 | 0.001212 | 10 | 11.6 | 1.16 | 219831_at | CDKL3 | cleavage stimulation factor, 3' pre-RNA, subunit 2, 64 kDa |

TABLE D-continued

Top 50 Differentially expressed consensus genes for moderate/severe CAN/IFTA for both Test Sets
Moderate/Severe CAN/IFTA = CAN/IFTA Banff Class 2, 3; No evidence of CAN/IFTA = CAN/IFTA Banff Class 0

| | Parametric p-value | Geom mean of intensities in class 1: Banff 0 | Geom mean of intensities in class 2: Banff 2, 3 | Ratio of geom means | Probe Set ID | Gene Symbol | Gene Title |
|---|---|---|---|---|---|---|---|
| 16 | 0.001312 | 8.7 | 10 | 1.15 | 233429_at | FLJ23577 | matrix metallopeptidase 1 (interstitial collagenase) |
| 17 | 0.001349 | 14 | 19 | 1.36 | 210896_s_at | ASPH | IKAROS family zinc finger 1 (Ikaros) |
| 18 | 0.001485 | 9.7 | 15 | 1.55 | 236901_at | EST5 | EPH receptor A1 |
| 19 | 0.001544 | 7.7 | 6.8 | −1.13 | 213994_s_at | SPON1 | fms-related tyrosine kinase 3 |
| 20 | 0.00155 | 11 | 9.5 | −1.16 | 242417_at | LOC283278 | cytochrome P450, family 4, subfamily B, polypeptide 1 |
| 21 | 0.001565 | 6.3 | 5.6 | −1.13 | 229777_at | CLRN3 | glutamate receptor, ionotropic, N-methyl D-aspartate 2B |
| 22 | 0.001689 | 311.3 | 218.7 | −1.42 | 205039_s_at | IKZF1 | aspartate beta-hydroxylase |
| 23 | 0.00176 | 18.8 | 22.5 | 1.20 | 204113_at | CUGBP1 | nuclear factor of kappa light polypeptide gene enhancer in B-cells 2 (p49/p100) |
| 24 | 0.001934 | 11.6 | 14.8 | 1.28 | 233650_at | CEP63 | met proto-oncogene (hepatocyte growth factor receptor) |
| 25 | 0.001951 | 42.8 | 57 | 1.33 | 236832_at | LOC221442 | spondin 1, extracellular matrix protein |
| 26 | 0.001976 | 21.9 | 18.6 | −1.18 | 228721_at | C3orf41 | — |
| 27 | 0.002036 | 6.9 | 8.9 | 1.29 | 226311_at | EST6 | secretogranin III |
| 28 | 0.002056 | 5.5 | 4.6 | −1.20 | 1566428_at | EST7 | cyclin-dependent kinase-like 3 |
| 29 | 0.002085 | 18.7 | 15 | −1.25 | 229532_at | ZNF502 | ankyrin repeat domain 55 |
| 30 | 0.002179 | 10.6 | 12 | 1.13 | 1554615_at | EST8 | heparan-alpha-glucosaminide N-acetyltransferase |
| 31 | 0.002264 | 5.9 | 5.4 | −1.09 | 230650_at | EST9 | family with sequence similarity 135, member A |
| 32 | 0.00228 | 76.1 | 62.4 | −1.22 | 204459_at | CSTF2 | maternally expressed 3 (non-protein coding) |
| 33 | 0.002381 | 5.3 | 4.8 | −1.10 | 1570050_at | EST10 | — |
| 34 | 0.002386 | 4.7 | 4.3 | −1.09 | 1566096_x_at | EST11 | musculoskeletal, embryonic nuclear protein 1 |
| 35 | 0.002553 | 9 | 8 | −1.13 | 1565407_at | LHX9 | hexokinase domain containing 1 |
| 36 | 0.002585 | 5.1 | 5.6 | 1.10 | 232770_at | TUSC3 | — |
| 37 | 0.002613 | 6.4 | 5.6 | −1.14 | 204475_at | MMP1 | hypothetical protein LOC90784 |
| 38 | 0.002653 | 11.3 | 14.3 | 1.27 | 243349_at | KIAA1324 | thyroid hormone receptor, beta (erythroblastic leukemia viral (v-erb-a) oncogene homolog 2, avian) |
| 39 | 0.002726 | 5.7 | 5.1 | −1.12 | 240604_at | EXOD1 | chromosome 3 open reading frame 41 |
| 40 | 0.002734 | 6 | 5.6 | −1.07 | 210096_at | CYP4B1 | RNA binding protein with multiple splicing 2 |
| 41 | 0.00279 | 39.3 | 22 | −1.79 | 228390_at | EST12 | hypothetical protein LOC729680 |
| 42 | 0.002791 | 6.3 | 6.9 | 1.10 | 228977_at | LOC729680 | nuclear receptor subfamily 2, group F, member 2 |
| 43 | 0.002822 | 9.5 | 10.6 | 1.12 | 213807_x_at | MET | zinc finger protein 502 |
| 44 | 0.002834 | 7.9 | 6.7 | −1.18 | 228716_at | THRB | CDNA FLJ90800 fis, clone Y79AA1000127 |
| 45 | 0.002911 | 6.1 | 10.7 | 1.75 | 1560800_at | EST13 | clarin 3 |
| 46 | 0.00312 | 12.6 | 14.3 | 1.13 | 1567060_at | OR8G1 | — |
| 47 | 0.003341 | 24.1 | 19.6 | −1.23 | 223497_at | FAM135A | Betaine: homocysteine methyltransferase |
| 48 | 0.003942 | 5.3 | 5.9 | 1.11 | 211524_at | NFKB2 | tumor suppressor candidate 3 |
| 49 | 0.003954 | 14.2 | 12.3 | −1.15 | 241261_x_at | EST14 | sperm flagellar 2 |
| 50 | 0.003958 | 12.1 | 10.5 | −1.15 | 243048_at | CECR7 | centrosomal protein 63 kDa |

TABLE E

| | International Protein Index/UniGene | Symbol | Entrez Gene Name |
|---|---|---|---|
| 1 | Hs.103854 | DOK1 | docking protein 1, 62 kDa (downstream of tyrosine kinase 1) |
| 2 | Hs.109752 | C6ORF108 | chromosome 6 open reading frame 108 |
| 3 | Hs.110675 | APOC1 | apolipoprotein C-I |
| 4 | Hs.116459 | MAN2A2 | mannosidase, alpha, class 2A, member 2 |
| 5 | Hs.117331 | TREML1 | triggering receptor expressed on myeloid cells-like 1 |
| 6 | Hs.119177 | ARF3 | ADP-ribosylation factor 3 |
| 7 | Hs.123198 | MYO9B | myosin IXB |
| 8 | Hs.134084 | M6PR | mannose-6-phosphate receptor (cation dependent) |
| 9 | Hs.151135 | FN3K | fructosamine 3 kinase |
| 10 | Hs.159509 | SERPINF2 | serpin peptidase inhibitor, clade F (alpha-2 antiplasmin, pigment epithelium derived factor), member 2 |
| 11 | Hs.190334 | RAP1A | RAP1A, member of RAS oncogene family |
| 12 | Hs.191215 | CYTH1 | cytohesin 1 |
| 13 | Hs.202 | TSPO | translocator protein (18 kDa) |
| 14 | Hs.203637 | PLS1 | plastin 1 (I isoform) |
| 15 | Hs.226007 | RDH11 | retinol dehydrogenase 11 (all-trans/9-cis/11-cis) |
| 16 | Hs.24178 | EML2 | echinoderm microtubule associated protein like 2 |
| 17 | Hs.24258 | GUCY1A3 | guanylate cyclase 1, soluble, alpha 3 |
| 18 | Hs.24889 | FMN2 | formin 2 |
| 19 | Hs.260750 | SNX12 | sorting nexin 12 |
| 20 | Hs.277624 | ZZEF1 | zinc finger, ZZ-type with EF-hand domain 1 |
| 21 | Hs.287714 | RAB32 | RAB32, member RAS oncogene family |
| 22 | Hs.301412 | UFC1 | ubiquitin-fold modifier conjugating enzyme 1 |
| 23 | Hs.306327 | RAB3GAP1 | RAB3 GTPase activating protein subunit 1 (catalytic) |

TABLE E-continued

| | International Protein Index/UniGene | Symbol | Entrez Gene Name |
|---|---|---|---|
| 24 | Hs.327527 | SMARCA4 | SWI/SNF related, matrix associated, actin dependent regulator of chromatin, subfamily a, member 4 |
| 25 | Hs.363396 | CFH | complement, factor H |
| 26 | Hs.368078 | DNAJA2 | DnaJ (Hsp40) homolog, subfamily A, member 2 |
| 27 | Hs.368527 | TOLLIP | toll interacting protein |
| 28 | Hs.368626 | RTN1 | reticulon 1 |
| 29 | Hs.369840 | NID2 | nidogen 2 (osteonidogen) |
| 30 | Hs.376933 | GUK1 | guanylate kinase 1 |
| 31 | Hs.38449 | SERPINE2 | serpin peptidase inhibitor, clade E (nexin, plasminogen activator inhibitor type 1), member 2 |
| 32 | Hs.390567 | FYN | FYN oncogene related to SRC, FGR, YES |
| 33 | Hs.390657 | GSTK1 | glutathione S-transferase kappa 1 |
| 34 | Hs.411312 | ITGA2B (includes EG: 3674) | integrity alpha 2b (platelet glycoprotein IIb of IIb/IIIa complex, antigen CD41) |
| 35 | Hs.414795 | SERPINE1 | serpin peptidase inhibitor, clade E (nexin, plasminogen activator inhibitor type 1), member 1 |
| 36 | Hs.416848 | CTSW | cathepsin W |
| 37 | Hs.420529 | UBE2V1 | ubiquitin-conjugating enzyme E2 variant 1 |
| 38 | Hs.429608 | REEP5 | receptor accessory protein 5 |
| 39 | Hs.433068 | PRKAR2B | protein kinase, cAMP-dependent, regulatory, type II, beta |
| 40 | Hs.435291 | ARHGAP6 | Rho GTPase activating protein 6 |
| 41 | Hs.435512 | PPP3CA | protein phosphatase 3 (formerly 2B), catalytic subunit, alpha isoform |
| 42 | Hs.438906 | C22ORF30 | chromosome 22 open reading frame 30 |
| 43 | Hs.443976 | CEP250 | centrosomal protein 250 kDa |
| 44 | Hs.458917 | SCAMP2 | secretory carrier membrane protein 2 |
| 45 | Hs.460109 | MYH11 | myosin, heavy chain 11, smooth muscle |
| 46 | Hs.462379 | TOM1L2 | target of myb1-like 2 (chicken) |
| 47 | Hs.464813 | PSMA8 | proteasome (prosome, macropain) subunit, alpha type, 8 |
| 48 | Hs.465295 | LMAN1 | lectin, mannose-binding, 1 |
| 49 | Hs.466910 | CDA | cytidine deaminase |
| 50 | Hs.477009 | USP24 | ubiquitin specific peptidase 24 |
| 51 | Hs.477352 | PDIA5 | protein disulfide isomerase family A, member 5 |
| 52 | Hs.4779 | GATAD2B | GATA zinc finger domain containing 2B |
| 53 | Hs.480364 | METAP1 | methionyl aminopeptidase 1 |
| 54 | Hs.481836 | MTMR12 | myotubularin related protein 12 |
| 55 | Hs.481860 | TARS | threonyl-tRNA synthetase |
| 56 | Hs.482873 | TMED5 | transmembrane emp24 protein transport domain containing 5 |
| 57 | Hs.487540 | RPA3 | replication protein A3, 14 kDa |
| 58 | Hs.49582 | PPP1R12A | protein phosphatase 1, regulatory (inhibitor) subunit 12A |
| 59 | Hs.501200 | RGS10 | regulator of G-protein signaling 10 |
| 60 | Hs.502244 | EIF3M | eukaryotic translation initiation factor 3, subunit M |
| 61 | Hs.50382 | TJP2 | tight junction protein 2 (zona occludens 2) |
| 62 | Hs.506603 | APPL2 | adaptor protein, phosphotyrosine interaction, PH domain and leucine zipper containing 2 |
| 63 | Hs.513055 | WDR61 | WD repeat domain 61 |
| 64 | Hs.513646 | IVD | isovaleryl Coenzyme A dehydrogenase |
| 65 | Hs.514012 | MAP2K3 | mitogen-activated protein kinase kinase 3 |
| 66 | Hs.514199 | VAT1 | vesicle amine transport protein 1 homolog (*T. californica*) |
| 67 | Hs.514870 | ATP5F1 | ATP synthase, H+ transporting, mitochondrial F0 complex, subunit B1 |
| 68 | Hs.520048 | HLA-DRA | major histocompatibility complex, class II, DR alpha |
| 69 | Hs.524518 | STAT6 | signal transducer and activator of transcription 6, interleukin-4 induced |
| 70 | Hs.525419 | LIMA1 | LIM domain and actin binding 1 |
| 71 | Hs.528952 | TRIM25 | tripartite motif-containing 25 |
| 72 | Hs.529023 | ZNF532 | zinc finger protein 532 |
| 73 | Hs.530096 | EIF3I (includes EG: 8668) | eukaryotic translation initiation factor 3, subunit I |
| 74 | Hs.573495 | SLC44A1 | solute carrier family 44, member 1 |
| 75 | Hs.578450 | MESDC2 | mesoderm development candidate 2 |
| 76 | Hs.584790 | PPP2R1B | protein phosphatase 2 (formerly 2A), regulatory subunit A, beta isoform |
| 77 | Hs.592771 | DGKG | diacylglycerol kinase, gamma 90 kDa |
| 78 | Hs.620557 | ANK2 | ankyrin 2, neuronal |
| 79 | Hs.631569 | PPP1R14A | protein phosphatase 1, regulatory (inhibitor) subunit 14A |
| 80 | Hs.63348 | EMILIN1 | elastin microfibril interfacer 1 |
| 80 | Hs.63348 | EMILIN1 | elastin microfibril interfacer 1 |
| 81 | Hs.64016 | PRO51 | protein S (alpha) |
| 82 | Hs.647018 | CLIP2 | CAP-GLY domain containing linker protein 2 |
| 83 | Hs.647064 | RARRES2 | retinoic acid receptor responder (tazarotene induced) 2 |
| 84 | Hs.653263 | CEP110 | centrosomal protein 110 kDa |
| 85 | Hs.654494 | HLA-C | major histocompatibility complex, class I, C |
| 86 | Hs.654439 | APOE | apolipoprotein E |
| 87 | Hs.654473 | MAOB | monoamine oxidase B |
| 88 | Hs.654581 | PRPS2 | phosphoribosyl pyrophosphate synthetase 2 |
| 89 | Hs.654634 | COC42BPB | CDC42 binding protein kinase beta (DMPK-like) |
| 90 | Hs.655207 | F2 | coagulation factor II (thrombin) |
| 91 | Hs.655361 | HPR (includes EG: 3250) | haptoglobin-related protein |
| 92 | Hs.656274 | TNFAIP8 | tumor necrosis factor, alpha-induced protein 8 |
| 93 | Hs.656726 | STRN | striatin, calmodulin binding protein |
| 94 | Hs.658434 | PSIP1 | PC4 and SFRS1 interacting protein 1 |
| 95 | Hs.660130 | CD226 | CD226 molecule |
| 96 | Hs.695926 | RASA1 | RAS p21 protein activator (GTPase activating protein) 1 |
| 97 | Hs.696074 | DHX15 | DEAH (Asp-Glu-Ala-His) box polypeptide 15 |

TABLE E-continued

| | International Protein Index/UniGene | Symbol | Entrez Gene Name |
|---|---|---|---|
| 98 | Hs.696325 | ANO6 | anoctamin 6 |
| 99 | Hs.699154 | LYN | v-yes-1 Yamaguchi sarcoma viral related oncogene homolog |
| 100 | Hs.7486 | ETHE1 | ethylmalonic encephalopathy 1 |
| 101 | Hs.7753 | CALU | calumenin |
| 102 | Hs.77741 | KNG1 (includes EG: 3827) | kininogen 1 |
| 103 | Hs.79322 | QARS | glutaminyl-tRNA synthetase |
| 104 | Hs.8004 | KALRN | kalirin, RhoGEF kinase |
| 105 | Hs.81934 | ACADSB | acyl-Coenzyme A dehydrogenase, short/branched chain |
| 106 | Hs.90061 | PGRMC1 | progesterone receptor membrane component 1 |
| 107 | Hs.904 | AGL | amylo-1,6-glucosidase,4-alpha-glucanotransferase |
| 108 | IPI00010951 | EPPK1 | epiplakin 1 |
| 109 | IPI00011891 | PRKAA1 | protein kinase, AMP-activated, alpha 1 catalytic subunit |
| 110 | IPI00165421 | SERPINC1 | serpin peptidase inhibitor, clade C (antithrombin), member 1 |
| 111 | IPI00301271 | RPN2 | ribophorin II |
| 112 | IPI00382606 | F7 | coagulation factor VII (serum prothrombin conversion accelerator) |
| 113 | IPI00448925 | IGHG1 | immunoglobulin heavy constant gamma 1 (G1m marker) |
| 114 | IPI00783829 | IPO5 | importin 5 |
| 115 | IPI00787190 | HLA-B | major histocompatibility complex, class I, B |
| 116 | IPI00788786 | VWF | von Willebrand factor |
| 117 | IPI00797856 | HPSE | heparanase |

TABLE F

| | International Protein Index/UniGene | Symbol | Entrez Gene Name |
|---|---|---|---|
| 1 | IPI00001753 | MYH4 | myosin, heavy chain 4, skeletal muscle |
| 2 | Hs.110837 | TUBB4 | tubulin, beta 4 |
| 3 | Hs.132499 | ARPC5L (includes EG: 81873) | actin related protein 2/3 complex, subunit 5-like |
| 4 | Hs.133892 | TPM1 | tropomyosin 1 (alpha) |
| 5 | Hs.143046 | CORO6 | coronin 6 |
| 6 | Hs.1437 | GAA | glucosidase, alpha; acid |
| 7 | Hs.143703 | EHD4 | EH-domain containing 4 |
| 8 | Hs.147433 | PCNA | proliferating cell nuclear antigen |
| 9 | Hs.148641 | CTSH | cathepsin H |
| 10 | Hs.154078 | LBP | lipopolysaccharide binding protein |
| 11 | Hs.156367 | RPS29 | ribosomal protein S29 |
| 12 | Hs.158339 | SLRPINB10 | serpin peptidase inhibitor, clade B (ovalbumin), member 10 |
| 13 | Hs.161357 | PDHB (includes EG: 5162) | pyruvate dehydrogenase (lipoamide) beta |
| 14 | Hs.16355 | MYH10 | myosin, heavy chain 10, non-muscle |
| 15 | Hs.163867 | CD14 | CD14 molecule |
| 16 | Hs.164144 | EIF5A2 | eukaryotic translation initiation factor 5A2 |
| 17 | Hs.169284 | PRPS1L1 | phosphoribosyl pyrophosphate synthetase 1-like 1 |
| 18 | Hs.169900 | PABPC4 | poly(A) binding protein, cytoplasmic 4 (inducible form) |
| 19 | H5.170310 | CECR1 | cat eye syndrome chromosome region, candidate 1 |
| 20 | Hs.171626 | SKP1 | S-phase kinase-associated protein 1 |
| 21 | Hs.173043 | MTA2 | metastasis associated 1 family, member 2 |
| 22 | Hs.188401 | ANXA10 | annexin A10 |
| 23 | Hs.189409 | FNBP1 | formin binding protein 1 |
| 24 | Hs.196437 | MOBKL1B | MOB1, Mps One Binder kinase activator-like 1B (yeast) |
| 25 | Hs.200333 | APOB48R | apolipoprotein B48 receptor |
| 26 | Hs.213470 | PSMB7 | proteasome (prosome, macropain) subunit, beta type, 7 |
| 27 | Hs.220594 | CCDC58 | coiled-coil domain containing 58 |
| 28 | Hs.224171 | ENO3 | enolase 3 (beta, muscle) |
| 29 | Hs.236030 | SMARCC2 (includes EG: 6601) | SWI/SNF related, matrix associated, actin dependent regulator of chromatin, subfamily c, member 2 |
| 30 | Hs.248746 | AGXT2L2 | alanine-glyoxylate aminotransferase 2-like 2 |
| 31 | Hs.252549 | CTSZ (includes EG: 1522) | cathepsin Z |
| 32 | Hs.258314 | BRE | brain and reproductive organ-expressed (TNFRSF1A modulator) |
| 33 | Hs.263812 | NUDC | nuclear distribution gene C homolog (*A. nidulans*) |
| 34 | Hs.258963 | UBAP1 | ubiquitin associated protein 1 |
| 36 | Hs.279640 | TPR | translocated promoter region (to activated MET oncogene) |
| 36 | Hs.282901 | RBM39 | RNA binding motif protein 39 |
| 37 | Hs.284491 | PDXK | pyridoxal (pyridoxine, vitamin B6) kinase |
| 38 | Hs.309090 | SFRS7 | splicing factor, arginine/serine-rich 7, 35 kDa |
| 39 | Hs.3100 | KARS | lysyl-tRNA synthetase |
| 40 | Hs.31053 | TBCB | tubulin folding cofactor B |
| 41 | Hs.319334 | NASP | nuclear autoantigenic sperm protein (histone-binding) |
| 42 | Hs.325978 | NUMA1 | nuclear mitotic apparatus protein 1 |
| 43 | Hs.335034 | DPYD | dihydropyrimidine dehydrogenase |
| 44 | Hs.337766 | RPL18A | ribosomal protein L18a |
| 45 | Hs.3439 | STOML2 | stomatin (EPB72)-like 2 |

TABLE F-continued

| | International Protein Index/UniGene | Symbol | Entrez Gene Name |
|---|---|---|---|
| 46 | Hs.356604 | WNK1 | WNK lysine deficient protein kinase 1 |
| 47 | Hs.368077 | SERPINB8 | serpin peptidase inhibitor, clade B (ovalbumin), member 8 |
| 48 | Hs.368203 | DOCK11 | dedicator of cytokinesis 11 |
| 49 | Hs.368266 | CLTCL1 | clathrin, heavy chain-like 1 |
| 50 | Hs.36927 | HSPH1 | heat shock 105 kDa/110 kDa protein 1 |
| 51 | Hs.369373 | SEC23B | Sec23 homolog B (S. cerevisiae) |
| 52 | Hs.375957 | ITGB2 | integrin, beta 2 (complement component 3 receptor 3 and 4 subunit) |
| 53 | Hs.376933 | GUK1 | guanylate kinase 1 |
| 54 | Hs.388664 | RPL11 | ribosomal protein L11 |
| 55 | Hs.403436 | DCI | dodecenoyl-Coenzyme A delta isomerase (3,2 trans-enoyl-Coenzyme A isomerase) |
| 56 | Hs.406423 | SF3B2 | splicing factor 3b, subunit 2, 145 kDa |
| 57 | Hs.407190 | FKBP5 | FK506 binding protein 5 |
| 58 | Hs.408061 | FABP5 | fatty acid binding protein 5 (psoriasis-associated) |
| 59 | Hs.408236 | TXNDC17 | thioredoxin domain containing 17 |
| 60 | Hs.409834 | PHPT1 | phosphohistidine phosphatase 1 |
| 61 | Hs.412117 | ANXA6 | annexin A6 |
| 62 | Hs.429180 | EIF2S2 | eukaryotic translation initiation factor 2, subunit 2 beta, 38 kDa |
| 63 | Hs.432674 | LARS | leucyl-tRNA synthetase |
| 64 | Hs.433222 | NPC2 | Niemann-Pick disease, type C2 |
| 65 | Hs.434996 | GIT2 | G protein-coupled receptor kinase interacting ArfGAP 2 |
| 66 | Hs.437385 | NECAP2 | NECAP endocytosis associated 2 |
| 67 | Hs.440895 | MYH3 | myosin, heavy chain 3, skeletal muscle, embryonic |
| 68 | Hs.440932 | 9-Sep | septin 9 |
| 69 | Hs.460002 | FLJ11151 | hypothetical protein FLJ11151 |
| 70 | Hs.461925 | RPA1 | replication protein A1, 70 kDa |
| 71 | Hs.465224 | NARS | asparaginyl-tRNA synthetase |
| 72 | Hs.465761 | ARHGEF18 | rho/rac guanine nucleotide exchange factor (GEF) 18 |
| 73 | Hs.465924 | SHBS (includes EG: 6390) | succinate dehydrogenase complex, subunit B, iron sulfur (Ip) |
| 74 | Hs.470627 | LCK | lymphocyte-specific protein tyrosine kinase |
| 75 | Hs.471207 | NDUFS1 | NADH dehydrogenase (ubiquinone) Fe—S protein 1, 75 kDa (NADH-coenzyme Q reductase) |
| 76 | Hs.477126 | ATG3 | ATG3 autophagy related 3 homolog (S. cerevisiae) |
| 77 | Hs.484412 | EXOC2 | exocyst complex component 2 |
| 78 | Hs.491440 | PPP2CB | protein phosphatase 2 (formerly 2A), catalytic subunit, beta isoform |
| 79 | Hs.494496 | FBP1 | fructose-1,6-bisphosphatase 1 |
| 80 | Hs.494595 | TMOD1 | tropomodulin 1 |
| 81 | Hs.497599 | WARS | tryptophanyl-tRNA synthetase |
| 82 | Hs.502328 | CD44 | CD44 molecule (Indian blood group) |
| 83 | Hs.502756 | AHNAK | AHNAK nucleoprotein |
| 84 | Hs.505033 | KRAS | v-Ki-ras2 Kirsten rat sarcoma viral oncogene homolog |
| 85 | Hs.5086 | RBM42 | RNA binding motif protein 42 |
| 86 | Hs.508738 | ARHGEF7 | Rho guanine nucleotide exchange factor (GEF) 7 |
| 87 | Hs.509736 | HSP90AB1 | heat shock protein 90 kDa alpha (cytosolic), class B member 1 |
| 88 | Hs 513726 | GBP5 | guanylate binding protein 5 |
| 89 | Hs.514495 | SRP68 | signal recognition particle 68 kDa |
| 90 | Hs.514581 | ACTG1 | actin, gamma 1 |
| 91 | Hs.517307 | MX1 | myxovirus (influenza virus) resistance 1, interferon-inducible protein p78 (mouse) |
| 92 | Hs.517949 | MAP4 | microtubule-associated protein 4 |
| 93 | Hs.518198 | CSTA (includes EG: 1475) | cystatin A (stefin A) |
| 94 | Hs.518662 | FAM129A | family with sequence similarity 129, member A |
| 95 | Hs.521924 | PUF60 | poly-U binding splicing factor 60 KDa |
| 96 | Hs.529989 | RNASET2 | ribonuclease T2 |
| 97 | Hs.531176 | SARS | seryl-tRNA synthetase |
| 98 | Hs.531807 | ARHGAP25 | Rho GTPase activating protein 25 |
| 99 | Hs.534350 | SMARCB1 | SWI/SNF related, matrix associated, actin dependent regulator of chromatin, subfamily b, member 1 |
| 100 | Hs.534770 | PKM2 | pyruvate kinase, muscle |
| 101 | Hs.535581 | TPM3 | tropomyosin 3 |
| 102 | Hs.55682 | EIF3D | eukaryotic translation initiation factor 3, subunit D |
| 103 | Hs.583855 | SNX6 | sorting nexin 6 |
| 104 | Hs.587558 | NCF2 | neutrophil cytosolic factor 2 |
| 105 | Hs.591176 | DYNLL2 | dynein, light chain, LC8-type 2 |
| 106 | Hs.591768 | BTF3 | basic transcription factor 3 |
| 107 | Hs.591922 | SLK | STE20-like kinase (yeast) |
| 108 | Hs.632733 | ALDH2 | aldehyde dehydrogenase 2 family (mitochondrial) |
| 109 | Hs.643487 | ACAA1 | acetyl-Coenzyme A acyltransferase 1 |
| 110 | Hs.649475 | RPL24 | ribosomal protein L24 |
| 111 | Hs.654404 | HLA-C | major histocompatibility complex, class I, C |
| 112 | Hs.654408 | NFKB1 | nuclear factor of kappa light polypeptide gene enhancer in B-cells 1 |
| 113 | Hs.654429 | SEC24C (includes EG: 9632) | SEC24 family, member C (S. cerevisiae) |
| 114 | Hs.654521 | WIPF1 | WAS/WASL interacting protein family, member 1 |
| 115 | Hs.654543 | TUBB2A | tubulin, beta 2A |
| 116 | Hs.654597 | ACAP2 | ArfGAP with coiled-coil, ankyrin repeat and PH domains 2 |
| 117 | Hs.655196 | HP | haptoglobin |
| 118 | Hs.656726 | STRN | striatin, calmodulin binding protein |
| 119 | Hs.656870 | SLC25A24 | solute carrier family 25 (mitochondrial carrier; phosphate carrier), member 24 |
| 120 | Hs.687055 | PARP14 | poly (ADP-ribose) polymerase family, member 14 |

TABLE F-continued

| | International Protein Index/UniGene | Symbol | Entrez Gene Name |
|---|---|---|---|
| 121 | Hs.68714 | SFRS1 | splicing factor, arginine/serine-rich 1 |
| 122 | Hs.690634 | HSPA1L | heat shock 70 kDa protein 1-like |
| 123 | Hs.69293 | HEXB | hexosaminidase B (beta polypeptide) |
| 124 | Hs.695973 | HNRNPK | heterogeneous nuclear ribonucleoprotein K |
| 125 | Hs.699408 | CLINT1 | clathrin interactor 1 |
| 126 | Hs.699441 | NFATC2 | nuclear factor of activated T-cells, cytoplasmic, calcineurin-dependent 2 |
| 127 | Hs.73839 | RNASE3 | ribonuclease, RNase A family, 3 (eosinophil cationic protein) |
| 128 | Hs.74368 | CKAP4 | cytoskeleton-associated protein 4 |
| 129 | Hs.77254 | CBX1 | chromobox homolog 1 (HP1 beta homolog Drosophila) |
| 130 | Hs.77897 | SF3A3 | splicing factor 3a, subunit 3, 60 kDa |
| 131 | Hs.78880 | ILVBL | ilvB (bacterial acetolactate synthase)-like |
| 132 | Hs.79110 | NCL | nucleolin |
| 133 | Hs.8360 | C11ORF54 | chromosome 11 open reading frame 54 |
| 134 | Hs.83753 | SNRPB | small nuclear ribonucleoprotein polypeptides B and B1 |
| 135 | Hs.861 | MARK3 | mitogen-activated protein kinase 3 |
| 136 | Hs.99936 | KRT10 | keratin 10 |
| 137 | IPI00074489 | NDUFB10 | NADH dehydrogenase (ubiquinone) 1 beta subcomplex, 10, 22 kDa |
| 138 | IPI00384938 | IGHG1 | immunoglobulin heavy constant gamma 1 (G1m marker) |
| 139 | IPI00396421 | KIAA0776 | KIAA0776 |
| 140 | IPI00401105 | RPS25 | ribosomal protein S25 |
| 141 | IPI00413108 | RPSA (includes EG: 3921) | ribosomal protein SA |
| 142 | IPI00456853 | FAM21C | family with sequence similarity 21, member C |
| 143 | IPI00465022 | SMCHD1 | structural maintenance of chromosomes flexible hinge domain containing 1 |

TABLE G

| | International Protein Index/UniGene | Symbol | Entrez Gene Name | Fold Change (positive numbers are upregulated in B1) |
|---|---|---|---|---|
| 1 | Hs.180062 | PSMB8 | proteasome (prosome, macropain) subunit, beta type, 8 (large multifunctional peptidase 7) | 1.74748 |
| 2 | IPI00001539 | ACAA2 | acetyl-Coenzyme A acyltransferase 2 | 2.53112 |
| 3 | Hs.412117 | ANXA6 | annexin A6 | 1.99146 |
| 4 | Hs.90093 | HSPA4 | heat shock 70 kDa protein 4 | 2.72271 |
| 5 | Hs.130316 | DBN1 | drebrin 1 | -2.19867 |
| 6 | IPI00003438 | DNAJC8 | DnaJ (Hsp40) homolog, subfamily C, member 8 | 2.74556 |
| 7 | Hs.186350 | RPL4 | ribosomal protein L4 | 1.80696 |
| 8 | Hs.175437 | EPB41 | erythrocyte membrane protein band 4.1 (elliptocytosis 1, RH-linked) | 1.37195 |
| 9 | Hs.2178 | HIST2H2BE | histone cluster 2, H2be | 1.73893 |
| 10 | Hs.524630 | UBE2N | ubiquitin-conjugating enzyme E2N (UBC13 homolog, yeast) | 2.17574 |
| 11 | Hs.411695 | HK3 | hexokinase 3 (white cell) | 2.79458 |
| 12 | Hs.489284 | ARPC1B | actin related protein 2/3 complex, subunit 1B, 41 kDa | 1.87474 |
| 13 | Hs.514934 | CAPZA1 | capping protein (actin filament) muscle Z-line, alpha 1 | 1.77014 |
| 14 | Hs.431279 | NSF | N-ethylmaleimide-sensitive factor | 4.20439 |
| 15 | Hs.155975 | PTPRCAP | protein tyrosine phosphatase, receptor type, C-associated protein | -1.77658 |
| 16 | Hs.458272 | MPO | myeloperoxidase | 1.71345 |
| 17 | Hs.433615 | TUBB2C | tubulin, beta 2C | -1.76403 |
| 18 | Hs.184233 | HSPA9 | heat shock 70 kDa protein 9 (mortalin) | 6.35072 |
| 19 | Hs.295917 | ATP6V1B2 | ATPase, H+ transporting, lysosomal 56/58 kDa, V1 subunit B2 | 2.24142 |
| 20 | Hs.521640 | RAD23B | RAD23 homolog B (S. cerevisiae) | 1.96378 |
| 21 | Hs.699880 | RPS10 | ribosomal protein S10 | 3.17111 |
| 22 | Hs.546285 | RPLP0 (includes EG: 6175) | ribosomal protein, large, P0 | 2.03495 |
| 23 | Hs.389649 | EIF4A3 (includes EG: 9775) | eukaryotic translation initiation factor 4A, isoform 3 | 1.89742 |
| 24 | Hs.511251 | SQRDL (includes EG: 58472) | sulfide quinone reductase-like (yeast) | 2.33602 |
| 25 | Hs.26010 | PFKP | phosphofructokinase, platelet | -2.73727 |
| 26 | Hs.78888 | DBI | diazepam binding inhibitor (GABA receptor modulator, acyl-Coenzyme A binding protein) | 2.47829 |
| 27 | Hs.405144 | SFRS3 | splicing factor, arginine/serine-rich 3 | 4.47655 |
| 28 | Hs.413812 | RAC1 | ras-related C3 botulinum toxin substrate 1 (rho family, small GTP binding protein Rac1) | 2.76246 |
| 29 | Hs.558351 | KIF2A | kinesin heavy chain member 2A | -1.41796 |
| 30 | Hs.355934 | SFPQ | splicing factor proline/glutamine-rich (polypyrimidine tract binding protein associated) | 2.45856 |
| 31 | Hs.464336 | P4HB | prolyl 4-hydroxylase, beta polypeptide | 2.20506 |
| 32 | Hs.131151 | PSMD9 | proteasome (prosome, macropain) 26S subunit, non-ATPase, 9 | -1.67257 |
| 33 | Hs.247362 | DDAH2 | dimethylarginine dimethylaminohydrolase 2 | 1.98084 |
| 34 | Hs.356654 | PSMC1 | proteasome (prosome, macropain) 26S subunit, ATPase, 1 | 2.36445 |
| 35 | Hs.527105 | HNRPDL | heterogeneous nuclear ribonucleoprotein D-like | 5.14561 |
| 36 | Hs.472838 | STK4 | serine/threonine kinase 4 | 1.65603 |
| 37 | Hs.373763 | HNRNPR | heterogeneous nuclear ribonucleoprotein R | 3.23939 |

TABLE G-continued

| | International Protein Index/UniGene | Symbol | Entrez Gene Name | Fold Change (positive numbers are upregulated in B1) |
|---|---|---|---|---|
| 38 | Hs.440898 | FCN1 | ficolin (collagen/fibrinogen domain containing) 1 | 3.12337 |
| 39 | Hs.178551 | RPL8 | ribosomal protein L8 | 2.39479 |
| 40 | Hs.644646 | KIF5B | kinesin family member 5B | −1.81795 |
| 41 | Hs.153837 | MNDA | myeloid cell nuclear differentiation antigen | 2.21411 |
| 42 | Hs.627414 | RPS18 | ribosomal protein S18 | 2.94127 |
| 43 | Hs.546287 | RPS7 | ribosomal protein S7 | 1.83705 |
| 44 | Hs.497788 | EPRS | glutamyl-prolyl-tRNA synthetase | 1.99658 |
| 45 | Hs.511743 | TUBB3 | tubulin, beta 3 | −1.48195 |
| 46 | Hs.270291 | ACTN4 | actinin, alpha 4 | 2.09181 |
| 47 | Hs.119251 | UQCRC1 | ubiquinol-cytochrome c reductase core protein I | 2.05968 |
| 48 | Hs.699298 | CDV3 | CDV3 homolog (mouse) | 1.35707 |
| 49 | Hs.111779 | SPARC | secreted protein, acidic, cysteine-rich (osteonectin) | −3.78710 |
| 50 | Hs.651923 | CNN2 | calponin 2 | 2.25485 |
| 51 | Hs.465511 | GZMM | granzyme M (lymphocyte met-ase 1) | 2.38354 |
| 52 | Hs.2853 | PCBP1 (includes EG: 5093) | poly(rC) binding protein 1 | 1.65937 |
| 53 | Hs.690198 | CDC42 | cell division cycle 42 (GTP binding protein, 25 kDa) | 1.59084 |
| 54 | Hs.271510 | GSR | glutathione reductase | 2.59620 |
| 55 | Hs.406277 | SF3A1 | splicing factor 3a, subunit 1, 120 kDa | 2.92334 |
| 56 | Hs.571177 | SYNCRIP | synaptotagmin binding, cytoplasmic RNA interacting protein | 3.05703 |
| 57 | Hs.695941 | HK1 | hexokinase 1 | 1.48167 |
| 58 | Hs.250758 | PSMC3 | proteasome (prosome, macropain) 26S subunit, ATPase, 3 | 1.90255 |
| 59 | Hs.707 | KRT2 | keratin 2 | 3.19828 |
| 60 | Hs.594444 | LMNA | lamin A/C | 2.42545 |
| 61 | Hs.2490 | CASP1 | caspase 1, apoptosis-related cysteine peptidase (interleukin 1, beta, convertase) | 2.18090 |
| 62 | Hs.75307 | H1FX | H1 histone family, member X | 2.60755 |
| 63 | Hs.534639 | HADHB | hydroxyacyl-Coenzyme A dehydrogenase/3-ketoacyl-Coenzyme A thiolase/enoyl-Coenzyme A hydratase (trifunctional protein), beta subunit | 2.04804 |
| 64 | Hs.30054 | F5 | coagulation factor V (proaccelerin, labile factor) | −2.31510 |
| 65 | Hs.533040 | PDLIM7 | PDZ and LIM domain 7 (enigma) | −2.15116 |
| 66 | Hs.665429 | DDX17 | DEAD (Asp-Glu-Ala-Asp) box polypeptide 17 | 2.97738 |
| 67 | Hs.695185 | NAP1L1 | nucleosome assembly protein 1-like 1 | −1.56121 |
| 68 | Hs.75841 | ERP29 | endoplasmic reticulum protein 29 | 3.53236 |
| 69 | Hs.523302 | PRDX3 | peroxiredoxin 3 | 1.71589 |
| 70 | IPI00024989 | PCMT1 | protein-L-isoaspartate (D-aspartate) O-methyltransferase | 2.22172 |
| 71 | Hs.430606 | CS | citrate synthase | −2.53628 |
| 72 | Hs.520973 | HSPB1 | heat shock 27 kDa protein 1 | 1.89406 |
| 73 | Hs.118958 | STX11 | syntaxin 11 | −1.57367 |
| 74 | Hs.610830 | PRKCSH | protein kinase C substrate 80K—H | 2.25450 |
| 75 | Hs.14601 | HCLS1 | hematopoietic cell-specific Lyn substrate 1 | 2.13579 |
| 76 | Hs.632828 | HNRNPH2 | heterogeneous nuclear ribonucleoprotein H2 (H') | 3.09381 |
| 77 | Hs.694128 | RPS14 | ribosomal protein S14 | 2.10304 |
| 78 | Hs.356624 | NID1 | nidogen 1 | −4.10930 |
| 79 | Hs.12084 | TUFM | Tu translation elongation factor, mitochondrial | 1.77413 |
| 80 | Hs.95950 | PKLR | pyruvate kinase, liver and RBC | 2.55932 |
| 81 | Hs.654614 | HSPA6 | heat shock 70 kDa protein 6 (H5P70B') | 1.28057 |
| 82 | Hs.471441 | PSMB2 | proteasome (prosome, macropain) subunit, beta type, 2 | 3.18295 |
| 83 | Hs.7744 | NDUFV1 | NADH dehydrogenase (ubiquinone) flavoprotein 1, 51 kDa | 2.82524 |
| 84 | Hs.480073 | HNRNPD | heterogeneous nuclear ribonucleoprotein D (AU-rich element RNA binding protein 1, 37 kDa) | 2.72172 |
| 85 | Hs.98791 | ACTR1B (includes EG: 10120) | ARP1 actin-related protein 1 homolog B, centractin beta (yeast) | 3.00772 |
| 86 | IPI00029625 | FLOT2 | flotillin 2 | 3.53456 |
| 87 | Hs.11355 | TMPO | thymopoietin | 3.65290 |
| 88 | Hs.571841 | RPL7 | ribosomal protein L7 | 1.81095 |
| 89 | Hs.699271 | STAT1 | signal transducer and activator of transcription 1, 91 kDa | 2.36973 |
| 90 | Hs.529451 | DIAPH1 | diaphanous homolog 1 (Drosophila) | 1.44181 |
| 91 | Hs.516032 | HADHA | hydroxyacyl-Coenzyme A dehydrogenase/3-ketoacyl-Coenzyme A thiolase/enoyl-Coenzyme A hydratase (trifunctional protein), alpha subunit | 4.43165 |
| 92 | Hs.503043 | CPT1A | carnitine palmitoyltransferase 1A (liver) | −1.45507 |
| 93 | Hs.475074 | PARVB | parvin, beta | −1.93236 |
| 94 | Hs.655396 | PSMD11 | proteasome (prosome, macropain) 26S subunit, non-ATPase, 11 | 1.89081 |
| 95 | Hs.122523 | SND1 | staphylococcal nuclease and tudor domain containing 1 | 2.96927 |
| 96 | Hs.444075 | UBASH3B | ubiquitin associated and SH3 domain containing, B | −1.85814 |
| 97 | Hs.473144 | CASS4 | Cas scaffolding protein family member 4 | −2.58235 |
| 98 | Hs.436186 | CAST | calpastatin | 1.48337 |
| 99 | Hs.465808 | HNRNPM | heterogeneous nuclear ribonucleoprotein M | 2.64995 |
| 100 | Hs.506759 | ATP2A2 | ATPase, Ca++ transporting, cardiac muscle, slow twitch 2 | −1.44671 |
| 101 | Hs.535581 | TPM3 | tropomyosin 3 | 2.05422 |
| 102 | Hs.654720 | KIAA1967 | KIAA1967 | 3.42772 |
| 103 | Hs.515517 | RPL18 | ribosomal protein L18 | 3.72595 |
| 104 | Hs.438429 | RPS19 | ribosomal protein S19 | 4.78644 |
| 105 | IPI00216134 | TPM1 | tropomyosin 1 (alpha) | −1.36995 |

TABLE G-continued

| | International Protein Index/UniGene | Symbol | Entrez Gene Name | Fold Change (positive numbers are upregulated in B1) |
|---|---|---|---|---|
| 106 | Hs.128548 | WDR1 | WD repeat domain 1 | 4.48437 |
| 107 | Hs.519320 | VDAC1 | voltage-dependent anion channel 1 | 1.94443 |
| 108 | Hs.512675 | RPS8 | ribosomal protein S8 | 3.35144 |
| 109 | IPI00216633 | EPB49 | erythrocyte membrane protein band 4.9 (dematin) | −1.84863 |
| 110 | Hs.496622 | PLS3 | plastin 3 (T isoform) | 3.79198 |
| 111 | Hs.654438 | ANK1 | ankyrin 1, erythrocytic | 2.45336 |
| 112 | Hs.417303 | SPTB | spectrin, beta, erythrocytic | 1.95917 |
| 113 | Hs.89497 | LMNB1 | lamin B1 | 2.53206 |
| 114 | Hs.172631 | ITGAM | integrin, alpha M (complement component 3 receptor 3 subunit) | 6.14877 |
| 115 | Hs.652308 | MTHFD1 | methylenetetrahydrofolate dehydrogenase (NADP+ dependent) 1, methenyltetrahydrofolate cyclohydrolase, formyltetrahydrofolate synthetase | 1.36675 |
| 116 | Hs.411312 | ITGA2B (includes EG: 3674) | integrin, alpha 2b (platelet glycoprotein IIb of IIb/IIIa complex, antigen CD41) | 3.09010 |
| 117 | Hs.76392 | ALDH1A1 | aldehyde dehydrogenase 1 family, member A1 | −1.59383 |
| 118 | Hs.500756 | GOT1 | glutamic-oxaloacetic transaminase 1, soluble (aspartate aminotransferase 1) | 1.42300 |
| 119 | Hs.514196 | RPL27 | ribosomal protein L27 | 2.67384 |
| 120 | Hs.445351 | LGALS1 | lectin, galactoside-binding, soluble, 1 | 2.14691 |
| 121 | Hs.80828 | KRT1 | keratin 1 | 3.95879 |
| 122 | Hs.654559 | HNRNPL | heterogeneous nuclear ribonucleoprotein L | −3.40543 |
| 123 | Hs.119825 | SPTA1 | spectrin, alpha, erythrocytic 1 (elliptocytosis 2) | 1.66210 |
| 124 | Hs.446588 | RPS13 | ribosomal protein S13 | 3.62921 |
| 125 | Hs.433427 | RPS17 (includes EG: 6218) | ribosomal protein S17 | 4.39840 |
| 126 | Hs.483305 | HINT1 | histidine triad nucleotide binding protein 1 | −2.04047 |
| 127 | Hs.476448 | FLNB | filamin B, beta (actin binding protein 278) | −1.82786 |
| 128 | Hs.350899 | CAPN2 | calpain 2, (m/II) large subunit | 2.86704 |
| 129 | Hs.520967 | MDH2 | malate dehydrogenase 2, NAD (mitochondrial) | 2.20250 |
| 130 | Hs.371563 | RAB14 | RAB14, member RAS oncogene family | 1.66010 |
| 131 | Hs.83722 | EPS15 | epidermal growth factor receptor pathway substrate 15 | 2.14994 |
| 132 | Hs.580681 | SAMHD1 | SAM domain and HD domain 1 | 2.17687 |
| 133 | Hs.88778 | CBR1 | carbonyl reductase 1 | 1.69648 |
| 134 | Hs.497599 | WARS | tryptophanyl-tRNA synthetase | 1.58361 |
| 135 | Hs.517622 | UNC84B | unc-84 homolog B (C. elegans) | 1.78160 |
| 136 | Hs.523145 | DDOST | dolichyl-diphosphooligosaccharide-protein glycosyltransferase | 1.71412 |
| 137 | Hs.539684 | EIF2S3 | eukaryotic translation initiation factor 1, subunit 3 gamma, 52 kDa | 2.09125 |
| 138 | Hs.201978 | PTGS1 | prostaglandin-endoperoxide synthase 1 (prostaglandin G/H synthase and cyclooxygenase) | −1.72382 |
| 139 | Hs.370770 | XPO1 | exportin 1 (CRM1 homolog, yeast) | 2.13295 |
| 140 | Hs.696016 | SNX2 | sorting nexin 2 | 1.83066 |
| 141 | Hs.181301 | CTSS | cathepsin S | 2.66342 |
| 142 | Hs.204238 | LCN2 | lipocalin 2 | −2.88567 |
| 143 | Hs.212102 | PDIA6 | protein disulfide isomerase family A, member 6 | 2.67256 |
| 144 | Hs.465041 | HDHD2 | haloacid dehalogenase-like hydrolase domain containing 2 | 1.58049 |
| 145 | Hs.125113 | CCT8 | chaperonin containing TCP1, subunit 8 (theta) | 2.74083 |
| 146 | Hs.218040 | ITGB3 | integrin, beta 3 (platelet glycoprotein IIIa, antigen CD61) | −2.86872 |
| 147 | Hs.126941 | FAM49B | family with sequence similarity 49, member B | 2.41970 |
| 148 | Hs.140452 | M6PRBP1 | mannose-6-phosphate receptor binding protein 1 | 2.45483 |
| 149 | Hs.591940 | APOA4 | apolipoprotein A-IV | 2.29544 |
| 150 | Hs.519756 | STK10 | serine/threonine kinase 10 | 2.91394 |
| 151 | Hs.274402 | HSPA1A | heat shock 70 kDa protein 1A | 3.13788 |
| 152 | Hs.571886 | AKR7A2 | aldo-keto reductase family 7, member A2 (aflatoxin, aldehyde reductase) | 2.51928 |
| 153 | Hs.599481 | EIF4A2 | eukaryotic translation initiation factor 4A, isoform 2 | 3.52387 |
| 154 | Hs.352224 | EDARADD | EDAR-associated death domain | 7.46803 |
| 155 | Hs.534385 | THOC4 | THO complex 4 | −1.32827 |
| 156 | Hs.528668 | RPL6 | ribosomal protein L6 | 3.03691 |
| 157 | Hs.368084 | LRPPRC | leucine-rich PPR-motif containing | −1.71518 |
| 158 | Hs.632717 | MYL6 | myosin, light chain 6, alkali, smooth muscle and non-muscle | 3.02347 |
| 159 | Hs.482043 | NNT | nicotinamide nucleotide transhydrogenase | 2.26497 |
| 160 | Hs.525600 | HSP90AA1 | heat shock protein 90 kDa alpha (cytosolic), class A member 1 | 2.84841 |
| 161 | Hs.513530 | TGFB1I1 | transforming growth factor beta 1 induced transcript 1 | −2.45685 |
| 162 | Hs.369920 | RAP1B | RAP1B, member of RAS oncogene family | −2.37358 |
| 163 | Hs.148340 | RPL10A (includes EG: 4736) | ribosomal protein L10a | 1.99520 |
| 164 | Hs.200716 | MECP2 | methyl CpG binding-protein 2 (Rett syndrome) | 2.99376 |
| 165 | Hs.642813 | VIM | vimentin | 1.75207 |
| 166 | Hs.570791 | LAP3 | leucine aminopeptidase 3 | 2.49300 |
| 167 | Hs.516539 | HNRNPA3 | heterogeneous nuclear ribonucleoprotein A3 | 1.70158 |
| 168 | Hs.356572 | RPS3A | ribosomal protein S3A | 3.02357 |
| 169 | Hs.518530 | PAK2 | p21 protein (Cdc42/Rac)-activated kinase 2 | 2.61046 |
| 170 | Hs.37617 | MYO1G | myosin IG | 2.16324 |
| 171 | Hs.467408 | TRIM28 | tripartite motif-containing 28 | 2.84983 |
| 172 | Hs.136905 | HUWE1 | HECT, UBA and WWE domain containing 1 | 1.88641 |
| 173 | IPI00454990 | GP1BB | glycoprotein Ib (platelet), beta polypeptide | −1.88206 |

TABLE G-continued

| | International Protein Index/UniGene | Symbol | Entrez Gene Name | Fold Change (positive numbers are upregulated in B1) |
|---|---|---|---|---|
| 174 | Hs.617193 | CYCS (includes EG: 54205) | cytochrome c, somatic | 1.64385 |
| 175 | Hs.595053 | HSPD1 | heat shock 60 kDa protein 1 (chaperonin) | 1.76318 |
| 176 | Hs.534770 | PKM2 | pyruvate kinase, muscle | 1.27869 |
| 177 | Hs.166463 | HNRNPU | heterogeneous nuclear ribonucleoprotein U (scaffold attachment factor A) | 2.79696 |
| 178 | Hs.2533 | ALDH9A1 | aldehyde dehydrogenase 9 family, member A1 | 1.38474 |
| 179 | Hs.700575 | STMN1 | stathmin 1/oncoprotein 18 | 2.31540 |
| 180 | Hs.530687 | RNH1 | ribonuclease/angiogenin inhibitor 1 | 1.64737 |
| 181 | Hs.696144 | TXNRD1 | thioredoxin reductase 1 | 1.70635 |
| 182 | Hs.502756 | AHNAK | AHNAK nucleoprotein | 6.50929 |
| 183 | Hs.10842 | RAN | RAN, member RAS oncogene family | 2.05198 |
| 184 | Hs.311609 | DDX39 | DEAD (Asp-Glu-Ala-Asp) box polypeptide 39 | 2.85922 |
| 185 | Hs.533273 | UBA1 | ubiquitin-like modifier activating enzyme 1 | 1.88773 |
| 186 | Hs.695946 | ITGB1 | integrin, beta 1 (fibronectin receptor, beta polypeptide, antigen CD29 includes MDF2, MSK12) | −3.90341 |
| 187 | IPI00646888 | 1-Sep | septin 1 | 2.21854 |
| 188 | Hs.546232 | RPS27A | ribosomal protein S27a | −1.51316 |

TABLE H

| | International Protein Index/UniGene | Symbol | Entrez Gene Name |
|---|---|---|---|
| 1 | Hs.1012 | C4BPA | complement component 4 binding protein, alpha |
| 2 | Hs.110675 | APOC1 | apolipoprotein C-I |
| 3 | Hs.116448 | GLS | Glutaminase |
| 4 | Hs.191215 | CYTH1 | cytohesin 1 |
| 5 | Hs.202 | TSPO | translocator protein (18 kDa) |
| 6 | Hs.203637 | PLS1 | plastin 1 (I isoform) |
| 7 | Hs.24889 | FMN2 | formin 2 |
| 8 | Hs.327527 | SMARCA4 | SWI/SNF related, matrix associated, actin dependent regulator of chromatin, subfamily a, member 4 |
| 9 | Hs.352224 | EDARADD | EDAR-associated death domain |
| 10 | Hs.464813 | PSMA8 | proteasome (prosome, macropain) subunit, alpha type, 8 |
| 11 | Hs.466910 | CDA | cytidine deaminase |
| 12 | Hs.4779 | GATAD2B | GATA zinc finger domain containing 2B |
| 13 | Hs.482873 | TMED5 | transmembrane emp24 protein transport domain containing 5 |
| 14 | Hs.501200 | RGS10 | regulator of G-protein signaling 10 |
| 15 | Hs.518750 | OCIAD1 | OCIA domain containing 1 |
| 16 | Hs.529023 | ZNF532 | zinc finger protein 532 |
| 17 | Hs.594444 | LMNA | lamin A/C |
| 18 | Hs.620557 | ANK2 | ankyrin 2, neuronal |
| 19 | Hs.653263 | CEP110 | centrosomal protein 110 kDa |
| 20 | Hs.654438 | ANK1 | ankyrin 1, erythrocytic |
| 21 | Hs.69771 | CFB | complement factor B |
| 22 | Hs.77741 | KNG1 (includes EG: 3827) | kininogen 1 |
| 23 | Hs.83634 | HCFC1 | host cell factor C1 (VP16-accessory protein) |
| 24 | IPI00010951 | EPPK1 | epiplakin 1 |
| 25 | IPI00382606 | F7 | coagulation factor VII (serum prothrombin conversion accelerator) |
| 26 | IPI00641229 | IGHA2 | immunoglobulin heavy constant alpha 2 (A2m marker) |
| 27 | IPI00645452 | TUBB | tubulin, beta |
| 28 | IPI00787190 | HLA-B | major histocompatibility complex, class I, B |

TABLE I

| | Unigene/IPI | Symbol | Entrez Gene Name |
|---|---|---|---|
| 1 | Hs.406758 | HIBADH | 3-hydroxyisobutyrate dehydrogenase |
| 2 | Hs.656685 | HIBCH | 3-hydroxyisobutyryl-Coenzyme A hydrolase |
| 3 | Hs.643487 | ACAA1 | acetyl-Coenzyme A acyltransferase 1 |
| 4 | Hs.558296 | ACP1 | acid phosphatase 1, soluble |
| 5 | Hs.514581 | ACTG1 | actin, gamma 1 |
| 6 | Hs.461727 | ACSF3 | acyl-CoA synthetase family member 3 |
| 7 | Hs.464137 | ACOX1 | acyl-Coenzyme A oxidase 1, palmitoyl |
| 8 | Hs.512815 | AP3D1 | adaptor-related protein complex 3, delta 1 subunit |
| 9 | Hs.470907 | AK2 | adenylate kinase 2 |
| 10 | Hs.525330 | ARF6 | ADP-ribosylation factor 6 |

TABLE I-continued

|    | Unigene/IPI | Symbol | Entrez Gene Name |
|----|-------------|--------|------------------|
| 11 | Hs.62578 | ARFGEF2 | ADP-ribosylation factor guanine nucleotide-exchange factor 2 (brefeldin A-inhibited) |
| 12 | Hs.418167 | ALB | albumin |
| 13 | Hs.632733 | ALDH2 | aldehyde dehydrogenase 2 family (mitochondrial) |
| 14 | Hs.591631 | AGPS | alkylglycerone phosphate synthase |
| 15 | Hs.499725 | ANK3 | ankyrin 3, node of Ranvier (ankyrin G) |
| 16 | Hs.696087 | ANKFY1 | ankyrin repeat and FYVE domain containing 1 |
| 17 | Hs.412117 | ANXA6 | annexin A6 |
| 18 | Hs.3346 | ANXA9 | annexin A9 |
| 19 | Hs.435771 | API5 | apoptosis inhibitor 5 |
| 20 | Hs.503165 | ARAP1 | ArfGAP with RhoGAP domain, ankyrin repeat and PH domain 1 |
| 21 | Hs.465224 | NARS | asparaginyl-tRNA synthetase |
| 22 | Hs.477126 | ATG3 | ATG3 autophagy related 3 homolog (S. cerevisiae) |
| 23 | Hs.486063 | ATG5 (includes EG: 9474) | ATG5 autophagy related 5 homolog (S. cerevisiae) |
| 24 | Hs.584905 | ATL1 | atlastin GTPase 1 |
| 25 | Hs.85539 | ATP5I | ATP synthase, H+ transporting, mitochondrial F0 complex, subunit E |
| 26 | Hs 656515 | ATP5J2 | ATP synthase, H+ transporting, mitochondrial F0 complex, subunit F2 |
| 27 | Hs.444957 | ATP8A2 | ATPase, aminophospholipid transporter-like, class I, type 8A, member 2 |
| 28 | Hs.517338 | ATP6V1E1 | ATPase, H+ transporting, lysosomal 31 kDa, V1 subunit E1 |
| 29 | Hs.491737 | ATP6V1H | ATPase, H+ transporting, lysosomal 50/57 kDa, V1 subunit H |
| 30 | Hs.429294 | ABCA1 | ATP-binding cassette, sub-family A (ABC1), member 1 |
| 31 | Hs.508423 | ABCC4 | ATP-binding cassette, sub-family C (CFTR/MRP), member 4 |
| 32 | Hs.355983 | BZW1 | basic leucine zipper and W2 domains 1 |
| 33 | Hs.591768 | BTF3 | basic transcription factor 3 |
| 34 | Hs.494614 | BAT2D1 | BAT2 domain containing 1 |
| 35 | Hs.631546 | BAX | BCL2-associated X protein |
| 36 | Hs.654740 | BRWD1 | bromodomain and WD repeat domain containing 1 |
| 37 | Hs.418533 | BUB3 | budding uninhibited by benzimidazoles 3 homolog (yeast) |
| 38 | IPI00797310 | CLSTN3 | calsyntenin 3 |
| 39 | Hs.524809 | CLIP1 | CAP-GLY domain containing linker protein 1 |
| 40 | Hs.699182 | CPT2 | carnitine palmitoyltransferase 2 |
| 41 | Hs.504096 | C8L | Cas-Br-M (murine) ecotropic retroviral transforming sequence |
| 42 | Hs.654616 | CASP6 | caspase 6, apoptosis-related cysteine peptidase |
| 43 | Hs.460232 | CNOT1 | CCR4-NOT transcription complex, subunit 1 |
| 44 | Hs.485518 | CD2AP | CD2-associated protein |
| 45 | Hs.502328 | CD44 | CD44 molecule (Indian blood group) |
| 46 | Hs.556638 | CISD2 | CDGSH iron sulfur domain 2 |
| 47 | Hs.472027 | CDS2 | CDP-diacylglycerol synthase (phosphatidate cytidylyltransferase) 2 |
| 48 | Hs.568242 | CREG1 | cellular repressor of E1A-stimulated genes 1 |
| 49 | Hs.31819 | C1ORF128 | chromosome 1 open reading frame 128 |
| 50 | Hs.368353 | C1ORF71 | chromosome 1 open reading frame 71 |
| 51 | Hs.611057 | C1ORF77 | chromosome 1 open reading frame 77 |
| 52 | Hs.462033 | C1ORF93 | chromosome 1 open reading frame 93 |
| 53 | Hs.8360 | C11ORF54 | chromosome 11 open reading frame 54 |
| 54 | Hs.530753 | C11ORF59 | chromosome 11 open reading frame 59 |
| 55 | IPI00373869 | C17ORF49 | chromosome 17 open reading frame 49 |
| 56 | Hs.368266 | CLTCL1 | clathrin, heavy chain-like 1 |
| 57 | Hs.591506 | MYCBP | c-myc binding protein |
| 58 | Hs.505652 | COPZ1 | coatomer protein complex, subunit zeta 1 |
| 59 | Hs.655010 | CHCHD3 | coiled-coil-helix-coiled-coil-helix domain containing 3 |
| 60 | Hs.369614 | COPS2 | COP9 constitutive photomorphogenic homolog subunit 2 (Arabidopsis) |
| 61 | Hs.502917 | CCS | copper chaperone for superoxide dismutase |
| 62 | Hs.460923 | CBFB | core-binding factor, beta subunit |
| 63 | Hs.372286 | CUL3 | cullin 3 |
| 64 | Hs.518198 | CSTA (includes EG: 1475) | cystatin A (stefin A) |
| 65 | Hs.481898 | CCBL2 | cysteine conjugate-beta lyase 2 |
| 66 | Hs.513803 | CYBA | cytochrome b-245, alpha polypeptide |
| 67 | Hs.461131 | CYB5B | cytochrome b5 type B (outer mitochondrial membrane) |
| 68 | IPI00017510 | COX2 | cytochrome c oxidase II |
| 69 | Hs.696092 | CLASP2 | cytoplasmic linker associated protein 2 |
| 70 | Hs.99120 | DDX3Y (includes EG: 8653) | DEAD (Asp-Glu-Ala-Asp) box polypeptide 3, Y-linked |
| 71 | Hs.75189 | DAP | death-associated protein |
| 72 | Hs.368203 | DOCK11 | dedicator of cytokinesis 11 |
| 73 | Hs.654567 | DENND4A | DENN/MADD domain containing 4A |
| 74 | Hs.407618 | DSG4 | desmoglein 4 |
| 75 | Hs.9857 | DCXR | dicarbonyl/L-xylulose reductase |
| 76 | Hs.335551 | DLAT | dihydrolipoamide S-acetyltransferase |
| 77 | Hs.37916 | DPP7 | dipeptidyl-peptidase 7 |
| 78 | Hs.515210 | DNAJB1 | DnaJ (Hsp40) homolog, subfamily B, member 1 |
| 79 | Hs.656476 | DNAJC3 | DnaJ (Hsp40) homolog, subfamily C, member 3 |
| 80 | Hs.425801 | DUSP23 | dual specificity phosphatase 23 |
| 81 | Hs.522413 | DNM1 | dynamin 1 |
| 82 | Hs.529495 | DYNC1LI1 | dynein, cytoplasmic 1, light intermediate chain 1 |
| 83 | Hs.591176 | DYNLL2 | dynein, light chain, LC8-type 2 |
| 84 | Hs.4747 | DKC1 | dyskeratosis congenita 1, dyskerin |
| 85 | Hs.412103 | EFHA1 | EF-hand domain family, member A1 |
| 86 | Hs.654553 | ETFB (includes EG: 2109) | electron-transfer-flavoprotein, beta polypeptide |
| 87 | Hs.509791 | ERH | enhancer of rudimentary homolog (Drosophila) |
| 88 | Hs.429879 | EHHADH | enoyl-Coenzyme A, hydratase/3-hydroxyacyl Coenzyme A dehydrogenase |

TABLE I-continued

| | Unigene/IPI | Symbol | Entrez Gene Name |
|---|---|---|---|
| 89 | Hs.419815 | EGF | epidermal growth factor (beta-urogastrone) |
| 90 | Hs.477498 | EEFSEC | eukaryotic elongation factor, selenocysteine-tRNA-specific |
| 91 | Hs.429180 | EIF2S2 | eukaryotic translation initiation factor 2, subunit 2 beta, 38 kDa |
| 92 | Hs.696322 | EIF2C2 | eukaryotic translation initiation factor 2C, 2 |
| 93 | Hs.55682 | EIF3D | eukaryotic translation initiation factor 3, subunit D |
| 94 | Hs.502244 | EIF3M | eukaryotic translation initiation factor 3, subunit M |
| 95 | Hs.467084 | EIF4G3 | eukaryotic translation initiation factor 4 gamma, 3 |
| 96 | Hs.433702 | EIF5 | eukaryotic translation initiation factor 5 |
| 97 | Hs.483494 | ETF1 | eukaryotic translation termination factor 1 |
| 98 | Hs.517293 | F11R | F11 receptor |
| 99 | Hs.518662 | FAM129A | family with sequence similarity 129, member A |
| 100 | Hs.490795 | FAM62B | family with sequence similarity 62 (C2 domain containing) member B |
| 101 | Hs.335918 | FDPS | farnesyl diphosphate synthase (farnesyl pyrophosphate synthetase, dimethylallyltranstransferase, geranyltranstransferase) |
| 102 | Hs.86131 | FADD (includes EG: 8772) | Fas (TNFRSF6)-associated via death domain |
| 103 | Hs.408061 | FABP5 | fatty acid binding protein 5 (psoriasis-associated) |
| 104 | Hs.433300 | FCER1G | Fc fragment of IgE, high affinity I, receptor for; gamma polypeptide |
| 105 | Hs.509343 | FERMT2 | fermitin family homolog 2 (*Drosophila*) |
| 106 | Hs.338207 | FRAP1 | FK506 binding protein 12-rapamycin associated protein 1 |
| 107 | Hs.407190 | FKBP5 | FK506 binding protein 5 |
| 108 | Hs.409065 | FEN1 | flap structure-specific endonuclease 1 |
| 109 | Hs.494496 | FBP1 | fructose-1,6-bisphosphatase 1 |
| 110 | Hs.654961 | FUT8 | fucosyltransferase 8 (alpha (1,6) fucosyltransferase) |
| 111 | Hs.390567 | FYN | FYN oncogene related to SRC, FGR, YES |
| 112 | Hs.530024 | GGCT | gamma-glutamyl cyclotransferase |
| 113 | Hs.27059 | GMPPA | GDP-mannose pyrophosphorylase A |
| 114 | Hs.567488 | GMPPB | GDP-mannose pyrophosphorylase B |
| 115 | Hs.591069 | GBAS | glioblastoma amplified sequence |
| 116 | Hs.654465 | GCLC | glutamate-cysteine ligase, catalytic subunit |
| 117 | Hs.390667 | GSTK1 | glutathione S-transferase kappa 1 |
| 118 | Hs.59138 | GYPC | glycophorin C (Gerbich blood group) |
| 119 | Hs.344151 | GOLGA4 | golgi autoantigen, golgin subfamily a, 4 |
| 120 | Hs.431317 | GORASP2 | golgi reassembly stacking protein 2, 55 kDa |
| 121 | Hs.290243 | GBF1 | golgi-specific brefeldin A resistant guanine nucleotide exchange factor 1 |
| 122 | Hs.485449 | GTPBP2 | GTP binding protein 2 |
| 123 | Hs.495134 | GAPVD1 | GTPase activating protein and VPS9 domains 1 |
| 124 | Hs.591450 | GBP7 | guanylate binding protein 7 |
| 125 | Hs.655196 | HP | haptoglobin |
| 126 | Hs.531785 | HS1BP3 | HCLS1 binding protein 3 |
| 127 | Hs.36927 | HSPH1 | heat shock 105 kDa/110 kDa protein 1 |
| 128 | Hs.690634 | HSPA1L | heat shock 70 kDa protein 1-like |
| 129 | Hs.432648 | HSPA2 | heat shock 70 kDa protein 2 |
| 130 | Hs.509736 | HSP90AB1 | heat shock protein 90 kDa alpha (cytosolic), class B member 1 |
| 131 | Hs.525084 | HECTD3 | HECT domain containing 3 |
| 132 | Hs.642618 | HEBP1 | heme binding protein 1 |
| 133 | IPI00784636 | HBB (includes EG: 3043) | hemoglobin, beta |
| 134 | Hs.699280 | HBD | hemoglobin, delta |
| 135 | Hs.502617 | HNRNPCL1 | heterogeneous nuclear ribonucleoprotein C-like 1 |
| 136 | Hs.69293 | HEXB | hexosaminidase B (beta polypeptide) |
| 137 | Hs.83634 | HCFC1 | host cell factor C1 (VP16-accessory protein) |
| 138 | Hs.460002 | FLJ11151 | hypothetical protein FLJ11151 |
| 139 | Hs.78880 | ILVBL | ilvB (bacterial acetolactate synthase)-like |
| 140 | IPI00384938 | IGHG1 | immunoglobulin heavy constant gamma 1 (G1m marker) |
| 141 | Hs.699240 | IPO5 | importin 5 |
| 142 | Hs.434102 | IKBKG | inhibitor of kappa light polypeptide gene enhancer in B-cells, kinase gamma |
| 143 | Hs.500546 | IDE | insulin-degrading enzyme |
| 144 | Hs.513225 | ITFG3 | integrin alpha FG-GAP repeat containing 3 |
| 145 | Hs.375957 | ITGB2 | integrin, beta 2 (complement component 3 receptor 3 and 4 subunit) |
| 146 | Hs.431460 | ICAM2 | intercellular adhesion molecule 2 |
| 147 | Hs.591110 | IDH3A | isocitrate dehydrogenase 3 (NAD+) alpha |
| 148 | Hs.515247 | JAK3 | Janus kinase 3 (a protein tyrosine kinase, leukocyte) |
| 149 | Hs.301613 | JTV1 | JTV1 gene |
| 150 | Hs.527919 | KPNA3 | karyopherin alpha 3 (importin alpha 4) |
| 151 | Hs.270043 | KIAA0196 | KIAA0196 |
| 152 | Hs.368255 | KIAA0368 | KIAA0368 |
| 153 | Hs.368282 | KIAA0564 | KIAA0554 |
| 154 | IPI00396421 | KIAA0776 | KIAA0776 |
| 155 | Hs.654497 | LTBP1 | latent transforming growth factor beta binding protein 1 |
| 156 | Hs.478067 | LXN | latexin |
| 157 | Hs.432674 | LARS | leucyl-tRNA synthetase |
| 158 | Hs.700163 | LY6G5B | lymphocyte antigen 6 complex, locus G5B |
| 159 | Hs.3100 | KARS | lysyl-tRNA synthetase |
| 160 | Hs.654404 | HLA-C | major histocompatibility complex, class I, C |
| 161 | Hs.75694 | MPI | mannose phosphate isomerase |
| 162 | Hs.696082 | MAPKSP1 | MAPK scaffold protein 1 |
| 163 | Hs.444969 | MEMO1 (includes EG: 51072) | mediator of cell motility 1 |
| 164 | Hs.486189 | MAGI3 | membrane associated guanylate kinase, WW and PDZ domain containing 3 |
| 165 | Hs.500842 | MGEA5 | meningioma expressed antigen 5 (hyaluronidase) |

TABLE I-continued

| | Unigene/IPI | Symbol | Entrez Gene Name |
|---|---|---|---|
| 166 | Hs.377155 | MTDH | metadherin |
| 167 | Hs.516157 | MAT2A | methionine adenosyltransferase II, alpha |
| 168 | Hs.252457 | MVD | mevalonate (diphospho) decarboxylase |
| 169 | Hs.580782 | MACF1 | microtubule-actin crosslinking factor 1 |
| 170 | Hs.517949 | MAP4 | microtubule-associated protein 4 |
| 171 | Hs.515860 | MAPRE3 | microtubule-associated protein, RP/EB family, member 3 |
| 172 | Hs.269944 | MTCH2 | mitochondrial carrier homolog 2 (*C. elegans*) |
| 173 | Hs.861 | MAPK3 | mitogen-activated protein kinase 3 |
| 174 | Hs.507681 | MAP3K7IP1 | mitogen-activated protein kinase kinase kinase 7 interacting protein 1 |
| 175 | Hs.643565 | MAPKAPK2 | mitogen-activated protein kinase-activated protein kinase 2 |
| 176 | Hs.591221 | MYCBP2 | MYC binding protein 2 |
| 177 | Hs.91531 | MLLT6 | myeloid/lymphoid or mixed-lineage leukemia (trithorax homolog, *Drosophila*); translocated to, 6 |
| 178 | Hs.655278 | MYOF | myoferlin |
| 179 | Hs.286226 | MYO1C | myosin IC |
| 180 | IPI00719669 | MRLC2 | myosin regulatory light chain MRLC2 |
| 181 | IPI00007858 | MYH13 | myosin, heavy chain 13, skeletal muscle |
| 182 | IPI00001753 | MYH4 | myosin, heavy chain 4, skeletal muscle |
| 183 | Hs.463300 | MYL4 | myosin, light chain 4, alkali; atrial, embryonic |
| 184 | Hs.926 | MX2 | myxovirus (influenza virus) resistance 2 (mouse) |
| 185 | Hs.527412 | ASAH1 | N-acylsphingosine amidohydrolase (acid ceramidase) 1 |
| 186 | Hs.651219 | NDUFA5 | NADH dehydrogenase (ubiquinone) 1 alpha subcomplex, 5, 13 kDa |
| 187 | IPI00074489 | NDUFB10 | NADH dehydrogenase (ubiquinone) 1 beta subcomplex, 10, 22 kDa |
| 188 | Hs.532853 | NDUFB7 | NADH dehydrogenase (ubiquinone) 1 beta subcomplex, 7, 18 kDa |
| 189 | Hs.471207 | NDUFS1 | NADH dehydrogenase (ubiquinone) Fe—S protein 1, 75 kDa (NADH-coenzyme Q reductase) |
| 190 | Hs.90443 | NDUFS8 | NADH dehydrogenase (ubiquinone) Fe—S protein 8, 23 kDa (NADH-coenzyme Q reductase) |
| 191 | Hs.464572 | NDUFV2 | NADH dehydrogenase (ubiquinone) flavoprotein 2, 24 kDa |
| 192 | Hs.473937 | NDUFV3 | NADH dehydrogenase (ubiquinone) flavoprotein 3, 10 kDa |
| 193 | Hs.655006 | NCKIPSD | NCK interacting protein with SH3 domain |
| 194 | Hs.603732 | NCKAP1 | NCK-associated protein 1 |
| 195 | Hs.467759 | NBAS | neuroblastoma amplified sequence |
| 196 | Hs.524116 | NRGN | neurogranin (protein kinase C substrate, RC3) |
| 197 | Hs.587558 | NCF2 | neutrophil cytosolic factor 2 |
| 198 | Hs.493164 | NAPRT1 | nicotinate phosphoribosyltransferase domain containing 1 |
| 199 | Hs.696107 | NEK9 (includes EG: 91754) | NIMA (never in mitosis gene a)- related kinase 9 |
| 200 | Hs.524082 | NLRX1 | NLR family member X1 |
| 201 | Hs.532790 | NMT1 | N-myristoyltransferase 1 |
| 202 | Hs.319334 | NASP | nuclear autoantigenic sperm protein (histone-binding) |
| 203 | Hs.263812 | NUDC | nuclear distribution gene C homolog (*A. nidulans*) |
| 204 | Hs.654408 | NFKB1 | nuclear factor of kappa light polypeptide gene enhancer in B-cells 1 |
| 205 | Hs.325978 | NUMA1 | nuclear mitotic apparatus protein 1 |
| 206 | Hs.79110 | NCL | nucleolin |
| 207 | Hs.643487 | NUP160 | nucleoporin 160 kDa |
| 208 | Hs.555956 | NUDT5 | nudix (nucleoside diphosphate linked moiety X)-type motif 5 |
| 209 | Hs.405410 | OGT (includes EG: 8473) | O-linked N-acetylglucosamine (GlcNAc) transferase (UDP-N-acetylglucosamine:polypeptide-N-acetylglucosaminyl transferase) |
| 210 | Hs.695379 | OPTN | optineurin |
| 211 | Hs.430849 | OSBPL8 | oxysterol binding protein-like 8 |
| 212 | Hs.656789 | PAK3 | p21 protein (Cdc42/Rac)-activated kinase 3 |
| 213 | Hs.98475 | PNKD (includes EG: 25953) | paroxysmal nonkinesigenic dyskinesia |
| 214 | Hs.495471 | PMPCA | peptidase (mitochondrial processing) alpha |
| 215 | Hs.33455 | PADI2 | peptidyl arginine deiminase, type II |
| 216 | IPI00745933 | PPIA (includes EG: 5478) | peptidylprolyl isomerase A (cyclophilin A) |
| 217 | Hs.644938 | PCYT2 | phosphate cytidylyltransferase 2, ethanolamine |
| 218 | Hs.372295 | PITPNM1 | phosphatidylinositol transfer protein, membrane-associated 1 |
| 219 | Hs.272759 | PITPNM2 | phosphatidylinositol transfer protein, membrane-associated 2 |
| 220 | Hs.75812 | PCK2 | phosphoenolpyruvate carboxykinase 2 (mitochondrial) |
| 221 | Hs.75160 | PFKM | phosphofructokinase, muscle |
| 222 | Hs.26612 | PGM2L1 | phosphoglucomutase 2-like 1 |
| 223 | Hs.487296 | PHGDH | phosphoglycerate dehydrogenase |
| 224 | IPI00786982 | PGAM5 | phosphoglycerate mutase family member 5 |
| 225 | Hs.409834 | PHPT1 | phosphohistidine phosphatase 1 |
| 226 | Hs.32942 | PIK3CG | phosphoinositide-3-kinase, catalytic, gamma polypeptide |
| 227 | Hs.591953 | PLCB3 | phospholipase C, beta 3 (phosphatidylinositol-specific) |
| 228 | Hs.413111 | PLCG2 | phospholipase C, gamma 2 (phosphatidylinositol-specific) |
| 229 | Hs.517216 | PEA15 | phosphoprotein enriched in astrocytes 15 |
| 230 | Hs.675491 | PLXNA4 | plexin A4 |
| 231 | Hs.632833 | PLXNB3 | plexin B3 |
| 232 | Hs.348609 | PARP10 | poly (ADP-ribose) polymerase family, member 10 |
| 233 | Hs 482038 | PAIP1 | poly(A) binding protein interacting protein 1 |
| 234 | Hs.507910 | PGRMC2 | progesterone receptor membrane component 2 |
| 235 | Hs.567410 | PSMD14 | proteasome (prosome, macropain) 26S subunit, non-ATPase, 14 |
| 236 | IPI00555590 | PSMB2 | proteasome (prosome, macropain) subunit, beta type, 2 |
| 237 | IPI00064328 | PRMT5 | protein arginine methyltransferase 5 |
| 238 | Hs.498570 | PRKCQ | protein kinase C, theta |
| 239 | Hs.631923 | PRKAR2A | protein kinase, cAMP-dependent, regulatory, type II, alpha |

TABLE I-continued

| | Unigene/IPI | Symbol | Entrez Gene Name |
|---|---|---|---|
| 240 | Hs.514323 | PPP1R9B | protein phosphatase 1, regulatory (inhibitor) subunit 9B |
| 241 | Hs.400740 | PPP2R4 | protein phosphatase 2A activator, regulatory subunit 4 |
| 242 | Hs.584019 | PPP6C | protein phosphatase 6, catalytic subunit |
| 243 | Hs.591549 | PTPN18 | protein tyrosine phosphatase, non-receptor type 18 (brain-derived) |
| 244 | Hs.439152 | PCDH12 | protocadherin 12 |
| 245 | Hs.78524 | PRUNE | prune homolog (*Drosophila*) |
| 246 | Hs.41735 | P2RX1 | purinergic receptor P2X, ligand-gated ion channel, 1 |
| 247 | Hs.284491 | PDXK | pyridoxal (pyridoxine, vitamin B6) kinase |
| 248 | Hs.370781 | PDXDC1 | pyridoxal-dependent decarboxylase domain containing 1 |
| 249 | Hs.470633 | PDK1 | pyruvate dehydrogenase kinase, isozyme 1 |
| 250 | Hs.534770 | PKM2 | pyruvate kinase, muscle |
| 251 | Hs.321541 | RAB11A | RAB11A, member RAS oncogene family |
| 252 | Hs.406799 | RAB18 | RAB18, member RAS oncogene family |
| 253 | Hs.369017 | RAB2A | RAB2A, member RAS oncogene family |
| 254 | Hs.567328 | RAB5B | RAB5B, member RAS oncogene family |
| 255 | Hs.650382 | RAB5C | RAB5C, member RAS oncogene family |
| 256 | Hs.591552 | RAB6C | RAB6C, member RAS oncogene family |
| 257 | Hs.644420 | RAB8A | RAB8A, member RAS oncogene family |
| 258 | Hs.493867 | RCSD1 | RCSD domain containing 1 |
| 259 | Hs.461925 | RPA1 | replication protein A1, 70 kDa |
| 260 | Hs.645283 | RTN4 | reticulon 4 |
| 261 | Hs.368631 | ARHGAP10 | Rho GTPase activating protein 10 |
| 262 | Hs.531807 | ARHGAP25 | Rho GTPase activating protein 25 |
| 263 | Hs.508738 | ARHGFF7 | Rho guanine nucleotide exchange factor (GEF) 7 |
| 264 | Hs.465761 | ARHGEF18 | rho/rac guanine nucleotide exchange factor (GEF) 18 |
| 265 | Hs.73839 | RNASE3 | ribonuclease, RNase A family, 3 (eosinophil cationic protein) |
| 266 | Hs.388664 | RPL11 | ribosomal protein L11 |
| 267 | Hs.374588 | RPL17 | ribosomal protein L17 |
| 268 | Hs.337766 | RPL18A | ribosomal protein L18a |
| 269 | IPI00741405 | LOC391282 | ribosomal protein L23a pseudogene 12 |
| 270 | Hs.649475 | RPL24 | ribosomal protein L24 |
| 271 | Hs.652114 | RPL28 | ribosomal protein L28 |
| 272 | Hs.433701 | RPL37A (includes EG: 6168) | ribosomal protein L37a |
| 273 | IPI00796861 | LOC100130892 | ribosomal protein L7 pseudogene 32 |
| 274 | Hs.546289 | RPS12 (includes EG: 6206) | ribosomal protein S12 |
| 275 | Hs.370504 | RPS15A | ribosomal protein S15a |
| 276 | IPI00401105 | RPS25 | ribosomal protein S25 |
| 277 | IPI00397963 | RPS27 | ribosomal protein S27 |
| 278 | Hs.282376 | RPS4Y1 | ribosomal protein S4, Y-linked 1 |
| 279 | Hs.367761 | RPS4Y2 | ribosomal protein S4, Y-linked 2 |
| 280 | Hs.408073 | RPS6 | ribosomal protein S6 |
| 281 | IPI00413108 | RPSA (includes EG: 3921) | ribosomal protein SA |
| 282 | Hs.553723 | RNF123 (includes EG: 63891) | ring finger protein 123 |
| 283 | Hs.306769 | RUFY1 | RUN and FYVE domain containing 1 |
| 284 | Hs.272822 | RUVBL1 | RuvB-like 1 (*E. coli*) |
| 285 | Hs.515846 | RUVBL2 | RuvB-like 2 (*E. coli*) |
| 286 | Hs.632438 | SEC22B | SEC22 vesicle trafficking protein homolog B (*S. cerevisiae*) |
| 287 | Hs.654429 | SEC24C (includes EG: 9632) | SEC24 family, member C (*S. cerevisiae*) |
| 288 | IPI00643835 | SELP | selectin P (granule membrane protein 140 kDa, antigen CD62) |
| 289 | Hs.632460 | SELENBP1 | selenium binding protein 1 |
| 290 | Hs.283743 | 5-Sep | septin 5 |
| 291 | Hs.440932 | 9-Sep | septin 9 |
| 292 | Hs.435661 | SPTLC2 | serine palmitoyltransferase, long chain base subunit 2 |
| 293 | Hs.433343 | SRRM2 | serine/arginine repetitive matrix 2 |
| 294 | Hs.409578 | STK38 | serine/threonine kinase 38 |
| 295 | IPI00168350 | RP6-213H19.1 | serine/threonine protein kinase MST4 |
| 296 | Hs.368077 | SERPINB8 | serpin peptidase inhibitor, clade B (ovalbumin), member 8 |
| 297 | Hs.531176 | SARS | seryl-tRNA synthetase |
| 298 | Hs.643526 | SETDB1 | SET domain, bifurcated 1 |
| 299 | Hs.285666 | SH3PXD2B | SH3 and PX domains 2B |
| 300 | Hs.601143 | SH3BP1 | SH3-domain binding protein 1 |
| 301 | Hs.514495 | SRP68 | signal recognition particle 68 kDa |
| 302 | Hs.409223 | SSR4 | signal sequence receptor, delta (translocon-associated protein delta) |
| 303 | IPI00399212 | LOC389842 | similar to RanBP1 |
| 304 | Hs.591680 | SCYE1 | small inducible cytokine subfamily E, member 1 (endothelial monocyte-activating) |
| 305 | Hs.356549 | SNRPD3 | small nuclear ribonucleoprotein D3 polypeptide 18 kDa |
| 306 | Hs.632166 | SNRPN | small nuclear ribonucleoprotein polypeptide N |
| 307 | Hs.83753 | SNRPB | small nuclear ribonucleoprotein polypeptides B and B1 |
| 308 | Hs.350927 | SLC25A6 | solute carrier family 25 (mitochondrial carrier; adenine nucleotide translocator), member 6 |
| 309 | Hs.656870 | SLC25A24 | solute carrier family 25 (mitochondrial carrier; phosphate carrier), member 24 |
| 310 | Hs.438723 | SLC27A3 | solute carrier family 27 (fatty acid transporter), member 3 |
| 311 | Hs.656699 | SLC27A4 | solute carrier family 27 (fatty acid transporter), member 4 |
| 312 | Hs.502769 | SLC3A2 | solute carrier family 3 (activators of dibasic and neutral amino acid transport), member 2 |
| 313 | Hs.469116 | SLC9A1 | solute carrier family 9 (sodium/hydrogen exchanger), member 1 |
| 314 | Hs.878 | SORD | sorbitol dehydrogenase |
| 315 | Hs.505824 | SAMM50 | sorting and assembly machinery component 50 homolog (*S. cerevisiae*) |

TABLE I-continued

|   | Unigene/IPI | Symbol | Entrez Gene Name |
|---|---|---|---|
| 316 | Hs.32706 | SPTBN4 | spectrin, beta, non-erythrocytic 4 |
| 317 | Hs.558463 | SPEN | spen homolog, transcriptional regulator (*Drosophila*) |
| 318 | Hs.436306 | SPHKAP | SPHK1 interactor, AKAP domain containing |
| 319 | Hs.406423 | SF3B2 | splicing factor 3b, subunit 2, 145 kDa |
| 320 | Hs.679714 | SFRS1 | splicing factor, arginine/serine-rich 1 |
| 321 | Hs.309090 | SFRS7 | splicing factor, arginine/serine-rich 7, 35 kDa |
| 322 | Hs.591922 | SLK | STE20-like kinase (yeast) |
| 323 | Hs.3439 | STOML2 | stomatin (EPB72)-like 2 |
| 324 | Hs.656726 | STRN | striatin, calmodulin binding protein |
| 325 | Hs.440475 | SDHA (includes EG: 6389) | succinate dehydrogenase complex, subunit A, flavoprotein (Fp) |
| 326 | Hs.465924 | SDHB (includes EG: 6390) | succinate dehydrogenase complex, subunit B, iron sulfur (Ip) |
| 327 | Hs.494827 | SUSD1 | sushi domain containing 1 |
| 328 | Hs.83734 | STX4 | syntaxin 4 |
| 329 | Hs.530436 | STXBP3 | syntaxin binding protein 3 |
| 330 | Hs.643566 | TAOK3 | TAO kinase 3 |
| 331 | IPI00642032 | TXNL1 | thioredoxin-like 1 |
| 332 | Hs.30345 | TRAP1 | TNF receptor-associated protein 1 |
| 333 | Hs.87968 | TLR9 | toll-like receptor 9 |
| 334 | Hs.475733 | TOP2B | topoisomerase (DNA) II beta 180 kDa |
| 335 | Hs.496459 | TOR1AIP1 | torsin A interacting protein 1 |
| 336 | Hs.34024 | TNIK | TRAF2 and NCK interacting kinase |
| 337 | Hs.529618 | TFRC | transferrin receptor (p90, CD71) |
| 338 | Hs.517033 | TGM2 | transglutaminase 2 (C polypeptide, protein-glutamine-gamma-glutamyltransferase) |
| 339 | Hs.96247 | TSNAX | translin-associated factor X |
| 340 | Hs.654824 | TM9SF2 | transmembrane 9 superfamily member 2 |
| 341 | Hs.502 | TAP2 | transporter 2, ATP-binding cassette, sub-family B (MDR/TAP) |
| 342 | IPI00018853 | TPM1 | tropomyosin 1 (alpha) |
| 343 | Hs.535581 | TPM3 | tropomyosin 3 |
| 344 | Hs.497599 | WARS | tryptophanyl-tRNA synthetase |
| 345 | Hs.31053 | TBCB | tubulin folding cofactor B |
| 346 | Hs.279669 | TUBG1 | tubulin, gamma 1 |
| 347 | Hs.473296 | TPD52L2 | tumor protein D52-like 2 |
| 348 | IPI00794254 | YWHAH | tyrosine 3-monooxygenase/tryptophan 5-monooxygenase activation protein, eta polypeptide |
| 349 | Hs.9589 | UBQLN1 | ubiquilin 1 |
| 350 | Hs.5308 | UBA52 | ubiquitin A-52 residue ribosomal protein fusion product 1 |
| 351 | Hs.474213 | UFD1L | ubiquitin fusion degradation 1 like (yeast) |
| 352 | Hs.632370 | UBE4B | ubiquitination factor E4B (UFD2 homolog, yeast) |
| 353 | IPI00019932 | UBE2D2 | ubiquitin-conjugating enzyme E2D 2 (UBC4/5 homolog, yeast) |
| 354 | Hs.50308 | UBE2K | ubiquitin-conjugating enzyme E2K (UBC1 homolog, yeast) |
| 355 | IPI00216316 | UROS | uroporphyrinogen III synthase |
| 356 | Hs.292689 | USO1 | USO1 homolog, vesicle docking protein (yeast) |
| 357 | Hs.499925 | VPS26A | vacuolar protein sorting 26 homolog A (*S. pombe*) |
| 358 | Hs.418175 | VPS28 | vacuolar protein sorting 28 homolog (*S. cerevisiae*) |
| 359 | Hs.592009 | VP533A | vacuolar protein sorting 33 homolog A (*S. cerevisiae*) |
| 360 | Hs.631535 | AKT2 | v-akt murine thymoma viral oncogene homolog 2 |
| 361 | Hs.632066 | VCPIP1 | valosin containing protein (p97)/p47 complex interacting protein 1 |
| 362 | Hs.515469 | VASP | vasodilator-stimulated phosphoprotein |
| 363 | Hs.66708 | VAMP3 | vesicle-associated membrane protein 3 (cellubrevin) |
| 364 | Hs.505033 | KRAS | v-Ki-ras2 Kirsten rat sarcoma viral oncogene homolog |
| 365 | Hs.699154 | LYN | v-yes-1 Yamaguchi sarcoma viral related oncogene homolog |
| 366 | Hs.635221 | WASF3 | WAS protein family, member 3 |
| 367 | Hs.356604 | WNK1 | WNK lysine deficient protein kinase 1 |
| 368 | Hs.390623 | XPNPEP1 | X-prolyl aminopeptidase (aminopeptidase P) 1, soluble |
| 369 | Hs.27239 | ZDHHC5 | zinc finger, DHHC-type containing 5 |
| 370 | Hs.37003 | Not Annotated | Not Annotated |
| 371 | Hs.102696 | Not Annotated | |
| 372 | Hs.10326 | COPE | |
| 373 | Hs.10649 | C1orf38 | |
| 374 | Hs.108049 | Not Annotated | Not Annotated |
| 375 | Hs.108957 | Not Annotated | Not Annotated |
| 376 | Hs.111024 | Not Annotated | Not Annotated |
| 377 | Hs.115242 | Not Annotated | Not Annotated |
| 378 | Hs.116237 | Not Annotated | Not Annotated |
| 379 | Hs.11638 | ACSL5 | |
| 380 | Hs.119825 | Not Annotated | Not Annotated |
| 381 | Hs.124027 | Not Annotated | Not Annotated |
| 382 | Hs.124126 | Not Annotated | Not Annotated |
| 383 | Hs.12865 | NSFL1C | |
| 384 | Hs.131255 | Not Annotated | Not Annotated |
| 385 | Hs.131489 | Not Annotated | Not Annotated |
| 386 | Hs.132499 | Not Annotated | Not Annotated |
| 387 | Hs.132858 | Not Annotated | Not Annotated |
| 388 | Hs.133512 | Not Annotated | Not Annotated |
| 389 | Hs.134688 | Not Annotated | Not Annotated |
| 390 | Hs.136309 | Not Annotated | Not Annotated |
| 391 | Hs.138378 | Not Annotated | Not Annotated |
| 392 | Hs.141125 | Not Annotated | Not Annotated |

TABLE I-continued

| | Unigene/IPI | Symbol | Entrez Gene Name |
|---|---|---|---|
| 393 | Hs.142003 | Not Annotated | Not Annotated |
| 394 | Hs.1422 | FGR | |
| 395 | Hs.1437 | GAA | |
| 396 | Hs.143703 | EHD4 | |
| 397 | Hs.144011 | CYTH2 | |
| 398 | Hs.144447 | BRWD2 | |
| 399 | Hs.146406 | DEDD | |
| 400 | Hs.146602 | UQCRQ | |
| 401 | Hs.149957 | RPS6KA1 | |
| 402 | Hs.150206 | HIST1H1A | |
| 403 | Hs.150718 | JAM3 /// LOC100133502 | |
| 404 | Hs.152944 | VWA5A | |
| 405 | Hs.154078 | LBP | |
| 406 | Hs.155975 | PTPRCAP | |
| 407 | Hs.158331 | RENBP | |
| 408 | Hs.15977 | NDUFB9 | |
| 409 | Hs.161357 | PDHB | |
| 410 | Hs.162121 | COPA | |
| 411 | Hs.16355 | MYH10 | |
| 412 | Hs.163867 | CD14 | |
| 413 | Hs.166011 | CTNND1 | |
| 414 | Hs.166551 | FAM114A2 | |
| 415 | Hs.166924 | SEC13 | |
| 416 | Hs.169284 | PRPS1L1 | |
| 417 | Hs.169900 | PABPC4 | |
| 418 | Hs.171626 | SKP1 | |
| 419 | Hs.173043 | MTA2 | |
| 420 | Hs.17614 | ABCB10 | |
| 421 | Hs.179309 | UBQLN2 | |
| 422 | Hs.18192 | SRRM1 | |
| 423 | Hs.182625 | VAPB | |
| 424 | Hs.1872 | Not Annotated | Not Annotated |
| 425 | Hs.188401 | ANXA10 | |
| 426 | Hs.188882 | NUDT3 | |
| 427 | Hs.189075 | TWF1 | |
| 428 | Hs.18925 | CRBN | |
| 429 | Hs.189409 | FNBP1 | |
| 430 | Hs.190086 | MRCL3 | |
| 431 | Hs.191213 | SNX9 | |
| 432 | Hs.194148 | YES1 | |
| 433 | Hs.195080 | ECE1 | |
| 434 | Hs.196437 | MOBKL1B | |
| 435 | Hs.200804 | SDCBP | |
| 436 | Hs.204041 | AHSA1 | |
| 437 | Hs.2057 | Not Annotated | Not Annotated |
| 438 | Hs.211463 | DNM2 | |
| 439 | Hs.21160 | ME1 | |
| 440 | Hs.212088 | EPHX2 | |
| 441 | Hs.213389 | GOLGB1 | |
| 442 | Hs.213470 | PSMB7 | |
| 443 | Hs.214142 | MTHFR | |
| 444 | Hs.220594 | CCDC58 | |
| 445 | Hs.224171 | ENO3 | |
| 446 | Hs.238839 | SCYL1 | |
| 447 | Hs.239818 | PIK3CB | |
| 448 | Hs.24956 | INF2 | |
| 449 | Hs.271954 | Not Annotated | Not Annotated |
| 450 | Hs.296422 | Not Annotated | Not Annotated |
| 451 | Hs.301658 | 1554440_at | 1554440_at |
| 452 | Hs.328865 | Not Annotated | Not Annotated |
| 453 | Hs.351544 | Not Annotated | Not Annotated |
| 454 | Hs.368359 | Not Annotated | Not Annotated |
| 455 | Hs.370503 | Not Annotated | Not Annotated |
| 456 | Hs.37712 | AW006941 | AW006941 |
| 457 | Hs.43505 | AF091453 | |
| 458 | Hs.435775 | Not Annotated | Not Annotated |
| 459 | Hs.439474 | Not Annotated | Not Annotated |
| 460 | Hs.440534 | Not Annotated | Not Annotated |
| 461 | Hs.460988 | Not Annotated | Not Annotated |
| 462 | Hs.470544 | Not Annotated | Not Annotated |
| 463 | Hs.471528 | Not Annotated | Not Annotated |
| 464 | Hs.486856 | Not Annotated | Not Annotated |
| 465 | Hs.500674 | Not Annotated | Not Annotated |
| 466 | Hs.590925 | Not Annotated | Not Annotated |
| 467 | Hs.591005 | Not Annotated | Not Annotated |
| 468 | Hs.591366 | Not Annotated | Not Annotated |
| 469 | Hs.599301 | Not Annotated | Not Annotated |
| 470 | Hs.632735 | Not Annotated | Not Annotated |

TABLE I-continued

| | Unigene/IPI | Symbol | Entrez Gene Name |
|---|---|---|---|
| 471 | Hs.637017 | Not Annotated | Not Annotated |
| 472 | Hs.645248 | Not Annotated | Not Annotated |
| 473 | Hs.654497 | Not Annotated | Not Annotated |
| 474 | Hs.659335 | Not Annotated | Not Annotated |
| 475 | Hs.694210 | Not Annotated | Not Annotated |
| 476 | Hs.696132 | Not Annotated | Not Annotated |
| 477 | Hs.699333 | Not Annotated | Not Annotated |
| 478 | Hs.699367 | Not Annotated | Not Annotated |
| 479 | Hs.700648 | Not Annotated | Not Annotated |
| 480 | Hs.700676 | Not Annotated | Not Annotated |
| 481 | Hs.700760 | Not Annotated | Not Annotated |
| 482 | IPI00011791 | Not Annotated | Not Annotated |
| 483 | IPI00026138 | Not Annotated | Not Annotated |
| 484 | IPI00027007 | Not Annotated | Not Annotated |
| 485 | IPI00061977 | Not Annotated | Not Annotated |
| 486 | IPI00140827 | Not Annotated | Not Annotated |
| 487 | IPI00152990 | Not Annotated | Not Annotated |
| 488 | IPI00165486 | Not Annotated | |
| 489 | IPI00167258 | Not Annotated | |
| 490 | IPI00176593 | Not Annotated | |
| 491 | IPI00176692 | Not Annotated | |
| 492 | IPI00176854 | Not Annotated | |
| 493 | IPI00332493 | Not Annotated | |
| 494 | IPI00386403 | Not Annotated | |
| 495 | IPI00397713 | Not Annotated | |
| 496 | IPI00397808 | Not Annotated | |
| 497 | IPI00398435 | Not Annotated | |
| 498 | IPI00412216 | Not Annotated | |
| 499 | IPI00457006 | Not Annotated | |
| 500 | IPI00478310 | Not Annotated | |
| 501 | IPI00556589 | Not Annotated | |
| 502 | IPI00738024 | Not Annotated | |
| 503 | IPI00745518 | Not Annotated | |
| 504 | IPI00746177 | Not Annotated | |
| 505 | IPI00788196 | Not Annotated | |
| 506 | IPI00792850 | Not Annotated | |
| 507 | IPI00796208 | Not Annotated | |
| 508 | IPI00797737 | Not Annotated | |
| 509 | IPI00807559 | Not Annotated | |
| 510 | IPI00807559 | Not Annotated | |

TABLE J

| | International Protein Index/UniGene | Symbol | Entrez Gene Name | Fold Change (positive numbers are upregulated in B1) |
|---|---|---|---|---|
| 1 | Hs.180946 | RPL5 (includes EG: 6125) | ribosomal protein L5 | 2.991594141 |
| 2 | Hs.520026 | VARS | valyl-tRNA synthetase | 1.788666142 |
| 3 | Hs.664670 | Not Annotated | | 1.863546477 |
| 4 | IPI00001539 | ACAA2 | acetyl-Coenzyme A acyltransferase 2 | 1.778012617 |
| 5 | Hs.631827 | ANXA7 | annexin A7 | 1.962977658 |
| 6 | Hs.466044 | PKN1 | protein kinase N1 | 2.926215231 |
| 7 | Hs.90093 | HSPA4 | heat shock 70 kDa protein 4 | 2.324540439 |
| 8 | Hs.185172 | GNB2 | guanine nucleotide binding protein (G protein), beta polypeptide 2 | 2.321199972 |
| 9 | IPI00003438 | DNAJC8 | DnaJ (Hsp40) homolog, subfamily C, member 8 | 3.049698528 |
| 10 | Hs.431850 | MAPK1 | mitogen-activated protein kinase 1 | 1.472676636 |
| 11 | Hs.50382 | TJP2 | tight junction protein 2 (zona occludens 2) | 2.014271952 |
| 12 | Hs.180414 | Not Annotated | | 1.683155132 |
| 13 | Hs.186350 | RPL4 | ribosomal protein L4 | 2.710518039 |
| 14 | Hs.699250 | B2M | beta-2-microglobulin | 2.103571916 |
| 15 | Hs.591897 | Not Annotated | | 2.715551514 |
| 16 | Hs.489284 | ARPC1B | actin related protein 2/3 complex, subunit 1B, 41 kDa | 2.034992123 |
| 17 | Hs.514934 | CAPZA1 | capping protein (actin filament) muscle Z-line, alpha 1 | 2.337884511 |
| 18 | Hs.431279 | NSF | N-ethylmaleimide-sensitive factor | 2.608040048 |
| 19 | Hs.700570 | APP | amyloid beta (A4) precursor protein | −2.395893698 |
| 20 | Hs.279259 | EPX | eosinophil peroxidase | 2.005473585 |
| 21 | Hs.644618 | SLC25A5 | solute carrier family 25 (mitochondrial carrier; adenine nucleotide translocator), member 5 | 2.377793261 |
| 22 | Hs.477155 | ATP6V1A | ATPase, H+ transporting, lysosomal 70 kDa, V1 subunit A | 1.592166761 |
| 23 | Hs.75318 | TUBA4A | tubulin, alpha 4a | 1.410317852 |
| 24 | Hs.184233 | HSPA9 | heat shock 70 kDa protein 9 (mortalin) | 3.890588764 |
| 25 | Hs.521640 | RAD23B | RAD23 homolog B (S. cerevisiae) | 1.945040444 |

TABLE J-continued

| | International Protein Index/UniGene | Symbol | Entrez Gene Name | Fold Change (positive numbers are upregulated in B1) |
|---|---|---|---|---|
| 26 | Hs.370581 | CAP1 | CAP, adenylate cyclase-associated protein 1 (yeast) | 2.08626543 |
| 27 | Hs.522969 | PADI4 | peptidyl arginine deiminase, type IV | −2.585597629 |
| 28 | Hs.483408 | Not Annotated | | 2.427608273 |
| 29 | Hs.437594 | RPLP2 | ribosomal protein, large, P2 | 1.762376912 |
| 30 | Hs.546285 | RPLP0 (includes EG: 6175) | ribosomal protein, large, P0 | 2.401809197 |
| 31 | Hs.300816 | RAB1B (includes EG: 81876) | RAB1B, member RAS oncogene family | 2.036788097 |
| 32 | Hs.632535 | SSB (includes EG: 6741) | Sjogren syndrome antigen B (autoantigen La) | 1.848049688 |
| 33 | Hs.38449 | SERPINE2 | serpin peptidase inhibitor, clade E (nexin, plasminogen activator inhibitor type 1), member 2 | 1.839116473 |
| 34 | Hs.374596 | TPT1 (includes EG: 7178) | tumor protein, translationally-controlled 1 | 1.916065103 |
| 35 | Hs.148559 | IMMT | inner membrane protein, mitochondrial (mitofilin) | 2.208812239 |
| 36 | Hs.405144 | SFRS3 | splicing factor, arginine/serine-rich 3 | 1.854287873 |
| 37 | Hs.274309 | ERAF | erythroid associated factor | −2.404141665 |
| 38 | Hs.413812 | RAC1 | ras-related C3 botulinum toxin substrate 1 (rho family, small GTP binding protein Rac1) | 3.007255119 |
| 39 | Hs.25318 | RAB27B | RAB27B, member RAS oncogene family | 1.762079978 |
| 40 | Hs.355934 | SFPQ | splicing factor proline/glutamine-rich (polypyrimidine tract binding protein associated) | 2.033693659 |
| 41 | Hs.464336 | P4HB | prolyl 4-hydroxylase, beta polypeptide | 2.058272651 |
| 42 | Hs.247362 | DDAH2 | dimethylarginine dimethylaminohydrolase 2 | 2.191528732 |
| 43 | Hs.527105 | HNRPDL | heterogeneous nuclear ribonucleoprotein D-like | 3.323650054 |
| 44 | Hs.502842 | CAPN1 | calpain 1, (mu/I) large subunit | 1.844181806 |
| 45 | Hs.12970 | PSMD3 | proteasome (prosome, macropain) 26S subunit, non-ATPase, 3 | 1.509756576 |
| 46 | IPI00011891 | Not Annotated | | 1.949391219 |
| 47 | Hs.373763 | HNRNPR | heterogeneous nuclear ribonucleoprotein R | 3.183271632 |
| 48 | Hs.440898 | FCN1 | ficolin (collagen/fibrinogen domain containing) 1 | −1.921894928 |
| 49 | Hs.644646 | KIF5B | kinesin family member 5B | −1.435375448 |
| 50 | Hs.63348 | EMILIN1 | elastin microfibril interfacer 1 | 1.663039334 |
| 51 | Hs.153837 | MNDA | myeloid cell nuclear differentiation antigen | 1.689289277 |
| 52 | Hs.656176 | RBM4 | RNA binding motif protein 4 | 1.899826892 |
| 53 | Hs.77793 | CSK | c-src tyrosine kinase | 1.724761961 |
| 54 | Hs.627414 | RPS18 | ribosomal protein S18 | 3.348251322 |
| 55 | Hs.497788 | EPRS | glutamyl-prolyl-tRNA synthetase | 1.466442524 |
| 56 | Hs.698340 | Not Annotated | | 1.921786734 |
| 57 | Hs.699298 | CDV3 | CDV3 homolog (mouse) | 1.486895919 |
| 58 | Hs.111779 | SPARC | secreted protein, acidic, cysteine-rich (osteonectin) | −2.780445145 |
| 59 | IPI00011891 | PRKAA1 | protein kinase, AMP-activated, alpha 1 catalytic subunit | 2.713587735 |
| 60 | Hs.495541 | C9ORF167 | chromosome 9 open reading frame 167 | 1.599094872 |
| 61 | Hs.651923 | CNN2 | calponin 2 | 1.731782614 |
| 62 | Hs.131711 | DLD | dihydrolipoamide dehydrogenase | 1.948923988 |
| 63 | Hs.644809 | Not Annotated | | 2.338316865 |
| 64 | Hs.643072 | RAB10 | RAB10, member RAS oncogene family | 1.911187131 |
| 65 | Hs.2853 | PCBP1 (includes EG: 5093) | poly(rC) binding protein 1 | 1.878028726 |
| 66 | Hs.19121 | AP2A2 | adaptor-related protein complex 2, alpha 2 subunit | 2.290995374 |
| 67 | Hs.690198 | CDC42 | cell division cycle 42 (GTP binding protein, 25 kDa) | 2.382171241 |
| 68 | Hs.271510 | GSR | glutathione reductase | 2.161827645 |
| 69 | Hs.524161 | RSU1 | Ras suppressor protein 1 | 1.436279998 |
| 70 | Hs.406277 | SF3A1 | splicing factor 3a, subunit 1, 120 kDa | 3.35665152 |
| 71 | Hs.558314 | CP | ceruloplasmin (ferroxidase) | −4.832439476 |
| 72 | Hs.75514 | NP (includes EG: 4860) | nucleoside phosphorylase | 1.500961251 |
| 73 | Hs.501684 | NAP1L4 | nucleosome assembly protein 1-like 4 | 2.209825746 |
| 74 | Hs.571177 | SYNCRIP | synaptotagmin binding, cytoplasmic RNA interacting protein | 2.269580549 |
| 75 | Hs.695941 | HK1 | hexokinase 1 | 1.893698231 |
| 76 | Hs.368149 | CCT7 | chaperonin containing TCP1, subunit 7 (eta) | 1.433906814 |
| 77 | Hs.695925 | DUSP3 | dual specificity phosphatase 3 | 2.286782204 |
| 78 | Hs.75066 | TSN | translin | −2.048787544 |
| 79 | Hs.474751 | MYH9 | myosin, heavy chain 9, non-muscle | 2.033216171 |
| 80 | Hs.644809 | Not Annotated | | 3.013475764 |
| 81 | Hs.655207 | F2 | coagulation factor II (thrombin) | −2.861439244 |
| 82 | Hs.143436 | PLG | plasminogen | −1.893142835 |
| 83 | Hs.420529 | UBE2V1 | ubiquitin-conjugating enzyme E2 variant 1 | 3.119742802 |
| 84 | Hs.190028 | GSTO1 | glutathione S-transferase omega 1 | 1.353315555 |
| 85 | Hs.20107 | KLC1 | kinesin light chain 1 | 1.756378314 |
| 86 | Hs.626404 | RAB11B | RAB11B, member RAS oncogene family | 1.540804975 |
| 87 | Hs.460109 | MYH11 | myosin, heavy chain 11, smooth muscle | 2.332116359 |
| 88 | Hs.490415 | ZYX | zyxin | 2.38059363 |
| 89 | Hs.138860 | ARHGAP1 | Rho GTPase activating protein 1 | 1.851916091 |
| 90 | Hs.646283 | VISA | virus-induced signaling adapter | 1.446706533 |
| 91 | Hs.8004 | KALRN | kalirin, RhoGEF kinase | 4.58940432 |

TABLE J-continued

| | International Protein Index/UniGene | Symbol | Entrez Gene Name | Fold Change (positive numbers are upregulated in B1) |
|---|---|---|---|---|
| 92 | Hs.594673 | Not Annotated | | 1.559917838 |
| 93 | Hs.707 | KRT2 | keratin 2 | 2.661810703 |
| 94 | Hs.699367 | Not Annotated | | 1.552098437 |
| 95 | Hs.280342 | PRKAR1A | protein kinase, cAMP-dependent, regulatory, type I, alpha (tissue specific extinguisher 1) | 1.634710854 |
| 96 | Hs.73849 | APOC3 | apolipoprotein C-III | 3.025507594 |
| 97 | Hs.546255 | FGG | fibrinogen gamma chain | 2.194270748 |
| 98 | Hs.75307 | H1FX | H1 histone family, member X | 2.411319459 |
| 99 | Hs.632729 | FAM62A | family with sequence similarity 62 (C2 domain containing), member A | 1.737053335 |
| 100 | Hs.120759 | APOB | apolipoprotein B (including Ag(x) antigen) | −3.022308409 |
| 101 | Hs.72933 | PF4V1 | platelet factor 4 variant 1 | −1.667015899 |
| 102 | Hs.507866 | C13ORF15 | chromosome 13 open reading frame 15 | 2.508431485 |
| 103 | Hs.203717 | FN1 | fibronectin 1 | −2.170422372 |
| 104 | Hs.324746 | AHSG | alpha-2-HS-glycoprotein | −4.302298793 |
| 105 | Hs.200770 | SKAP2 | src kinase associated phosphoprotein 2 | 1.755472125 |
| 106 | Hs.30054 | F5 | coagulation factor V (proaccelerin, labile factor) | −1.567648564 |
| 107 | Hs.372208 | HSPC159 | galectin-related protein | 1.824854702 |
| 108 | Hs.505735 | NACA | nascent polypeptide-associated complex alpha subunit | 1.652441243 |
| 109 | Hs.491351 | CLTC | clathrin, heavy chain (Hc) | 1.743502579 |
| 110 | Hs.480042 | ANXA3 | annexin A3 | −3.143396399 |
| 111 | Hs.509226 | FKBP3 | FK506 binding protein 3, 25 kDa | 2.142363841 |
| 112 | Hs.24258 | GUCY1A3 | guanylate cyclase 1, soluble, alpha 3 | 1.848134452 |
| 113 | Hs.81934 | ACADSB | acyl-Coenzyme A dehydrogenase, short/branched chain | 1.352453174 |
| 114 | Hs.429608 | REEP5 | receptor accessory protein 5 | −1.629165972 |
| 115 | Hs.75841 | ERP29 | endoplasmic reticulum protein 29 | 2.32777609 |
| 116 | Hs.413482 | C21ORF33 | chromosome 21 open reading frame 33 | −1.338275818 |
| 117 | Hs.502823 | PRDX5 | peroxiredoxin 5 | 1.612032187 |
| 118 | Hs.523302 | PRDX3 | peroxiredoxin 3 | 1.609936792 |
| 119 | Hs.408054 | RPL12 (includes EG: 6136) | ribosomal protein L12 | 2.804663051 |
| 120 | IPI00024989 | PCMT1 | protein-L-isoaspartate (D-aspartate) O-methyltransferase | 1.567802876 |
| 121 | Hs.591095 | PDIA3 | protein disulfide isomerase family A, member 3 | 1.780599508 |
| 122 | Hs.430606 | CS | citrate synthase | −2.357926195 |
| 123 | Hs.520973 | HSPB1 | heat shock 27 kDa protein 1 | 1.923931973 |
| 124 | Hs.518244 | RPN1 | ribophorin I | 2.112462414 |
| 125 | Hs.695918 | CAPZA2 | capping protein (actin filament) muscle Z-line, alpha 2 | 2.146454384 |
| 126 | Hs.632828 | HNRNPH2 | heterogeneous nuclear ribonucleoprotein H2 (H') | 1.609307106 |
| 127 | Hs.430425 | GNB1 | guanine nucleotide binding protein (G protein), beta polypeptide 1 | 1.915685862 |
| 128 | Hs.469473 | RPL31 | ribosomal protein L31 | 1.971237465 |
| 129 | Hs.381072 | PPIF | peptidylprolyl isomerase F | 1.919712344 |
| 130 | Hs.83190 | FASN | fatty acid synthase | 1.596744982 |
| 131 | Hs.356624 | NID1 | nidogen 1 | −1.567370157 |
| 132 | Hs.12084 | TUFM | Tu translation elongation factor, mitochondrial | 1.443666367 |
| 133 | Hs.95990 | PKLR | pyruvate kinase, liver and RBC | 2.624429792 |
| 134 | Hs.489040 | SRI | sorcin | −1.668251058 |
| 135 | Hs.192374 | HSP90B1 | heat shock protein 90 kDa beta (Grp94), member 1 | 1.227206967 |
| 136 | Hs.516155 | CAPG | capping protein (actin filament), gelsolin-like | 1.935086978 |
| 137 | Hs.928 | PRTN3 | proteinase 3 | −2.191302631 |
| 138 | Hs.179986 | FLOT1 | flotillin 1 | 2.62551323 |
| 139 | Hs.315137 | AARS | alanyl-tRNA synthetase | 2.138071963 |
| 140 | Hs.275243 | S100A6 | S100 calcium binding protein A6 | −2.091908363 |
| 141 | Hs.656274 | TNFAIP8 | tumor necrosis factor, alpha-induced protein 8 | 1.848699684 |
| 142 | Hs.654559 | HNRNPL | heterogeneous nuclear ribonucleoprotein L | 2.064236514 |
| 143 | Hs.471441 | PSMB2 | proteasome (prosome, macropain) subunit, beta type, 2 | 3.189407689 |
| 144 | Hs.594095 | Not Annotated | | 1.541410846 |
| 145 | Hs.7744 | NDUFV1 | NADH dehydrogenase (ubiquinone) flavoprotein 1, 51 kDa | 1.859664494 |
| 146 | Hs.517670 | TTLL12 | tubulin tyrosine ligase-like family, member 12 | 1.548669753 |
| 147 | Hs.159494 | BTK | Bruton agammaglobulinemia tyrosine kinase | 1.744461371 |
| 148 | Hs.153961 | ACTR1A | ARP1 actin-related protein 1 homolog A, centractin alpha (yeast) | 1.602174673 |
| 149 | Hs.98791 | ACTR1B (includes EG: 10120) | ARP1 actin-related protein 1 homolog B, centractin beta (yeast) | 2.447561282 |
| 150 | IPI00029625 | FLOT2 | flotillin 2 | 2.779048389 |
| 151 | Hs.232375 | ACAT1 | acetyl-Coenzyme A acetyltransferase 1 | 1.844709235 |
| 152 | Hs.529451 | DIAPH1 | diaphanous homolog 1 (*Drosophila*) | 1.472455435 |
| 153 | Hs.477352 | PDIA5 | protein disulfide isomerase family A, member 5 | 2.417726204 |
| 154 | Hs.516032 | HADHA | hydroxyacyl-Coenzyme A dehydrogenase/3-ketoacyl-Coenzyme A thiolase/enoyl-Coenzyme A hydratase (trifunctional protein), alpha subunit | 2.919893077 |
| 155 | Hs.528007 | U2AF2 (includes EG: 11338) | U2 small nuclear RNA auxiliary factor 2 | 2.33690845 |
| 156 | Hs.655340 | Not Annotated | | 1.994399205 |
| 157 | Hs.546303 | Not Annotated | | 1.993258019 |
| 158 | Hs.191346 | 7-Sep | septin 7 | 1.426720758 |
| 159 | Hs.556296 | Not Annotated | | 1.918157196 |
| 160 | Hs.546407 | CAND1 | cullin-associated and neddylation-dissociated 1 | 1.355594109 |

TABLE J-continued

| | International Protein Index/UniGene | Symbol | Entrez Gene Name | Fold Change (positive numbers are upregulated in B1) |
|---|---|---|---|---|
| 161 | Hs.122523 | SND1 | staphylococcal nuclease and tudor domain containing 1 | 1.764952427 |
| 162 | Hs.327252 | Not Annotated | | 1.853845796 |
| 163 | IPI00154742 | IGL@ | immunoglobulin lambda locus | −2.322679589 |
| 164 | Hs.514412 | PECAM1 | platelet/endothelial cell adhesion molecule | 1.521872894 |
| 165 | Hs.248267 | MPST | mercaptopyruvate sulfurtransferase | 1.802723925 |
| 166 | Hs.436186 | CAST | calpastatin | 1.877444004 |
| 167 | Hs.390567 | FYN | FYN oncogene related to SRC, FGR, YES | 1.721126996 |
| 168 | IPI00168728 | IGHM | immunoglobulin heavy constant mu | −1.882125059 |
| 169 | Hs.558799 | PSMA3 | proteasome (prosome, macropain) subunit, alpha type, 3 | 2.424171315 |
| 170 | Hs.465808 | HNRNPM | heterogeneous nuclear ribonucleoprotein M | 1.745065443 |
| 171 | Hs.149185 | CNDP2 | CNDP dipeptidase 2 (metallopeptidase M20 family) | 1.639294303 |
| 172 | IPI00179291 | XPNPEP1 | X-prolyl aminopeptidase (aminopeptidase P) 1, soluble | 1.443429746 |
| 173 | Hs.555895 | TMSL3 | thymosin-like 3 | −2.986973706 |
| 174 | Hs.126550 | VPS4B | vacuolar protein sorting 4 homolog B (*S. cerevisiae*) | 1.5707885 |
| 175 | Hs.654720 | KIAA1967 | KIAA1967 | 3.861735646 |
| 176 | Hs.49582 | PPP1R12A | protein phosphatase 1, regulatory (inhibitor) subunit 12A | −1.985284505 |
| 177 | Hs.63489 | PTPN6 | protein tyrosine phosphatase, non-receptor type 6 | 2.403072934 |
| 178 | Hs.535581 | TPM3 | tropomyosin 3 | −1.265339887 |
| 179 | Hs.496984 | MPP1 | membrane protein, palmitoylated 1, 55 kDa | 1.825563177 |
| 180 | Hs.515517 | RPL18 | ribosomal protein L18 | 3.659413318 |
| 181 | Hs.438429 | RPS19 | ribosomal protein S19 | 2.504016487 |
| 182 | Hs.73722 | APEX1 | APEX nuclease (multifunctional DNA repair enzyme) 1 | 2.126641285 |
| 183 | Hs.461047 | G6PD | glucose-6-phosphate dehydrogenase | 1.330805366 |
| 184 | Hs.128548 | WDR1 | WD repeat domain 1 | 5.196770912 |
| 185 | Hs.519320 | VDAC1 | voltage-dependent anion channel 1 | 2.440307464 |
| 186 | Hs.512675 | RPS8 | ribosomal protein S8 | 2.401417871 |
| 187 | Hs.494691 | PFN1 | profilin 1 | 1.824342002 |
| 188 | Hs.180535 | FERMT3 | fermitin family homolog 3 (*Drosophila*) | 1.933107142 |
| 189 | Hs.417303 | SPTB | spectrin, beta, erythrocytic | 2.124657924 |
| 190 | Hs.446628 | Not Annotated | | 2.082461305 |
| 191 | Hs.1869 | PGM1 | phosphoglucomutase 1 | 1.62661576 |
| 192 | Hs.89497 | LMNB1 | lamin B1 | 1.892879233 |
| 193 | Hs.652308 | MTHFD1 | methylenetetrahydrofolate dehydrogenase (NADP+ dependent) 1, methenyltetrahydrofolate cyclohydrolase, formyltetrahydrofolate synthetase | 1.965807135 |
| 194 | Hs.446149 | LDHB | lactate dehydrogenase B | 1.507117812 |
| 195 | Hs.87752 | MSN | moesin | 1.792183522 |
| 196 | Hs.253903 | STOM | stomatin | 1.663466237 |
| 197 | Hs.523836 | GSTP1 | glutathione S-transferase pi 1 | 3.12010713 |
| 198 | Hs.573688 | PRDX6 | peroxiredoxin 6 | 1.768671919 |
| 199 | Hs.80828 | KRT1 | keratin 1 | 2.488668295 |
| 200 | Hs.289123 | DCTN2 | dynactin 2 (p50) | 1.517636012 |
| 201 | Hs.654554 | Not Annotated | | −3.221258193 |
| 202 | Hs.90061 | PGRMC1 | progesterone receptor membrane component 1 | 1.645197721 |
| 203 | Hs.514819 | AP2B1 | adaptor-related protein complex 2, beta 1 subunit | 1.967752606 |
| 204 | Hs.467284 | RPS9 | ribosomal protein S9 | 2.046621121 |
| 205 | Hs.397609 | RPS16 | ribosomal protein S16 | 3.411967491 |
| 206 | Hs.433427 | RPS17 (includes EG: 6218) | ribosomal protein S17 | 3.95408013 |
| 207 | Hs.350899 | CAPN2 | calpain 2, (m/II) large subunit | 1.680232488 |
| 208 | Hs.363137 | TCP1 | t-complex 1 | 1.787923894 |
| 209 | Hs.520967 | MDH2 | malate dehydrogenase 2, NAD (mitochondrial) | 1.559612551 |
| 210 | Hs.699180 | VCL | vinculin | 3.129938695 |
| 211 | Hs.371563 | RAB14 | RAB14, member RAS oncogene family | 2.101732978 |
| 212 | Hs.83722 | EPS15 | epidermal growth factor receptor pathway substrate 15 | 1.373102908 |
| 213 | Hs.277035 | MGLL | monoglyceride lipase | 1.805879512 |
| 214 | Hs.64016 | PROS1 | protein S (alpha) | −2.623015853 |
| 215 | Hs.584790 | PPP2R1B | protein phosphatase 2 (formerly 2A), regulatory subunit A, beta isoform | −1.810743224 |
| 216 | Hs.580681 | SAMHD1 | SAM domain and HD domain 1 | 2.000782596 |
| 217 | Hs.444770 | SH3KBP1 | SH3-domain kinase binding protein 1 | 2.069800255 |
| 218 | Hs.88778 | CBR1 | carbonyl reductase 1 | 1.904274616 |
| 219 | Hs.339278 | COPB1 | coatomer protein complex, subunit beta 1 | 1.443967836 |
| 220 | Hs.592490 | FH | fumarate hydratase | 2.186123666 |
| 221 | Hs.486458 | ARHGAP18 | Rho GTPase activating protein 18 | 2.274383381 |
| 222 | Hs.335513 | F13A1 | coagulation factor XIII, A1 polypeptide | 2.145284002 |
| 223 | Hs.189772 | CCT2 | chaperonin containing TCP1, subunit 2 (beta) | 1.435139731 |
| 224 | Hs.539684 | EIF2S3 | eukaryotic translation initiation factor 2, subunit 3 gamma, 52 kDa | 2.261012155 |
| 225 | Hs.33642 | ARCN1 | archain 1 | 2.07225933 |
| 226 | Hs.370770 | XPO1 | exportin 1 (CRM1 homolog, yeast) | 2.343773987 |
| 227 | Hs.573018 | Not Annotated | | 1.456482565 |
| 228 | Hs.291030 | IQGAP2 | IQ motif containing GTPase activating protein 2 | 1.646289191 |
| 229 | Hs.212102 | PDIA6 | protein disulfide isomerase family A, member 6 | 2.480879671 |
| 230 | Hs.499839 | RPL7A | ribosomal protein L7a | 1.726750017 |
| 231 | Hs.465041 | HDHD2 | haloacid dehalogenase-like hydrolase domain containing 2 | 2.231113926 |

TABLE J-continued

| | International Protein Index/UniGene | Symbol | Entrez Gene Name | Fold Change (positive numbers are upregulated in B1) |
|---|---|---|---|---|
| 232 | Hs.654957 | PPA2 | pyrophosphatase (inorganic) 2 | 2.076884027 |
| 233 | Hs.660070 | Not Annotated | | 2.0488303 |
| 234 | Hs.125113 | CCT8 | chaperonin containing TCP1, subunit 8 (theta) | 2.39782042 |
| 235 | Hs.274402 | HSPA1A | heat shock 70 kDa protein 1A | 2.358211938 |
| 236 | Hs.75285 | ITIH2 | inter-alpha (globulin) inhibitor H2 | −2.825741915 |
| 237 | Hs.571886 | AKR7A2 | aldo-keto reductase family 7, member A2 (aflatoxin aldehyde reductase) | 2.166498126 |
| 238 | Hs.368794 | AP1B1 | adaptor-related protein complex 1, beta 1 subunit | 1.872459483 |
| 239 | Hs.599481 | EIF4A2 | eukaryotic translation initiation factor 4A, isoform 2 | 3.551326775 |
| 240 | Hs.416848 | CTSW | cathepsin W | −1.696934761 |
| 241 | Hs.528668 | RPL6 | ribosomal protein L6 | 2.430141179 |
| 242 | Hs.368084 | LRPPRC | leucine-rich PPR-motif containing | −2.370581231 |
| 243 | Hs.509736 | HSP90AB1 | heat shock protein 90 kDa alpha (cytosolic), class B member 1 | 2.408626383 |
| 244 | Hs.632717 | MYL6 | myosin, light chain 6, alkali, smooth muscle and non-muscle | 3.625359469 |
| 245 | Hs.654614 | HSPA6 | heat shock 70 kDa protein 6 (HSP70B') | 2.880497988 |
| 246 | Hs.567380 | FUBP1 | far upstream element (FUSE) binding protein 1 | 2.457237888 |
| 247 | Hs.525600 | HSP90AA1 | heat shock protein 90 kDa alpha (cytosolic), class A member 1 | 2.30575168 |
| 248 | Hs.699168 | TUBA1B | tubulin, alpha 1b | 1.343588946 |
| 249 | IPI00398135 | Not Annotated | | 1.706927145 |
| 250 | Hs.128420 | VPS4A | vacuolar protein sorting 4 homolog A (S. cerevisiae) | 2.041670779 |
| 251 | Hs.591054 | BID | BH3 interacting domain death agonist | 1.977789146 |
| 252 | Hs.200716 | MECP2 | methyl CpG binding protein 2 (Rett syndrome) | 2.115913201 |
| 253 | Hs.155247 | ALDOC | aldolase C, fructose-bisphosphate | 2.390316052 |
| 254 | Hs.570791 | LAP3 | leucine aminopeptidase 3 | 1.7773007 |
| 255 | Hs.598115 | PPIA (includes EG: 5478) | peptidylprolyl isomerase A (cyclophilin A) | −1.252231897 |
| 256 | Hs.356572 | RPS3A | ribosomal protein S3A | 3.364033062 |
| 257 | Hs.518530 | PAK2 | p21 protein (Cdc42/Rac)-activated kinase 2 | 1.820573252 |
| 258 | Hs.98510 | WDR44 | WD repeat domain 44 | 1.715515466 |
| 259 | IPI00448925 | IGHG1 | immunoglobulin heavy constant gamma 1 (G1m marker) | −2.709398355 |
| 260 | Hs.41045 | UNC13D | unc-13 homolog D (C. elegans) | 1.475081587 |
| 261 | Hs.380956 | Not Annotated | | 2.840678067 |
| 262 | Hs.404321 | GARS | glycyl-tRNA synthetase | 2.140952373 |
| 263 | Hs.306769 | RUFY1 | RUN and FYVE domain containing 1 | 2.531625079 |
| 264 | Hs.292493 | XRCC6 | X-ray repair complementing defective repair in Chinese hamster cells 6 | 1.787163446 |
| 265 | Hs.595053 | HSPD1 | heat shock 60 kDa protein 1 (chaperonin) | 1.255650787 |
| 266 | Hs.699280 | HBD | hemoglobin, delta | −2.913740187 |
| 267 | Hs.655361 | HPR (includes EG: 3250) | haptoglobin-related protein | −4.710560337 |
| 268 | Hs.534770 | PKM2 | pyruvate kinase, muscle | 1.537311441 |
| 269 | Hs.2533 | ALDH9A1 | aldehyde dehydrogenase 9 family, member A1 | 2.429592013 |
| 270 | Hs.530687 | RNH1 | ribonuclease/angiogenin inhibitor 1 | 1.905230817 |
| 271 | Hs.517168 | TAGLN2 | transgelin 2 | 1.822335623 |
| 272 | Hs.14770 | BIN2 | bridging integrator 2 | 1.68853164 |
| 273 | Hs.436439 | TWF2 | twinfilin, actin-binding protein, homolog 2 (Drosophila) | 1.884510405 |
| 274 | Hs.433068 | PRKAR2B | protein kinase, cAMP-dependent, regulatory, type II, beta | 1.54914478 |
| 275 | Hs.502756 | AHNAK | AHNAK nucleoprotein | 2.893577011 |
| 276 | Hs.515876 | NRBP1 | nuclear receptor binding protein 1 | 2.746197889 |
| 277 | Hs.132858 | RAP1GDS1 | RAP1, GTP-GDP dissociation stimulator 1 | 2.107982605 |
| 278 | Hs.311609 | DDX39 | DEAD (Asp-Glu-Ala-Asp) box polypeptide 39 | 2.84761005 |
| 279 | Hs.438678 | TALDO1 | transaldolase 1 | 2.691818999 |
| 280 | IPI00746976 | DNM1L | dynamin 1-like | 1.617915807 |
| 282 | Hs.270428 | SUCLG1 | succinate-CoA ligase, alpha subunit | 2.37225264 |
| 283 | Hs.471014 | TLN1 | talin 1 | 2.579118784 |
| 284 | | | | |

TABLE 2

Protein Transcript Matches of 393 mild CAN consensus genes

| | Probe Set ID | UniGene ID | Gene Title | Gene Symbol |
|---|---|---|---|---|
| 1 | 212224_at | Hs.76392 | aldehyde dehydrogenase 1 family, member A1 | ALDH1A1 |
| 2 | 209970_x_at | Hs.2490 | caspase 1, apoptosis-related cysteine peptidase (interleukin 1, beta, convertase) | CASP1 |
| 3 | 216799_at | Hs.24907 | Coronin, actin binding protein, 2B | CORO2B |
| 4 | 202902_s_at | Hs.181301 | cathepsin S | CTSS |
| 5 | 203276_at | Hs.89497 | lamin B1 | LMNB1 |
| 6 | 1559052_s_at | Hs.518530 | p21 (CDKN1A)-activated kinase 2 | PAK2 |
| 7 | 202803_s_at | Hs.375957 | integrin, beta 2 (antigen CD18 (p95), lymphocyte function-associated antigen 1; macrophage antigen 1 (mac-1) beta subunit | ITGB2 |

TABLE 2-continued

Protein Transcript Matches of 393 mild CAN consensus genes

| | Probe Set ID | UniGene ID | Gene Title | Gene Symbol |
|---|---|---|---|---|
| 8 | 224511_s_at | Hs.408236 | thioredoxin-like 5 /// thioredoxin-like 5 | TXNL5 |
| 9 | 216063_at | Hs.20205 | hemoglobin, beta pseudogene 1 /// hemoglobin, beta pseudogene 1 | HBBP1 |
| 10 | 202277_at | Hs.90458 | serine palmitoyltransferase, long chain base subunit 1 | SPTLC1 |

TABLE 3

Protein Transcript Matches of 1066 mild CAN Data Set 1 genes

| | Probe Set ID | UniGene ID | Gene Title | Gene Symbol |
|---|---|---|---|---|
| 1 | 212224_at | Hs.76392 | aldehyde dehydrogenase 1 family, member A1 | ALDH1A1 |
| 2 | 201089_at | Hs.295917 | ATPase, H+ transporting, lysosomal 56/58 kDa, V1 subunit B, isoform 2 | ATP6V1B2 |
| 3 | 213312_at | Hs.70769 | chromosome 6 open reading frame 162 | C6orf162 |
| 4 | 206011_at | Hs.2490 | caspase 1, apoptosis-related cysteine peptidase (interleukin 1, beta, convertase) | CASP1 |
| 5 | 202902_s_at | Hs.181301 | cathepsin S | CTSS |
| 6 | 204714_s_at | Hs.30054 | coagulation factor V (proaccelerin, labile factor) | F5 |
| 7 | 202957_at | Hs.14601 | Hematopoietic cell-specific Lyn substrate 1 | HCLS1 |
| 8 | 205936_s_at | Hs.411695 | hexokinase 3 (white cell) | HK3 |
| 9 | 204959_at | Hs.153837 | myeloid cell nuclear differentiation antigen /// myeloid cell nuclear differentiation antigen | MNDA |
| 10 | 208875_s_at | Hs.518530 | p21 (CDKN1A)-activated kinase 2 | PAK2 |
| 11 | 207668_x_at | Hs.212102 | protein disulfide isomerase family A, member 6 | PDIA6 |
| 12 | 227516_at | Hs.406277 | splicing factor 3a, subunit 1, 120 kDa | SF3A1 |
| 13 | 217995_at | Hs.511251 | sulfide quinone reductase-like (yeast) | SQRDL |
| 14 | 220966_x_at | Hs.132499 | actin related protein 2/3 complex, subunit 5-like /// actin related protein 2/3 complex, subunit 5-like | ARPC5L |
| 15 | 219505_at | Hs.170310 | cat eye syndrome chromosome region, candidate 1 | CECR1 |
| 16 | 202295_s_at | Hs.148641 | cathepsin H | CTSH |
| 17 | 209759_s_at | Hs.403436 | dodecenoyl-Coenzyme A delta isomerase (3,2 trans-enoyl-Coenzyme A isomerase) | DCI |
| 18 | 204646_at | Hs.335034 | dihydropyrimidine dehydrogenase | DPYD |
| 19 | 218610_s_at | Hs.460002 | hypothetical protein FLJ11151 | FLJ11151 |
| 20 | 209876_s_at | Hs.434996 | G protein-coupled receptor kinase interactor 2 | GIT2 |
| 21 | 201944_at | Hs.69293 | hexosaminidase B (beta polypeptide) | HEXB |
| 22 | 211023_at | Hs.161357 | pyruvate dehydrogenase (lipoamide) beta | PDHB |
| 23 | 202671_s_at | Hs.284491 | pyridoxal (pyridoxine, vitamin B6) kinase | PDXK |
| 24 | 225214_at | Hs.213470 | Proteasome (prosome, macropain) subunit, beta type, 7 | PSMB7 |
| 25 | 217983_at | Hs.529989 | ribonuclease T2 | RNASET2 |
| 26 | 206034_at | Hs.368077 | serpin peptidase inhibitor, clade B (ovalbumin), member 8 | SERPINB8 |
| 27 | 204981_at | Hs.50868 | solute carrier family 22 (organic cation transporter), member 18 | SLC22A18 |
| 28 | 219403_s_at | Hs.44227 | heparanase | HPSE |
| 29 | 232359_at | Hs.226007 | Retinol dehydrogenase 11 (all-trans and 9-cis) | RDH11 |
| 30 | 203485_at | Hs.368626 | reticulon 1 | RTN1 |
| 31 | 221532_s_at | Hs.513055 | WD repeat domain 61 | WDR61 |
| 32 | 208857_s_at | Hs.279257 | protein-L-isoaspartate (D-aspartate) O-methyltransferase | PCMT1 |

TABLE 4

Protein Transcript Matches of 1429 mild CAN Data Set 2 genes

| | Probe Set ID | UniGene ID | Gene Title | Gene Symbol |
|---|---|---|---|---|
| 1 | 201305_x_at | Hs.494604 | acidic (leucine-rich) nuclear phosphoprotein 32 family, member B | ANP32B |
| 2 | 216123_x_at | Hs.514934 | Capping protein (actin filament) muscle Z-line, alpha 1 | CAPZA1 |
| 3 | 209970_x_at | Hs.2490 | caspase 1, apoptosis-related cysteine peptidase (interleukin 1, beta, convertase) | CASP1 |
| 4 | 209789_at | Hs.24907 | coronin, actin binding protein, 2B | CORO2B |
| 5 | 237104_at | Hs.181301 | Cathepsin S | CTSS |
| 6 | 202428_x_at | Hs.78888 | diazepam binding inhibitor (GABA receptor modulator, acyl-Coenzyme A binding protein) | DBI |
| 7 | 235999_at | Hs.480073 | Heterogeneous nuclear ribonucleoprotein D (AU-rich element RNA binding protein 1, 37 kDa) | HNRPD |
| 8 | 243593_s_at | Hs.465808 | Heterogeneous nuclear ribonucleoprotein M | HNRPM |
| 9 | 201841_s_at | Hs.520973 | heat shock 27 kDa protein 1 | HSPB1 |
| 10 | 1566785_x_at | Hs.431279 | Ribosomal protein S7 | NSF |
| 11 | 216253_s_at | Hs.475074 | parvin, beta | PARVB |
| 12 | 215628_x_at | Hs.483408 | Protein phosphatase 2 (formerly 2A), catalytic subunit, alpha isoform | PPP2CA |
| 13 | 200927_s_at | Hs.371563 | RAB14, member RAS oncogene family | RAB14 |

TABLE 4-continued

Protein Transcript Matches of 1429 mild CAN Data Set 2 genes

| | Probe Set ID | UniGene ID | Gene Title | Gene Symbol |
|---|---|---|---|---|
| 14 | 213941_x_at | Hs.546287 | ribosomal protein S7 | RPS7 |
| 15 | 240855_at | Hs.417303 | Spectrin, beta, erythrocytic (includes spherocytosis, clinical type I) | SPTB |
| 16 | 237875_at | Hs.519756 | Serine/threonine kinase 10 | STK10 |
| 17 | 238749_at | Hs.258314 | Brain and reproductive organ-expressed (TNFRSF1A modulator) | BRE |
| 18 | 1565868_at | Hs.502328 | CD44 antigen (homing function and Indian blood group system) | CD44 |
| 18 | 1565868_at | Hs.502328 | CD44 antigen (homing function and Indian blood group system) | CD44 |
| 19 | 226875_at | Hs.368203 | dedicator of cytokinesis 11 | DOCK11 |
| 20 | 208000_at | Hs.86161 | GPI anchored molecule like protein | GML |
| 21 | 243147_x_at | Hs.432674 | Leucyl-tRNA synthetase | LARS |
| 22 | 226253_at | Hs.143774 | leucine rich repeat containing 45 | LRRC45 |
| 23 | 229851_s_at | Hs.8360 | PTD012 protein | PTD012 |
| 24 | 208720_s_at | Hs.282901 | RNA-binding region (RNP1, RRM) containing 2 | RNPC2 |
| 25 | 201742_x_at | Hs.68714 | splicing factor, arginine/serine-rich 1 (splicing factor 2, alternate splicing factor) | SFRS1 |
| 26 | 215274_at | Hs.369271 | solute carrier family 12 (sodium/chloride transporters), member 3 | SLC12A3 |
| 27 | 231324_at | Hs.534350 | SWI/SNF related, matrix associated, actin dependent regulator of chromatin, subfamily b, member 1 | SMARCB1 |
| 28 | 215416_s_at | Hs.3439 | stomatin (EPB72)-like 2 | STOML2 |
| 29 | 206116_s_at | Hs.133892 | tropomyosin 1 (alpha) | TPM1 |
| 30 | 224511_s_at | Hs.408236 | thioredoxin-like 5 /// thioredoxin-like 5 | TXNL5 |
| 31 | 201266_at | Hs.337766 | thioredoxin reductase 1 | TXNRD1 |
| 32 | 243160_at | Hs.363396 | Complement factor H | CFH |
| 33 | 218218_at | Hs.506603 | DIP13 beta | DIP13B |
| 34 | 221942_s_at | Hs.24258 | guanylate cyclase 1, soluble, alpha 3 | GUCY1A3 |
| 35 | 232169_x_at | Hs.90443 | NADH dehydrogenase (ubiquinone) Fe—S protein 8, 23 kDa (NADH-coenzyme Q reductase) | NDUFS8 |
| 36 | 205190_at | Hs.203637 | plastin 1 (I isoform) | PLS1 |
| 37 | 202429_s_at | Hs.435512 | protein phosphatase 3 (formerly 2B), catalytic subunit, alpha isoform (calcineurin A alpha) | PPP3CA |
| 38 | 1555340_x_at | Hs.190334 | RAP1A, member of RAS oncogene family | RAP1A |
| 39 | 1569073_x_at | Hs.327527 | SWI/SNF related, matrix associated, actin dependent regulator of chromatin, subfamily a, member 4 | SMARCA4 |
| 40 | 212577_at | Hs.8118 | structural maintenance of chromosomes flexible hinge domain containing 1 | SMCHD1 |

TABLE 5

Protein Transcript Matches of 545 moderate/severe CAN Data Set 1 genes

| | Probe Set ID | UniGene ID | Gene Title | Gene Symbol |
|---|---|---|---|---|
| 1 | 223598_at | Hs.521640 | RAD23 homolog B (S. cerevisiae) | RAD23B |
| 2 | 208000_at | Hs.86161 | GPI anchored molecule like protein | GML |
| 3 | 1557724_a_at | Hs.407190 | hypothetical protein LOC285847 | LOC285847 |
| 4 | 236356_at | Hs.471207 | NADH dehydrogenase (ubiquinone) Fe—S protein 1, 75 kDa (NADH-coenzyme Q reductase) | NDUFS1 |
| 5 | 238688_at | Hs.133892 | Tropomyosin 1 (alpha) | TPM1 |
| 6 | 218090_s_at | Hs.144447 | bromodomain and WD repeat domain containing 2 | BRWD2 |
| 7 | 200898_s_at | Hs.500842 | meningioma expressed antigen 5 (hyaluronidase) | MGEA5 |
| 8 | 201569_s_at | Hs.505824 | sorting and assembly machinery component 50 homolog (S. cerevisiae) | SAMM50 |
| 9 | 1560854_s_at | Hs.50216 | zinc finger protein 588 | ZNF588 |

TABLE 6

Protein Transcript Matches of 172 moderate/severe CAN Data Set 2 genes

| | Probe Set ID | UniGene ID | Gene Title | Gene Symbol |
|---|---|---|---|---|
| 1 | 216251_s_at | Hs.517670 | KIAA0153 protein | KIAA0153 |
| 2 | 204959_at | Hs.153837 | myeloid cell nuclear differentiation antigen /// myeloid cell nuclear differentiation antigen | MNDA |
| 3 | 227770_at | Hs.128420 | Vacuolar protein sorting 4A (yeast) | VPS4A |
| 4 | 231324_at | Hs.534350 | SWI/SNF related, matrix associated, actin dependent regulator of chromatin, subfamily b, member 1 | SMARCB1 |
| 5 | 209029_at | Hs.530823 | COP9 constitutive photomorphogenic homolog subunit 7A (Arabidopsis) | COPS7A |
| 6 | 218326_s_at | Hs.502176 | leucine-rich repeat-containing G protein-coupled receptor 4 | LGR4 |

TABLE 6-continued

Protein Transcript Matches of 172 moderate/severe CAN Data Set 2 genes

| Probe Set ID | UniGene ID | Gene Title | Gene Symbol |
|---|---|---|---|
| 7 1568619_s_at | Hs.530899 | Hypothetical protein LOC162073 | LOC162073 |
| 8 204994_at | Hs.926 | myxovirus (influenza virus) resistance 2 (mouse) | MX2 |
| 9 205325_at | Hs.334688 | phytanoyl-CoA hydroxylase interacting protein | PHYHIP |

What is claimed is:

1. A method of prognosing, diagnosing or monitoring and treating or reducing progression of CAN/IFTA (chronic allograft nephropathy, interstitial fibrosis and tubular atrophy, or chronic allograft nephropathy and interstitial fibrosis and tubular atrophy) in a subject who has had a kidney transplant, is being administered an immunosuppressant drug, and is in need of such prognosing, diagnosing or monitoring and treating or reducing progression of CAN/IFTA, comprising
   (a) determining in the subject, levels of mRNA expression of at least five genes selected from the genes in Table A, B, C, D, E, F, G, H, I and/or J, said at least five genes including at least one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM;
   (b) based on the expression levels determined in step (a), determining a subtype of CAN/IFTA according to expression levels that have been associated with severity of CAN/IFTA; and
   (c) based on the severity of the subtype determined in step (b), administering to the subject an increased, decreased, or same dose of the immunosuppressant drug, or administering a new immunosuppressant drug to the subject, and optionally performing a procedure on the subject to validate the severity of CAN/IFTA, whereby the method is prognosing, diagnosing or monitoring and treating or reducing progression of CAN/IFTA in the subject.

2. The method of claim 1, wherein the determining of step (b), for each of the levels of mRNA expression of the at least five genes, comprises comparing the level of mRNA expression of the gene in the subject to one or more reference levels of mRNA expression of the gene that have been associated with severity of CAN/IFTA or lack of CAN/IFTA.

3. The method of claim 2, wherein the determining of step (b) further comprises for each of the levels of mRNA expression of the at least five genes, assigning the level of mRNA expression of the gene in the subject a value or other designation providing an indication whether the subject has or is at risk of CAN/IFTA based on the subtype of CAN/IFTA.

4. The method of claim 3, wherein the subject is a human subject, and the level of mRNA expression of each of the at least five genes is assigned a value on a normalized scale that has been associated with a range of levels of mRNA expression in kidney transplant patients with or without CAN/IFTA.

5. The method of claim 3, wherein the level of mRNA expression of each of the at least five genes is further assigned an independent value or other designation providing an indication that the subject has or is at risk of CAN/IFTA, lacks or is not at risk of CAN/IFTA, or that the expression level is uninformative.

6. The method of claim 3, wherein step (b) further comprises, combining the values or designations from the levels of mRNA expression to provide a combined value or designation providing an indication whether the subject has or is at risk of CAN/IFTA.

7. The method of claim 6, wherein the method is repeated at different times on the subject.

8. The method of claim 1, wherein the subject has undergone a kidney transplant within 1-10 years prior to performing step (a).

9. The method of claim 1, wherein step (a) is performed on a blood sample of the subject.

10. The method of claim 9, wherein the blood sample is a peripheral blood sample or a blood plasma sample.

11. The method of claim 10, wherein the peripheral blood sample is a peripheral blood lymphocyte sample.

12. The method of claim 1, wherein in step (a), the determining of the levels of mRNA expression in the subject comprises one or more of the following: (A) hybridizing the mRNA to an array; (B) quantitative nucleic acid amplification; (C) monitoring a signal of an amplified nucleic acid; or (D) quantifying a nucleic acid synthesized from the mRNA.

13. The method of claim 1, wherein the administering in step (c) is administering to the subject an increased or decreased dose of the immunosuppressant drug, or administering a new immunosuppressant drug.

14. The method of claim 13, wherein the administering in step (c) is administering a new immunosuppressive drug to the subject.

15. The method of claim 1, wherein step (c) includes performing a procedure on the subject to validate the severity of CAN/IFTA or risk thereof.

16. The method of claim 1, wherein the kidney transplant comprises a transplanted kidney organ, transplanted kidney tissue, or transplanted kidney cells.

17. The method of claim 1, wherein the subject is human.

18. An array, comprising a support or supports bearing a plurality of nucleic acid probes complementary to a plurality of mRNAs fewer than 5000 in number, wherein the plurality of mRNAs includes mRNAs expressed by at least five genes selected from the genes in Table A, B, C, D, E, F, G, H, I, and/or J, said at least five genes including at least one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM.

19. The method of claim 1, wherein the administering in step (c) is administering to the subject an increased dose of the immunosuppressant drug.

20. The method of claim 1, wherein step (a) comprises determining in the subject, levels of mRNA expression of at least five twenty genes selected from the genes in Table A, B, C, D, E, F, G, H, I, and/or J said at least twenty genes including one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM.

21. The method of claim 1, wherein step (a) comprises determining in the subject, levels of mRNA expression of at least ten genes selected from the genes in Table A, B, C, D, E, F, G, H, I, and/or J said at least ten genes include at least one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM.

22. The array of claim 18, wherein the plurality of mRNAs includes mRNAs expressed by at least twenty genes selected from the genes in Table A, B, C, D, E, F, G, H, I, and/or J said at least twenty genes include at least one or more of comprising SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM.

23. The array of claim 18, wherein the plurality of mRNAs includes mRNAs expressed by at least ten genes selected from the genes in Table A, B, C, D, E, F, G, H, I, and/or J said at least ten genes including at least one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM.

24. A method of prognosing, diagnosing or monitoring CAN/IFTA (chronic allograft nephropathy, interstitial fibrosis and tubular atrophy, or chronic allograft nephropathy and interstitial fibrosis and tubular atrophy) in a subject who has had a kidney transplant, is being administered an immunosuppressant drug, and is in need of such prognosing, diagnosing or monitoring, comprising
(a) determining in the subject, levels of mRNA expression of at least five genes selected from the genes in Table A, B, C, D, E, F, G, H, I, and/or J, said at least five genes including at least one or more of SEC22C, FCER1G, FAM26F, CHCHD3, KLHIL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B a, CLEC4D, CLEC4A, GSTK1, GSTO1, GSTP1, IGHG1, IGHA2, or IGHM,
wherein the determining of expression levels comprises contacting a subject sample comprising mRNAs of the subject with the array of claim 19; and
(b) based on the expression levels determined in step (a), validating severity of CAN/IFTA that has been associated with the expression levels,
whereby the method is prognosing, diagnosing or monitoring severity of CAN/IFTA in the subject based on from the expression levels.

25. A method of prognosing, diagnosing or monitoring CAN/IFTA (chronic allograft nephropathy, interstitial fibrosis and tubular atrophy, or chronic allograft nephropathy and interstitial fibrosis and tubular atrophy) in a subject who has had a kidney transplant, is being administered an immunosuppressant drug, and is in need of such prognosing, diagnosing or monitoring, comprising
(a) determining in the subject, levels of mRNA expression of at least twenty genes selected from the genes in Table A, B, C, D, E, F, G, H, I, and/or J, said at least twenty genes including at least one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM,
wherein the determining of expression levels comprises contacting a subject sample comprising mRNAs of the subject with the array of claim 22; and
(b) based on the expression levels determined in step (a), validating severity of CAN/IFTA that has been associated with the expression levels,
whereby the method is prognosing, diagnosing or monitoring severity of CAN/IFTA in the subject based on the expression levels.

26. A method of prognosing, diagnosing or monitoring CAN/IFTA (chronic allograft nephropathy, interstitial fibrosis and tubular atrophy, or chronic allograft nephropathy and interstitial fibrosis and tubular atrophy) in a subject who has had a kidney transplant, is being administered an immunosuppressant drug, and is in need of such prognosing, diagnosing or monitoring, comprising
(a) determining in the subject, levels of mRNA expression of at least ten genes selected from the genes in Table A, B, C, D, E, F, G, H, I, and/or J, said at least ten genes including at least one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM,
wherein the determining of expression levels comprises contacting a subject sample comprising mRNAs of the subject with the array of claim 23; and
(b) based on the expression levels determined in step (a), validating severity of CAN/IFTA that has been associated with the expression levels,
whereby the method is prognosing, diagnosing or monitoring severity of CAN/IFTA in the subject based on the expression levels.

27. A method of subtyping a CAN/IFTA (chronic allograft nephropathy, interstitial fibrosis and tubular atrophy, or chronic allograft nephropathy and interstitial fibrosis and tubular atrophy), in a subject who has had a kidney transplant, is being administered an immunosuppressant drug and is in need of such subtyping, comprising
(a) determining in the subject, levels of mRNA expression of at least five genes selected from the genes in Table A, B, C, D, E, F, G, H, I, and/or J, said at least five genes including at least one or more of SEC22C, FCER1G, FAM26F, CHCHD3, KLHIL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM,
wherein the determining of expression levels comprises contacting a subject sample comprising mRNAs of the subject with the array of claim 18; and (b) based on the expression levels determined in step (a), determining a subtype of CAN/IFTA according to expression levels that have been associated with severity of CAN/IFTA, whereby the method is subtyping severity of CAN/IFTA in the subject based on the expression levels.

28. A method of subtyping a CAN/IFTA (chronic allograft nephropathy, interstitial fibrosis and tubular atrophy, or chronic allograft nephropathy and interstitial fibrosis and tubular atrophy), in a subject who has had a kidney transplant, is being administered an immunosuppressant drug and is in need of such subtyping, comprising (a) determining in the subject, levels of mRNA expression of at least twenty genes selected from the genes in Table A, B, C, D, E, F, G, H, I, and/or J, said at least twenty genes including one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM, wherein the determining of expression levels comprises contacting a subject sample comprising mRNAs of the subject with the array of claim 22; and (b) based on the expression levels determined in step (a), determining a subtype of CAN/IFTA according to expression levels that have been associated with severity of CAN/IFTA, whereby the method is subtyping severity of CAN/IFTA in the subject based on the expression levels.

29. A method of subtyping a CAN/IFTA (chronic allograft nephropathy, interstitial fibrosis and tubular atrophy, or chronic allograft nephropathy and interstitial fibrosis and tubular atrophy), in a subject who has had a kidney transplant, is being administered an immunosuppressant drug and is in need of such subtyping, comprising (a) determining in the subject, levels of mRNA expression of at least ten genes selected from the genes in Table A, B, C, D, E, F, G, H, I, and/or J, said at least ten genes including at least one or more of SEC22C, FCER1G, FAM26F, CHCHD3, KLHL2, CEP63, RNF175, RNF123, WNT10A, TSPAN33, TSPAN9, KIAA1033, KIAA1324, KIAA0776, KIAA1967, KIAA0196, KIAA0368, KIAA0564, SNRPB, SNRPD3, SNRPN, TOP2B, CLEC4D, CLEC4A, GSTK1, GSTO1, GSTP1, IGHG1, IGHA2, or IGHM, wherein the determining of expression levels comprises contacting a subject sample comprising mRNAs of the subject with the array of claim 23; and (b) based on the expression levels determined in step (a), determining a subtype of CAN/IFTA according to expression levels that have been associated with severity of CAN/IFTA, whereby the method is subtyping severity of CAN/IFTA in the subject based on the expression levels.

* * * * *